US008722919B2

(12) United States Patent
Maruoka et al.

(10) Patent No.: US 8,722,919 B2
(45) Date of Patent: May 13, 2014

(54) PROCESS FOR PRODUCTION OF MONO-SUBSTITUTED ALKYLATED COMPOUND USING ALDIMINE OR DERIVATIVE THEREOF

(75) Inventors: Keiji Maruoka, Kyoto (JP); Toru Inoue, Kobe (JP); Jun Matsumoto, Kobe (JP)

(73) Assignee: Nagase & Co., Ltd., Osaka-shi (JP)

( * ) Notice: Subject to any disclaimer, the term of this patent is extended or adjusted under 35 U.S.C. 154(b) by 1132 days.

(21) Appl. No.: 11/997,168

(22) PCT Filed: Jul. 28, 2006

(86) PCT No.: PCT/JP2006/315457
§ 371 (c)(1),
(2), (4) Date: Jan. 29, 2008

(87) PCT Pub. No.: WO2007/013698
PCT Pub. Date: Feb. 1, 2007

(65) Prior Publication Data
US 2009/0054679 A1 Feb. 26, 2009

(30) Foreign Application Priority Data

Jul. 29, 2005 (JP) ................................. 2005-220757
Dec. 1, 2005 (JP) ................................. 2005-348518

(51) Int. Cl.
*C07C 251/24* (2006.01)
(52) U.S. Cl.
USPC ........................................................ 560/35
(58) Field of Classification Search
None
See application file for complete search history.

(56) References Cited

U.S. PATENT DOCUMENTS

| 4,847,412 | A * | 7/1989 | Boesten et al. ............... 564/164 |
| 6,340,753 | B1 | 1/2002 | Maruoka |
| 2002/0065414 | A1 | 5/2002 | Maruoka |
| 2006/0183896 | A1 | 8/2006 | Maruoka |
| 2007/0135654 | A1 | 6/2007 | Maruoka |
| 2007/0161624 | A1 | 7/2007 | Maruoka |
| 2009/0054679 | A1 | 2/2009 | Maruoka et al. |
| 2009/0270614 | A1 | 10/2009 | Maruoka et al. |
| 2010/0029935 | A1 | 2/2010 | Maruoka et al. |

FOREIGN PATENT DOCUMENTS

| EP | 1 854 796 A1 | 11/2007 |
| EP | 1 870 403 A1 | 12/2007 |
| JP | 2001-48866 | 2/2001 |
| JP | 2002-173492 | 6/2002 |
| JP | 2002-326992 | 11/2002 |
| JP | 2003-081976 | 3/2003 |
| JP | 2003-81976 | 3/2003 |
| JP | 2004-189696 | 7/2004 |
| JP | 2004-238362 | 8/2004 |
| JP | 2004-359578 | 12/2004 |
| JP | 2005-41791 | 2/2005 |
| WO | WO 2006/054366 | 5/2006 |
| WO | WO 2006/093269 A1 | 9/2006 |
| WO | WO 2006/104226 A1 | 10/2006 |

OTHER PUBLICATIONS

Chen Jin-Tai et al., "Synthesis of D-Phenylalanine Using Chiral Phase-Transfer Catalyst", Youji Huaxue, vol. 8, No. 2, p. 164-166, 1988 (with English abstract).
K. Maruoka el al., "Enantioselective Amino Acid Synthesis by Chiral Phase-Transfer Catalysis", Chemical Reviews, vol. 103, No. 8, p. 3013-3028, 2003.
T. Ooi et al., "Practical Catalytic Enantioselective Synthesis of α, α-Dialkyl—α-amino Acids by Chiral Phase-Transfer Catalysis", J. Am. Chem. Soc., vol. 122, No. 21, p. 5228-5229, and Supporting Information (3 Sheets), 2000.
Y. N. Belokon et al., "Copper (II) salen catalysed, asymmetric synthesis of α, α-disubstituted amino acids", Tetrahedron, vol. 60, No. 8, p. 1849-1861, 2004.
Yuichiro Arimura, el at., "Design-gata Chiral Sokan Ido Shokubai o Mochiita Glycine Ester Aldimine Schiff Base no Ko-Enantio Sentakuteki Alkyl-ka Han'no no Kaihatsu", CSJ: The Chemical Society of Japan Dai 86 Shunki Nenkai (2006), Koen Yokoshu II, p. 1073, Mar. 13, 2006 (with partial English translation).
Martin J. O'Donnell, et al., "The Stereoselective Synthesis of α-Amino Acids by Phase-Transfer Catalysis", J. Am. Chem. Soc., 1989, vol. 111, pp. 2353-2355.
Martin J. O'Donnell, The Preparation of Optically Active α- Amino Acids from the Benzophenone Imines of Glycine Derivatives., Aldrichimica Acta, vol. 34, No. 1 2001, pp. 3-15.
Hyeung-geun Park, et al., "Highly Enantioselective Phase-Transfer Catalytic Alkylation in the Preparation of Non-natural α-Amino Acids via Solid Phase Synthesis Using Aldimine Linker", J. Org. Chem., 2005, vol. 70, pp. 1904-1906.
P. Bey, et al., "Synthesis of α-Alkyl and α-Functionalized Methyl-α-Amino Acids", Tetrahedron Letter, 1977, No. 17, pp. 1455-1458.
Masahiko Seki, et al. "A Practical Synthesis of $C_2$-Symmetric Chiral Binaphthyl Ketone Catalyst" Synthesis 2000, No. 12 pp. 1677-1680.
Takashi Ooi, et al., "New, Improved Procedure for the Synthesis of Structurally Diverse N-Spiro $C_2$-Symmetric Chiral Quaternary Ammonium Bromides", J. Org. Chem., 2003, vol. 68, pp. 4576-4578.
Von Schmidt, et al., "Optisch aktive 2,3,4,2',3',4'-Hexamethoxy-diphenyl-dicarbonsäure-6,6' XIII. Mitteilung über natürliche Gerbstoffe[1]", Ann. Chem., 1952, vol. 576, pp. 85-93.
U.S. Appl. No. 11/910,364, filed Oct. 1, 2007, Maruoka, et al.
U.S. Appl. No. 12/443,588, filed Mar. 30, 2009, Maruoka, et al.
Takashi Ooi, et al., "Design of N-Spiro $C_2$-Symmetric Chiral Quaternary Ammonium Bromides as Novel Chiral Phase-Transfer Catalysts: Synthesis and Application to Practical Asymmetric Synthesis of α-Amino Acids", J. Am. Chem. Soc., 2003, vol. 125, pp. 5139-5151.

(Continued)

*Primary Examiner* — Paul A Zucker
(74) *Attorney, Agent, or Firm* — Oblon, Spivak, McClelland, Maier & Neustadt, L.L.P.

(57) ABSTRACT

The present invention provides a method for producing asymmetrical mono-substituted alkylated compounds of α-amino acids that are represented by a specific formula, using an aldimine-type Schiff base. In the method of the present invention, the process of alkylating an aldimine-type Schiff base in a medium in the presence of an optically-active quaternary ammonium salt phase-transfer catalyst and an inorganic base is initiated, and subsequently the reaction is quenched at a time earlier than a time for completion of the stoichiometric reaction of the alkylation reaction, so that a mono-substituted alkylated product with high optical purity can be obtained.

10 Claims, No Drawings

(56) References Cited

OTHER PUBLICATIONS

Andrew P. Abbott, et al., "Electrochemical recognition of analytes using quaternary ammonium binaphthyl salts", Database CA [Online], Chemical Abstracts Service, XP002532001, Database accession No. 2003:168090.

Donald D. Fitts, et al., "Configurational studies in the biphenyl series. IV. Conformation and optical rotation of restricted biphenyls. Configurational correlation of biaryls by optical displacement. The absolute configuration of restricted 1,1'-binaphthyls", Database CA [Online], Chemical Abstracts Service, XP002532002, Database accession No. 1958 : 55790.

Shi Min, et al., "Synthesis of axially dissymmetric chiral ammonium salts by quaternization of secondary amines with (R)-(+)- 2,2' -bis (bromomethyl)-6,6' -dinitro biphenyl and (R) -(+)-2,2' -bis (bromomethyl)-1,1' -binaphthyl and an examination of their abillities as chiral phase-transfer catalysts", Database CA [Online}, Chemical Abstracts Service, XP002532003, retrieved from STN, Database accession No. 1995:419364.

Database Crossfire Beilstein, Beilstein Institut Zur Foerderung Der Chomischen Wissenchaften, Database accession No. 4927823, XP002532004.

Otto Th. Schmidt, et al., "Optisch Aktive 2, 3, 4, 2', 3', 4'-Hexamethoxy-Diphenyldicarbonsaure-6, 6' XIII. Mitteilung Über Natürliche Gerbstoffe", Ann Chem. vol. 576, No. 85, Feb. 18, 1952, pp. 85-93 (English translation of p. 87, line 14 to end of p. 89).

Andrew P. Abbott, et al., "Electrochemical recognition of charged species using quaternary ammonium binaphthyl salts", Analyst, vol. 126, 2001, 1892-1896.

Bruno Bellier, et al., "Synthesis and Biological Properties of New Constrained CCK-B Antagonists: Discrimination of Two Affinity States of the CCK-B Receptor on Transfected CHO Cells", J. Med. Chem., vol. 40, 1997, 3947-3956.

Frédéric Cottineau, et al., "Reductive Cleavage of Axially Disymmetric Tertiary Amines and Quaternary Ammonium Salts by Lithium Aluminium Hydride. Synthesis of New 1,1'-Binaphthyl Substituted Amines", Tetrahedron Letters, vol. 26, No. 4, 1985, pp. 421-424.

Lorenzo Di Bari, et al., "Conformational Study of 2,2'-Homosubstituted 1,1'-Binaphthyls by Means of UV and CD Spectroscopy", J. Am. Chem. Soc., vol. 121, 1999, pp. 7998-8004.

Masaya Ikunaka, et al., "A Scalable Synthesis of (R)-3,5-Dihydro-4H-dinaphth[2,1-c:1'2'-e]azepine", Organic Process Research & Development, vol. 7, 2003, pp. 644-648.

Taichi Kano, et al., "Design of new polyamine-based chiral phase-transfer catalysts for the enantioselective synthesis of phenylalanine", Tetrahedron: Asymmetry, vol. 15, 2004, pp. 1243-1245.

Masanori Kitamura, et al., "Powerful Chiral Phase-Transfer Catalysts for the Asymmetric Synthesis of α-Alkyl- and α,α-Dialkyl-α-amino Acids", Angewandte Chemie, vol. 44, 2005, pp. 1549-1551.

S. F. Mason, et al., "Optical Activity in the Biaryl Series", Tetrahedron, vol. 30, 1974, pp. 1671-1682.

Eric Mossel, et al., "Aspartame dipeptide analogues: effect of number of side-chain methylene group spacers and $C^{\alpha}$-methylation in the second position", Tetrahedron: Asymmetry, vol. 8, No. 8, 1997, pp. 1305-1314.

Takashi Ooi, et al., "Molecular Design of a $C_2$-Symmetric Chiral Phase-Transfer Catalyst for Practical Asymmetric Synthesis of α-Amino Acids", J. Am. Chem. Soc., vol. 121, 1999, pp. 6519-6520.

Min Shi, et al., "Synthesis of Axially Dissymmetric Chiral Ammonium Salts by Quaternization of Secondary Amines with (R)-(+)-2,2'-Bis(bromomethyl)-6,6'-dinitrobiphenyl and (R)-(+)-2,2'-Bis(bromomethyl)-1,1'-binaphthyl and an Examination of their Abilities as Chiral Phase-transfer Catalysts", J. Chem. Research (S), 1995, pp. 46-47.

Takayuki Shioiri, et al., "Asymmetric Phase Transfer Catalysis", Stimulating Concepts in Chemistry, 2000, pp. 123-143.

Irena G. Stara, et al., "Nucleophilic Cleavage of 4,5-Dihydro-3H-dinaphth[2,1-c:1',2'-e]azepinium Quaternary Salts. A Convenient Approach to New Axially Dissymmetric and Axially Asymmetric Ligands", J. Org. Chem., vol. 57, 1992, pp. 6966-6969.

Irena G. Stara, et al., "Optically Pure (S)- and (R)-4,5-Dihydro-3H-4-Methyldinaphth[2,1-c;1',2'-e]Azepines. Application to the Synthesis of new Bidentate Ligands with Axial Asymmetry", Tetrahedron: Asymmetry, vol. 3, No. 11, 1992, pp. 1365-1368.

Irena G. Stara, et al., "Stereochemical Dichotomy in the Stevens Rearrangement of Axially Twisted Dihydroazepinium and Dihydrothiepinium Salts. A Novel Enantioselective Synthesis of Pentahelicene", J. Am. Chem. Soc., vol. 116, 1994, pp. 5084-5088.

Irene G. Stara, et al., "Nucleophilic Attack on 4,5-Dihydro-4-alkyl-3H-dinaphtho[2,1-c:1',2'-e]thiepinium Salts. A Convenient Approach to New 2,2'-Bidentate 1,1'-Binaphthalene Ligands with Sulfur Donor Atoms", J. Org. Chem., vol. 59, 1994, pp. 1326-1332.

Shakti R. Ahmed, et al., "Steric effects in 2,2'-bridged biphenyls with a heterocyclic bridging ring. I. Optically active dihydrodibenzazepines", Chemical Abstract 53:2119. OREF 53: 405C-I, 406A, Journal of the Chemical Society, 1958, pp. 3043-3047.

Shakti R. Ahmed, et al., "Steric effects in 2,2'-bridged biphenyls with a heterocyclic bridging ring. III. Ultraviolet absorption spectra of some dihydrodibenzazepinium compounds.", Chemical Abstract 55:38083, OREF 55: 7430c-f, Journal of the Chemical Society, 1960, pp. 4165-4169.

G. H. Beaven, et al., "Relation between configuration and conjugation in diphenyl derivatives. I. The enantiomorphism and ultra-violet absorption spectra of some 2,2' bridged compounds.", Chemical Abstract 46:67079, OREF 46: 11211e-i, 11212a-I, Journal of Chemical Society, vol. 46, 1952, pp. 854-868.

Zhenfu Han, et al., "Convenient preparation of highly active phase-transfer catalyst for catalytic asymmetric synthesis of α-alkyl- and α-α-dialkyl-α-amino acids: application to the short asymmetric synthesis of BIRT-377", Tetrahedron Letters, vol. 46, 2005, pp. 8555-8558.

Joan M. Insole, et al., "Steric Effects of Methoxy-groups in 2,2'-Bridged Biphenyls. Part II", Journal of the Chemical Society. Perkin transactions 2: physical organic chemistry, No. 9, 1972, pp. 1168-1173.

Yoshiki Kashiwada, et al., "New Hexahydroxybiphenyl Derivatives as Inhibitors of Protein Kinase C", J. Med. Chem., vol. 37, No. 1, 1994, pp. 195-200.

Barry Lygo, et al., "Identification of a highly effective asymmetric phase-transfer catalyst derived from α-methylnaphtylamine" Tetrahedron Letters, vol. 44, No. 30, 2003, pp. 5629-5632.

Takashi Ooi, et al., "A New N-Spiro $C_2$-Symmetric Chiral Quaternary Ammonium Bromide Consisting of 4,6-Disubstituted Biphenyl Subunit as an Efficient Chiral Phase-Transfer Catalyst", Synlett, No. 12, 2003, pp. 1931-1933.

J.D. Reitze, et al., "The Further Chemistry of Ellagic Acid I. Synthesis of Tetramethylellagic Acid and Associated Polymer Precursors[1]", Holzforschung, vol. 55, No. 2, 2001, pp. 171-175.

A.M. Costero, et al., "Sistemas Macrociclicos Derivados De Bifenilos Sustituidos", Anales de Quimica, vol. 89, 1993, pp. 95-98 (with English Abstract).

Yong-Gang Wang, et al., "Convenient preparation of chiral phase-transfer catalysts with conformationally fixed biphenyl core for catalytic asymmetric synthesis of α-alkyl- and α,α-dialkyl-α-amino acids: application to the short asymmetric synthesis of BIRT-377", Tetrahedron, vol. 63, 2007, pp. 6042-6050 (with an additional page).

Yong-Gang Wang, et al., "Design of Chiral Phase Transfer Catalyst with Conformationally Fixed Biphenyl Core: Application to Asymmetric Alkylation of Glycine Derivatives", Organic Process Research & Development, vol. 11, 2007, pp. 628-632 (with an additional page).

U.S. Appl. No. 13/039,645, filed Mar. 3, 2011, Maruoka.

Frank R. Hewgill et al. "Phenanthrene-4,5-quinones: a Synthesis of Morphenol", J. Chem. Soc., Issue 6, 1988, pp. 1305-1311.

Theodora W. Greene, "Protective Groups in Organic Synthesis", John Wiley & Sons, 1981, pp. 168-169.

U.S. Appl. No. 13/338,301, filed Dec. 28, 2011, Maruoka, et al.
U.S. Appl. No. 13/338,313, filed Dec. 28, 2011, Maruoka, et al.
U.S. Appl. No. 13/338,601, filed Dec. 28, 2011, Maruoka, et al.
U.S. Appl. No. 13/338,659, filed Dec. 28, 2011, Maruoka, et al.
U.S. Appl. No. 13/337,658, filed Dec. 27, 2011, Maruoka, et al.

* cited by examiner

US 8,722,919 B2

PROCESS FOR PRODUCTION OF MONO-SUBSTITUTED ALKYLATED COMPOUND USING ALDIMINE OR DERIVATIVE THEREOF

TECHNICAL FIELD

The present invention relates to methods for producing mono-substituted alkylated compounds of α-amino acids using aldimine or a derivative thereof.

BACKGROUND ART

α-Amino acids have significant biochemical importance, and are frequently used as a raw material for drugs such as antibiotics, antineoplastic agents, and enzyme inhibitors. There are natural and non-naturally occurring α-amino acids, and many useful α-amino acids of both types have been found. In recent years, there have been a series of discoveries of non-naturally occurring, beneficial physiologically active amino acids such as L-dopa and L-azatyrosine, and there is a need for research into the practical asymmetrical synthesis of such optically-active α-amino acids.

One option for the practical asymmetrical synthesis of optically-active α-amino acids is asymmetrical mono-substitution alkylation. In conventional practice, it has been common to use a ketimine-type Schiff base for asymmetrical mono-substitution alkylation (O'Donnell, M. J. et al., *J. Am. Chem. Soc.*, 1989, vol. 111, p. 2353). Ketimine-type Schiff bases are complex to manufacture and thus generally are expensive. This has caused α-amino acids that are produced by asymmetrical mono-substitution alkylation to be expensive as well.

The reason why ketimine-type Schiff bases are used shall be explained based on the characteristics of ketimine-type Schiff bases that contribute to the reaction. Schiff bases include ketimine-type Schiff bases and aldimine-type Schiff bases, for example. In general, it is strongly believed that aldimine-type Schiff bases result in a racemization of the product because there is almost no pKa difference between the secondary hydrogen and the tertiary hydrogen, whereas ketimine-type Schiff bases inhibit racemization of the product obtained because this difference is large (O'Donnell, M. J., *Aldrichim. Acta.*, 2001, vol. 34, p. 3, and Maruoka, K. and Ooi, T., *Chemical Reviews*, 2003, vol. 103, p. 3013).

Thus, in this technical field, based on the presumption that ketimine-type Schiff bases will be used in consideration of the overall production efficiency, even though production costs are somewhat higher, attention has been focused on optimizing the methods for asymmetrical synthesis of optically-active α-amino acids using ketimine-type Schiff bases.

Ketimine-type pKa (Ha)

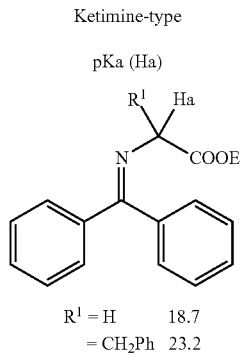

$R^1 = H$   18.7
  $= CH_2Ph$   23.2

Aldimine-type pKa (Ha)

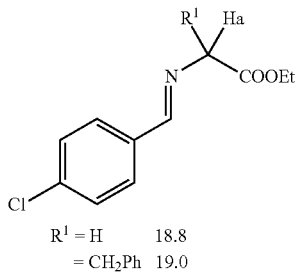

$R^1 = H$   18.8
  $= CH_2Ph$   19.0

On the other hand, recently, there was a report of an example of asymmetrical synthesis using macromolecular aldimine (Park, H.-G. et al., *J. Org. Chem.*, 2005, vol. 70, p. 1904). However, this report pertains to asymmetrical synthesis using a compound obtained by binding aldimine to a macromolecule, and is quite different from the Schiff bases of the technical field.

DISCLOSURE OF INVENTION

It is an object of the present invention to provide a method for producing mono-substituted alkylated compounds that are useful for asymmetrical mono-substitution alkylation, which is one method of synthesizing α-amino acids, and that are less expensive.

The present invention provides method for stereoselectively producing a compound represented by the following formula (I):

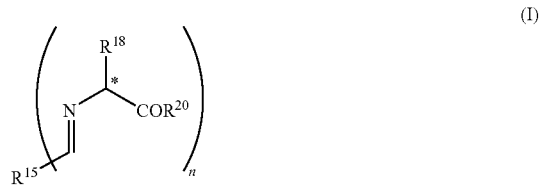

(I)

the method comprises:

initiating a reaction of a compound represented by the formula (II):

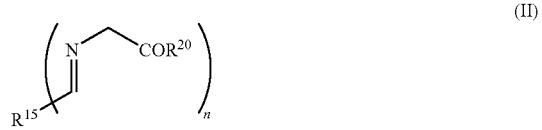

(II)

with a compound represented by the formula (III):

$R^{18}$—W   (III)

in a medium in the presence of an optically-active phase-transfer catalyst and an inorganic base; and quenching the reaction at a time earlier than a time for completion of a stoichiometric reaction of the compound represented by the formula (II) with the compound represented by the formula (III);

wherein in the formula (I) and the formula (II), $R^{15}$ is an aryl group or a heteroaryl group that may be substituted with at least one group selected from the group consisting of:

a $C_1$ to $C_8$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_8$ alkyl group that may be branched and that may be substituted with a halogen atom, or a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

$R^{20}$ is —$OR^{19}$ (where $R^{19}$ is a $C_1$ to $C_8$ alkyl group that may be substituted with a halogen atom or an aryl group that may be substituted with a halogen atom, and that may be branched or form a cyclic group) or —$NR^{50}R^{51}$ (where $R^{50}$ and $R^{51}$ are each independently a hydrogen atom, —$CHR^{28}R^{29}$ (where $R^{28}$ is a group selected from the group consisting of a hydrogen atom, and an aryl group that may be substituted with a $C_1$ to $C_4$ alkyl group that may be substituted with a halogen atom, a $C_1$ to $C_3$ alkoxy group that may be substituted with a halogen atom, or a halogen atom, and $R^{29}$ is an aryl group that may be substituted with a $C_1$ to $C_4$ alkyl group that may be substituted with a halogen atom, a $C_1$ to $C_3$ alkoxy group that may be substituted with a halogen atom, or a halogen atom) or —$OR^{101}$ (where $R^{101}$ is a $C_1$ to $C_8$ alkyl group or a benzyl group));

wherein in the formula (I) and the formula (III), $R^{18}$ is a group selected from the group consisting of:

(i) a $C_1$ to $C_{10}$ alkyl group that may be branched or form a cyclic group and that may be substituted with a halogen atom, wherein the alkyl group may be substituted with at least one group selected from the group consisting of:

a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), a halogen atom, —$COR^9$ (where $R^9$ is a $C_1$ to $C_4$ alkyl group that may be branched and that may be substituted with a halogen atom), and —$CO_2R^9$ (where $R^9$ is a $C_1$ to $C_4$ alkyl group that may be branched and that may be substituted with a halogen atom);

(ii) a $C_3$ to $C_{15}$ alkyl group or substituted allyl group that may be branched or form a cyclic group and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and the alkyl moiety of the aralkyl group is a $C_1$ to $C_6$ alkyl group that may be branched or form a cyclic group and that may be substituted with a halogen atom;

(vi) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR⁹ (where R⁹ is a $C_1$ to $C_4$ alkyl group that may be branched and that may be substituted with a halogen atom), and a halogen atom; and the alkyl moiety of the heteroaralkyl group is a $C_1$ to $C_6$ alkyl group that may be branched or form a cyclic group and that may be substituted with a halogen atom; and (vii) a $C_3$ to $C_9$ propargyl group or substituted propargyl group that may be branched and that may be substituted with a halogen atom;

wherein in the formula (III),

W is a functional group that has a leaving ability;

wherein in the formula (I) and the formula (II), n is an integer from 1 to 4; and wherein in the formula (I),

* shows a newly produced asymmetric center.

In one embodiment, the optically-active phase-transfer catalyst is an optically-active quaternary ammonium salt phase-transfer catalyst or a phase-transfer catalyst complexed with an optically-active metal atom.

In a further embodiment, the optically-active quaternary ammonium salt phase-transfer catalyst is an optically-active quaternary ammonium salt that has a biphenyl backbone and/or binaphthyl backbone, or an optically-active cinchona alkaloid quaternary ammonium salt.

In a further embodiment, the optically-active quaternary ammonium salt phase-transfer catalyst is an optically-active quaternary ammonium salt, or an enantiomer thereof, which is represented by:

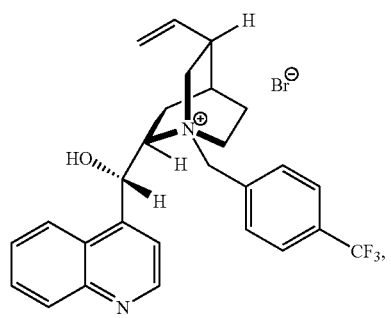

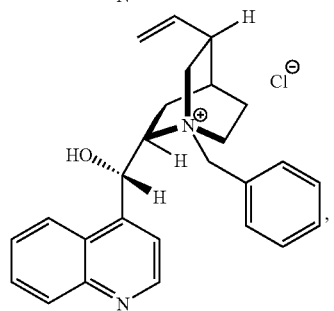

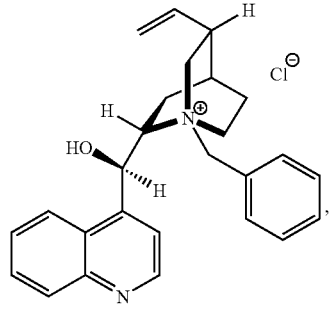

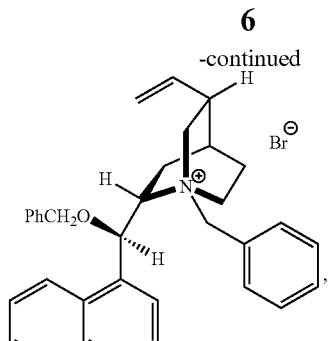

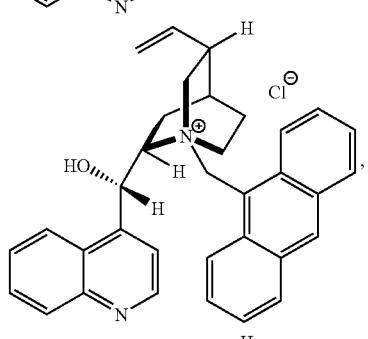

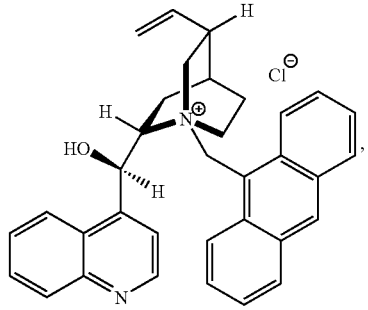

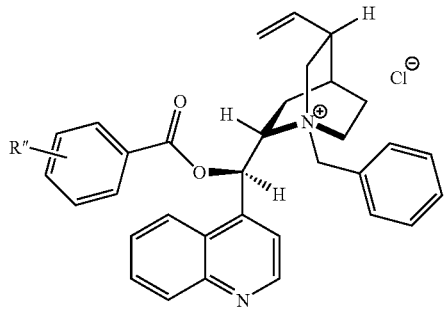

(where R″ is a hydrogen atom, a $C_1$ to $C_4$ alkyl group that may be branched, a $C_1$ to $C_5$ alkoxy group that may be branched, or a halogen atom),

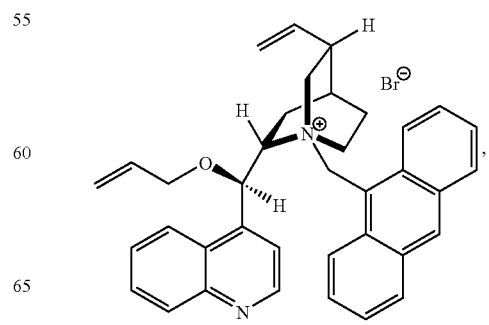

-continued
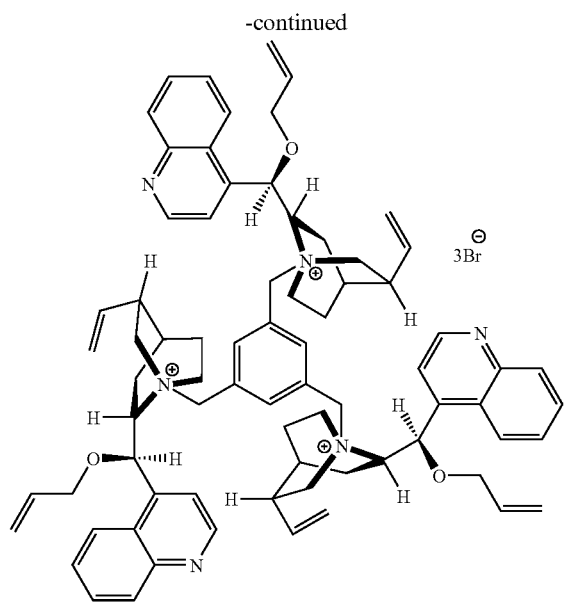
(where R is a hydrogen atom or an allyl group, and Z is Cl or Br),
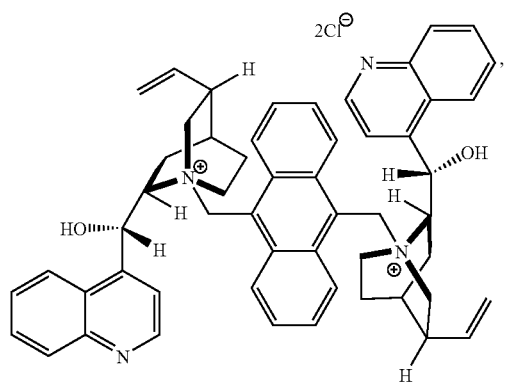
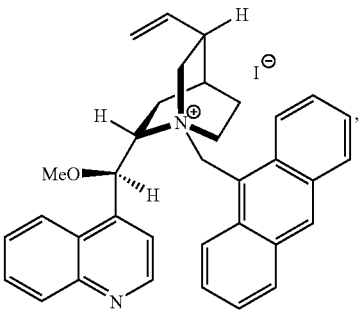
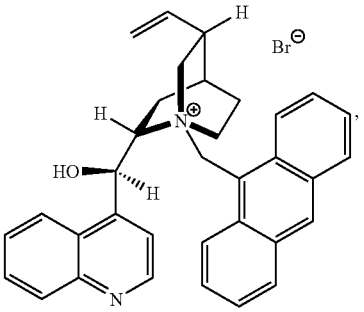
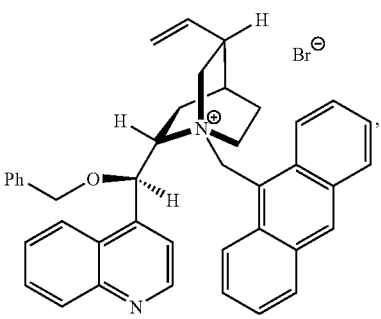
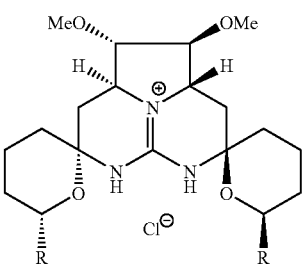
(where R is a methyl group or a hydrogen atom),
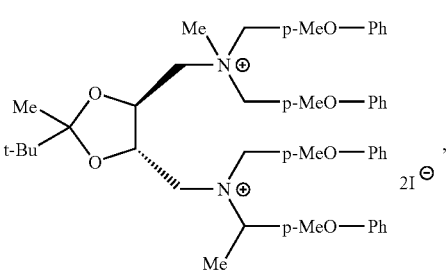

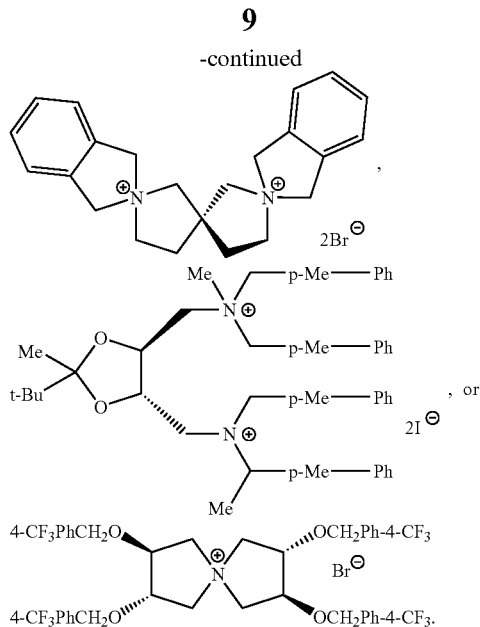

In a still further embodiment, the optically-active quaternary ammonium salt phase-transfer catalyst that has a biphenyl backbone and/or binaphthyl backbone is an optically-active quaternary ammonium salt represented by:

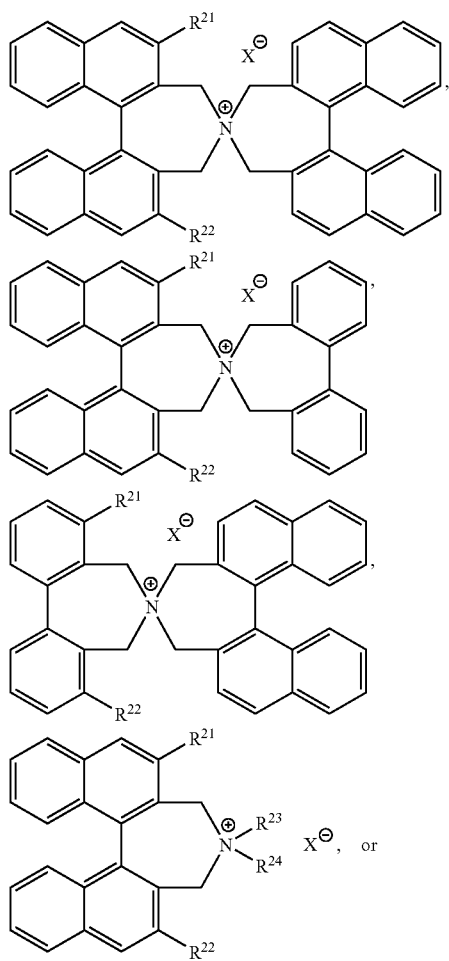

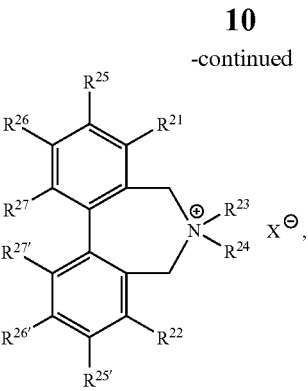

wherein
$R^{21}$ and $R^{22}$ are each independently a group selected from the group consisting of:
(i) a hydrogen atom;
(ii) —$NR^{30}R^{31}$ (where $R^{30}$ and $R^{31}$ are each independently a hydrogen atom or a $C_1$ to $C_4$ alkyl group that may be branched and that may be substituted with a halogen atom);
(iii) a cyano group;
(iv) a nitro group;
(v) a carbamoyl group;
(vi) an N—($C_1$ to $C_4$ alkyl)carbamoyl group;
(vii) an N,N-di($C_1$ to $C_4$ alkyl)carbamoyl group;
(viii) —$NHCOR^9$ (where $R^9$ is a $C_1$ to $C_4$ alkyl group that may be branched and that may be substituted with a halogen atom);
(ix) a halogen atom;
(x) a $C_1$ to $C_6$ alkyl group that may be branched or form a cyclic group and that may be substituted with a halogen atom;
(xi) a $C_2$ to $C_6$ alkenyl group that may be branched or form a cyclic group and that may be substituted with a halogen atom;
(xii) a $C_2$ to $C_6$ alkynyl group that may be branched or form a cyclic group and that may be substituted with a halogen atom;
(xiii) an aralkyl group, wherein the aryl moiety of the aralkyl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and a halogen atom;

(xiv) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(xv) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

or may be substituted with —O—$(CH_2)_p$—O— (where p is 1 or 2) at positions 3 and 4 that are taken together; and (xvi) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (xvii) —$S(O)_n$—R (where n is 0, 1, or 2, and R is a $C_1$ to $C_4$ alkyl group that may be branched and that may be substituted with a halogen atom);

$R^{25}$, $R^{25'}$, $R^{26}$, and $R^{26'}$ are each independently a group selected from the group consisting of:

(i) a hydrogen atom;

(ii) a halogen atom;

(iii) an alkyl group, wherein the alkyl group is a $C_1$ to $C_5$ alkyl group that may be substituted with a halogen atom and/or an aryl group, and/or that may be branched or form a cyclic group; and (iv) an alkoxy group, wherein the alkoxy group is a $C_1$ to $C_5$ alkoxy group that may be substituted with a halogen atom and/or an aryl group, and/or that may be branched or form a cyclic group;

$R^{27}$ and $R^{27'}$ are each independently a group selected from the group consisting of:

(i) a halogen atom;

(ii) an alkyl group, wherein the alkyl group is a $C_1$ to $C_5$ alkyl group that may be substituted with a halogen atom and/or an aryl group, and/or that may be branched or form a cyclic group; and (iii) an alkoxy group, wherein the alkoxy group is a $C_1$ to $C_5$ alkoxy group that may be substituted with a halogen atom and/or an aryl group, and/or that may be branched or form a cyclic group;

$R^{23}$ and $R^{24}$ are each independently a group selected from the group consisting of:

(i) a $C_1$ to $C_{30}$ alkyl group that may be branched or form a cyclic group and that may be substituted with a halogen atom;

(ii) a $C_2$ to $C_{12}$ alkenyl group that may be branched or form a cyclic group and that may be substituted with a halogen atom;

(iii) a $C_2$ to $C_{12}$ alkynyl group that may be branched or form a cyclic group and that may be substituted with a halogen atom;

(iv) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom,
a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(v) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom,
a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(vi) —$(CH_2)_n OCONR^{10}R^{11}$ (where $R^{10}$ and $R^{11}$ are each independently a group selected from the group consisting of:

(1) a hydrogen atom;

(2) a $C_1$ to $C_4$ alkyl group that may be branched and that may be substituted with a halogen atom;

(3) a $C_2$ to $C_6$ alkenyl group that may be branched or form a cyclic group and that may be substituted with a halogen atom;

(4) a $C_2$ to $C_6$ alkynyl group that may be branched or form a cyclic group and that may be substituted with a halogen atom;

(5) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom,
a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(6) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom,
a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(7) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom,
a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (8) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

and n is an integer from 1 to 12);

(vii) —$(CH_2)_n CONR^{12}R^{13}$ (where $R^{12}$ and $R^{13}$ are each independently a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

and n is an integer from 1 to 12);

(viii) —$(CH_2)_n NR^{12}COR^{13}$ (where $R^{12}$ and $R^{13}$ are each independently a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

and n is an integer from 1 to 12);

(ix) —$(CH_2)_nNR^{12}R^{13}$ (where $R^{12}$ and $R^{13}$ are each independently a group selected from the group consisting of:

(1) a hydrogen atom;

(2) a $C_1$ to $C_4$ alkyl group that may be branched;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

and n is an integer from 1 to 12);

(x) —$(CH_2)_nY$—$OR^{12}$ (where Y is a $C_1$ to $C_4$ divalent saturated hydrocarbon group that may be branched, and $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom,

19 a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be branched and that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be branched and that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);
(xi) —(CH$_2$)$_n$—OR$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:

20 a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be branched and that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be branched and that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);
(xii) —(CH$_2$)$_n$—S—R$^{12}$ (where R$^{12}$ is a group selected from the group consisting of:
(1) a hydrogen atom;
(2) a C$_1$ to C$_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

and n is an integer from 1 to 12);

(xiii) —$(CH_2)_n$—SO—$R^{12}$ (where $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom;
and n is an integer from 1 to 12); and
(xiv) —$(CH_2)_n$—$SO_2$—R$^{12}$ (where R$^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
(4) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom;
and n is an integer from 1 to 12); or
R$^{23}$ and R$^{24}$ are taken together to form a divalent group selected from the group consisting of:
—$(CH_2)_m$— (where m is an integer from 2 to 8);

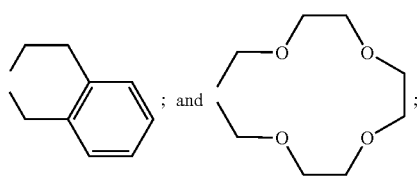

and

X$^-$ is a halide anion.

In a further embodiment, the phase-transfer catalyst complexed with an optically-active metal atom is a metal complex, or an enantiomer thereof, which is represented by:

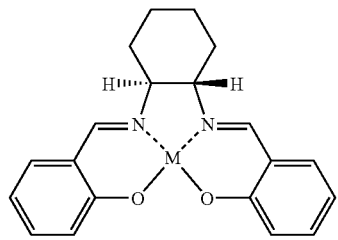

(where M is Ni or Cu).

In one embodiment, at the time earlier than a time for completion of the stoichiometric reaction, an optical purity of the compound represented by the formula (I) is 70% ee or more.

The present invention also provides method for stereoselectively producing a compound represented by the following formula (I):

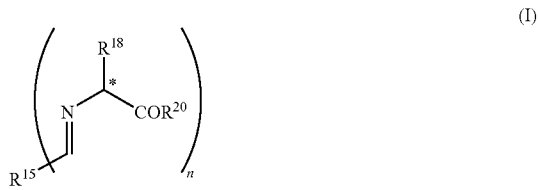

(I)

the method comprises:

initiating a reaction of a compound represented by the formula (II):

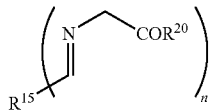

(II)

with a compound represented by the formula (III):

$R^{18}$—W  (III)

in a medium in the presence of an optically-active phase-transfer catalyst and an inorganic base; and quenching the reaction at a time t that satisfies the following inequality:

$$50 < \frac{A_t(\%\ ee) \times YLD_t(\%)}{100} < 100$$

(where $A_t$ is the optical purity (% ee) of the compound represented by the formula (I) that is obtained by quenching the reaction at a time t from the initiation of the reaction; and $YLD_t$ is the yield (%) of the compound represented by the formula (I) that is obtained by quenching the reaction at a time t from the initiation of the reaction);

wherein in the formula (I) and the formula (II), $R^{15}$ is an aryl group or a heteroaryl group that may be substituted with at least one group selected from the group consisting of:

a $C_1$ to $C_8$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_8$ alkyl group that may be branched and that may be substituted with a halogen atom, or a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

$R^{20}$ is —$OR^{19}$ (where $R^{19}$ is a $C_1$ to $C_8$ alkyl group that may be substituted with a halogen atom or an aryl group that may be substituted with a halogen atom, and that may be branched or form a cyclic group) or —$NR^{50}R^{51}$ (where $R^{50}$ and $R^{51}$ are each independently a hydrogen atom, —$CHR^{28}R^{29}$ (where $R^{28}$ is a group selected from the group consisting of a hydrogen atom, and an aryl group that may be substituted with a $C_1$ to $C_4$ alkyl group that may be substituted with a halogen atom, a $C_1$ to $C_3$ alkoxy group that may be substituted with a halogen atom, or a halogen atom, and $R^{29}$ is an aryl group that may be substituted with a $C_1$ to $C_4$ alkyl group that may be substituted with a halogen atom, a $C_1$ to $C_3$ alkoxy group that may be substituted with a halogen atom, or a halogen atom) or —$OR^{101}$ (where $R^{101}$ is a $C_1$ to $C_8$ alkyl group or a benzyl group));

in the formula (I) and the formula (III), $R^{18}$ is a group selected from the group consisting of:

(i) a $C_1$ to $C_{10}$ alkyl group that may be branched or form a cyclic group and that may be substituted with a halogen atom, wherein the alkyl group may be substituted with at least one group selected from the group consisting of a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), a halogen atom, —$COR^9$ (where $R^9$ is a $C_1$ to $C_4$ alkyl group that may be branched and that may be substituted with a halogen atom), and —$CO_2R^9$ (where $R^9$ is a $C_1$ to $C_4$ alkyl group that may be branched and that may be substituted with a halogen atom);

(ii) a $C_3$ to $C_{15}$ alkyl group or substituted allyl group that may be branched or form a cyclic group and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
the alkyl moiety of the aralkyl group is a $C_1$ to $C_6$ alkyl group that may be branched or form a cyclic group and that may be substituted with a halogen atom;
  (vi) a heteroaralkyl group having a heteroaryl moiety, wherein the heteroaryl moiety may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom,
a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
the alkyl moiety of the heteroaralkyl group is a $C_1$ to $C_6$ alkyl group that may be branched or form a cyclic group and that may be substituted with a halogen atom; and
  (vii) a $C_3$ to $C_9$ propargyl group or substituted propargyl group that may be branched and that may be substituted with a halogen atom;
in the formula (III),
  W is a functional group that has a leaving ability;
in the formula (I) and the formula (II),
  n is an integer from 1 to 4; and
in the formula (I),
  * shows a newly produced asymmetric center.
According to the present invention, it is possible to obtain a reaction product without allowing the effect of racemization to occur, even when an aldimine-type Schiff base is used. Thus, it is possible to less expensively provide an asymmetrical mono-substituted alkylated compound.

BEST MODE FOR CARRYING OUT THE INVENTION

Hereinafter, the terms used in the present invention will be defined.

The phrase "$C_1$ to $C_n$ alkyl group that may be branched or form a cyclic group" (where n is an integer) includes any linear alkyl group having 1 to n carbon atoms, any branched alkyl group having 3 to n carbon atoms, and any cyclic alkyl group having 3 to n carbon atoms. Examples of linear alkyl groups having 1 to 6 carbon atoms include methyl, ethyl, n-propyl, n-butyl, n-pentyl, and n-hexyl. Examples of branched alkyl groups having 3 to 6 carbon atoms include isopropyl, isobutyl, tert-butyl, and isopentyl. Examples of cyclic alkyl groups having 3 to 6 carbon atoms include cyclobutyl, cyclopentyl, and cyclohexyl. Furthermore, when "$C_1$ to $C_{12}$ alkyl group that may be branched or form a cyclic group and may be substituted with a halogen atom" is referred to, any linear alkyl group having 1 to 12 carbon atoms, any branched alkyl group having 3 to 12 carbon atoms, and any cyclic alkyl group having 3 to 12 carbon atoms are included, and a hydrogen atom at any position of these alkyl groups may be substituted with a halogen atom. Examples of such an alkyl group include n-heptyl, isoheptyl, n-octyl, isooctyl, n-decyl, and n-dodecyl.

In N—($C_1$ to $C_4$ alkyl) carbamoyl groups and N,N-di($C_1$ to $C_4$ alkyl) carbamoyl groups, "$C_1$ to $C_4$ alkyl" means $C_1$ to $C_4$ linear alkyl groups or $C_3$ to $C_4$ branched alkyl groups.

The phrase "$C_2$ to $C_n$ alkenyl group that may be branched or form a cyclic group" (where n is an integer) includes any linear alkenyl groups having 2 to n carbon atoms, any branched alkenyl groups having 3 to n carbon atoms, and any cyclic alkenyl groups having 3 to n carbon atoms. Examples of linear alkenyl groups having 2 to 6 carbon atoms include ethenyl, 1-propenyl, 2-propenyl, 1-butenyl, 2-butenyl, 1-pentenyl, 2-pentenyl, 3-pentenyl, 4-pentenyl, and 1-hexenyl. Examples of branched alkenyl groups having 3 to 6 carbon atoms include isopropenyl, 1-methyl-1-propenyl, 1-methyl-2-propenyl, 2-methyl-1-propenyl, 2-methyl-2-propenyl, and 1-methyl-2-butenyl. Examples of cyclic alkenyl groups having 3 to 6 carbon atoms include cyclobutenyl, cyclopentenyl, and cyclohexenyl. Furthermore, when "$C_2$ to $C_{12}$ alkenyl group that may be branched or form a cyclic group and may be substituted with a halogen atom" is referred to, any linear alkenyl groups having 2 to 12 carbon atoms, any branched alkenyl groups having 3 to 12 carbon atoms, and any cyclic alkenyl groups having 3 to 12 carbon atoms are included, and a hydrogen atom at any position of these alkenyl groups may be substituted with a halogen atom. Examples of such an alkenyl group include 1-heptenyl, 2-heptenyl, 1-octenyl, 1-decenyl, and 1-dodecenyl.

The phrase "$C_2$ to $C_n$ alkynyl group that may be branched or form a cyclic group" (where n is an integer) includes any linear alkynyl groups having 2 to n carbon atoms, any branched alkynyl groups having 3 to n carbon atoms, and any cyclic alkynyl groups having 3 to n carbon atoms. Examples of linear alkynyl groups having 2 to 6 carbon atoms include ethynyl, 1-propynyl, 2-propynyl, 1-butynyl, 2-butynyl, 1-pentynyl, and 1-hexynyl. Examples of branched alkynyl groups having 3 to 6 carbon atoms include 1-methyl-2-propynyl. Examples of cyclic alkynyl groups having 3 to 6 carbon atoms include cyclopropylethynyl, and cyclobutylethynyl. Furthermore, when "$C_2$ to $C_{12}$ alkynyl group that may be branched or form a cyclic group and may be substituted with a halogen atom" is referred to, any linear alkynyl groups having 1 to 12 carbon atoms, any branched alkynyl groups having 3 to 12 carbon atoms, and any cyclic alkynyl groups having 3 to 12 carbon atoms are included, and a hydrogen atom at any position of these alkynyl groups may be substituted with a halogen atom. Examples of such an alkynyl group include 1-heptynyl, 1-octynyl, 1-decynyl, and 1-dodecynyl.

The phrase "$C_1$ to $C_n$ alkoxy group that may be branched" (where n is an integer) includes alkoxy groups having any linear alkyl groups having 1 to n carbon atoms and alkoxy groups having any branched alkyl groups having 3 to n carbon atoms. Examples thereof include methyloxy, ethyloxy, n-propyloxy, isopropyloxy, and tert-butyloxy.

Examples of "aralkyl group" in the present invention include benzyl, phenethyl, and naphthylmethyl.

Examples of "heteroaralkyl group" in the present invention include pyridylmethyl, indolylmethyl, furylmethyl, thienylmethyl, and pyrrolylmethyl.

Examples of "aryl group" in the present invention include phenyl, naphthyl, anthryl and phenanthryl.

Examples of "heteroaryl group" in the present invention include pyridyl, pyrrolyl, imidazolyl, furyl, indolyl, benzothiophen-2-yl, thienyl, oxazolyl, thiazolyl, 3,4-methylenedioxyphenyl, 3,4-ethylenedioxyphenyl and tetrazolyl.

Examples of "halogen atom" in the present invention include a chlorine atom, a bromine atom, an iodine atom, and a fluorine atom. In the present invention, the term "halide anion" refers to halogen ions and examples thereof include a chloride ion, a bromide ion, an iodide ion and a fluoride ion.

In the present invention, the phrase "$C_3$ to $C_n$ allyl group or substituted allyl group that may be branched or form a cyclic group" (where n is an integer) refers to allyl groups or any substituted allyl groups having a substituent(s) at position 1 and/or 2 and/or 3 and having 4 to n carbon atoms in total, and for example, includes 2-butenyl, 1-cyclopentenylmethyl, and 3-methyl-2-butenyl.

In the present invention, the phrase "$C_3$ to $C_n$ propargyl group or substituted propargyl group that may be branched" (where n is an integer) refers to propargyl groups or any substituted propargyl groups having a substituent(s) at position 1 and/or 3 and having 4 to n carbon atoms in total, and for example, includes 2-butynyl, and 3-trimethylsilyl-2-propynyl.

In the present invention, the term "functional group having a leaving ability" means an atom or an atom group that leaves from a substrate in a substitution reaction or an elimination reaction, that is, a leaving group, and for example, includes a halogen atom, and a sulfonyloxy group.

In the present specification, the term "group (Q)" is used to simplify the description, for convenience, and is referred to the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom.

Hereinafter, the present invention will be described more specifically.

The present invention provides a method for producing an asymmetrical mono-substituted alkylated compound.

An example of the asymmetrical mono-substituted alkylated compound that can be produced with the present invention is represented by the following formula (I) below:

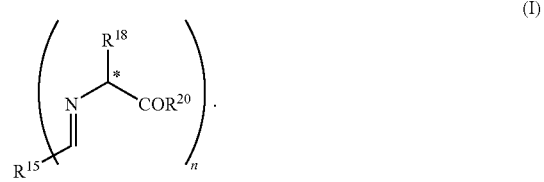

Here, $R^{15}$ is an aryl group or a heteroaryl group that may be substituted with at least one group selected from the group consisting of:

a $C_1$ to $C_8$ alkyl group that may be branched and that may be substituted with a halogen atom;

a $C_1$ to $C_5$ alkoxy group that may be branched and that may be substituted with a halogen atom;

an aryl group that may be substituted with a halogen atom, a $C_1$ to $C_8$ alkyl group that may be branched and that may be substituted with a halogen atom, or a $C_1$ to $C_5$ alkoxy group that may be branched and that may be substituted with a halogen atom;

a cyano group;

—$NR^{30}R^{31}$ (where $R^{30}$ and $R^{31}$ are each independently a hydrogen atom or a $C_1$ to $C_4$ alkyl group that may be substituted with a halogen atom);

a nitro group;

a carbamoyl group;

an N—($C_1$ to $C_4$ alkyl)carbamoyl group;

an N,N-di($C_1$ to $C_4$ alkyl)carbamoyl group;

—$NHCOR^9$ (where $R^9$ is a $C_1$ to $C_4$ alkyl group that may be branched and that may be substituted with a halogen atom); and a halogen atom;

$R^{20}$ is —$OR^{19}$ (where $R^{19}$ is a $C_1$ to $C_8$ alkyl group that may be substituted with a halogen atom or an aryl group that may be substituted with a halogen atom, and that may be branched or form a cyclic group) or —$NR^{50}R^{51}$ (where $R^{50}$ and $R^{51}$ are each independently a hydrogen atom, —$CHR^{28}R^{29}$ (where $R^{28}$ is a group selected from the group consisting of a hydrogen atom, and an aryl group that may be substituted with a $C_1$ to $C_4$ alkyl group that may be substituted with a halogen atom, a $C_1$ to $C_3$ alkoxy group that may be substituted with a halogen atom, and a halogen atom, and $R^{29}$ is an aryl group that may be substituted with a $C_1$ to $C_4$ alkyl group that may be substituted with a halogen atom, a $C_1$ to $C_3$ alkoxy group that may be substituted with a halogen atom, or a halogen atom) or —$OR^{101}$ (where $R^{101}$ is a $C_1$ to $C_8$ alkyl group or a benzyl group));

$R^{18}$ is a group selected from the group consisting of:

(i) a $C_1$ to $C_{10}$ alkyl group that may be branched or form a cyclic group and that may be substituted with a halogen atom, wherein the alkyl group may be substituted with at least one group selected from the group consisting of:

a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), a halogen atom, —$COR^9$ (where $R^9$ is a $C_1$ to $C_4$ alkyl group that may be branched and that may be substituted with a halogen atom), and —$CO_2R^9$ (where $R^9$ is a $C_1$ to $C_4$ alkyl group that may be branched and that may be substituted with a halogen atom);

(ii) a $C_3$ to $C_{15}$ alkyl group or substituted allyl group that may be branched or form a cyclic group and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group (Q), and the alkyl moiety of the aralkyl group is a $C_1$ to $C_6$ alkyl group that may be branched or form a cyclic group and that may be substituted with a halogen atom;

(vi) a heteroaralkyl group having a heteroaryl moiety, wherein the heteroaryl moiety may be substituted with at least one group selected from the group (Q), and the alkyl moiety of the aralkyl group is a $C_1$ to $C_6$ alkyl group that may be branched or form a cyclic group and that may be substituted with a halogen atom; and (vii) a $C_3$ to $C_9$ propargyl group or substituted propargyl group that may be branched and that may be substituted with a halogen atom;

n is an integer from 1 to 4; and

* shows a newly produced asymmetric center.

In the present invention, first, the compound of the formula (II) and the compound of the formula (III) are allowed to react in the presence of an optically-active phase-transfer catalyst and an inorganic base (hereinafter, this may be referred to as the alkylation process).

The compound of the formula (II) that is used in the present invention is an aldimine-type Schiff base or derivative thereof represented by the following formula (II):

$$\left( \underset{R^{15}}{\overset{N}{\diagdown}} \diagdown COR^{20} \right)_n \quad (II)$$

Here, $R^{15}$, $R^{20}$, and n are the same as defined for the above-described formula (I).

Examples of the compound of the formula (II) that is used in the present invention include benzaldehyde Schiff base of glycine ethyl ester, p-anisaldehyde Schiff base of glycine ethyl ester, p-chlorobenzaldehyde Schiff base of glycine ethyl ester, benzaldehyde Schiff base of glycine tert-butyl ester, p-chlorobenzaldehyde Schiff base of glycine tert-butyl ester, 2-methylbenzaldehyde Schiff base of glycine ethyl ester, p-methylbenzaldehyde Schiff base of glycine ethyl ester, 2-methylbenzaldehyde Schiff base of glycine tert-butyl ester, p-methylbenzaldehyde Schiff base of glycine tert-butyl ester, terephthalaldehyde Schiff base of glycine ethyl ester, and benzaldehyde Schiff base of glycine diphenylmethylamide.

The compound of the formula (II) that is used in the present invention can, for example, be produced by reacting a benzaldehyde derivative with glycine ester hydrochloride in the presence of triethylamine (see P. Bey and J. P. Vevert, Tetrahedron Lett., 1977, pp. 1455-1458).

The compound of the formula (III) that is used in the present invention is a compound that has a leaving group, and is represented by the following formula (III):

$$R^{18}-W \quad (III)$$

Here, $R^{18}$ is the same as defined for the above-described formula (I), and W is a functional group that has a leaving ability.

Examples of the compound of the formula (III) that is used in the present invention include benzyl bromide, p-methylbenzyl bromide, p-fluorobenzyl bromide, 1-bromomethyl naphthalene, cinnamyl bromide, iodoethane, allyl bromide, methallyl bromide, 2-iodobenzyl bromide, 3-iodobenzyl bromide, and p-iodobenzyl bromide.

The optically-active phase-transfer catalyst that is used in the present invention encompasses asymmetrical catalysts that can usefully function as a phase-transfer catalyst for producing an optically-active α-amino acid or derivative thereof. There are no particular limitations regarding such compounds, so long as they are optically-active phase-transfer catalysts that are known in the art, and specific examples thereof include phase-transfer catalysts complexed with optically-active metal atoms, and optically-active quaternary ammonium salts. Further examples include optically-active phase-transfer catalysts having a biphenyl backbone and/or binaphthyl backbone, and compounds known as optically-active cinchona alkaloid quaternary ammonium salts. One example of optically-active phase-transfer catalysts that can be used in the present invention includes a phase-transfer catalyst complexed with optically-active metal atom, and an enantiomer thereof, which is represented by:

(where M is Cu or Ni).

The above-described phase-transfer catalysts complexed with optically-active metal atoms are known, and the methods for producing them also are known (Maruoka, K. and Ooi, T., *Chemical Reviews*, 2003, vol. 103, p. 3013).

Alternatively, another example of an optically-active phase-transfer catalyst that can be used in the present invention is an optically-active cinchona alkaloid quaternary ammonium salt, and enantiomer thereof, which is represented by:

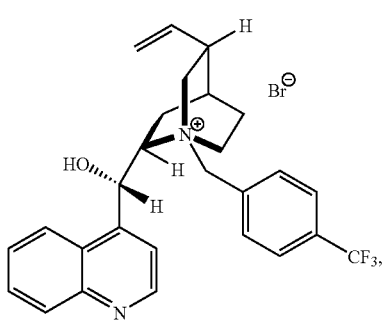
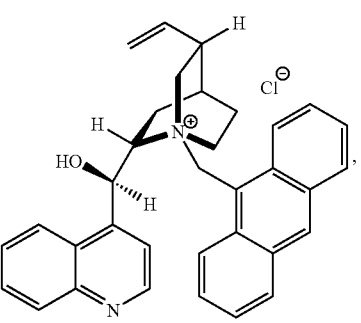
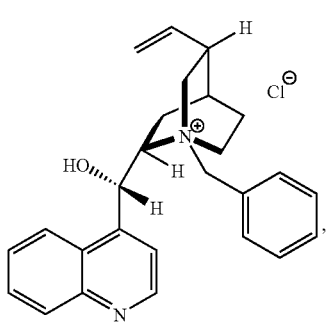
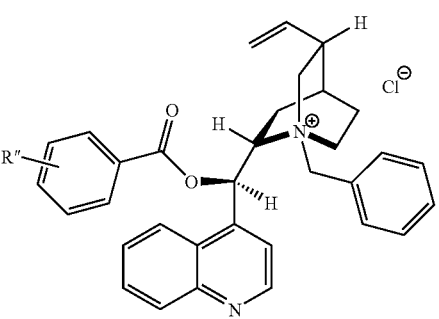
(where R'' is a hydrogen atom, a $C_1$ to $C_4$ alkyl group that may be branched, a $C_1$ to $C_5$ alkoxy group that may be branched, or a halogen atom),
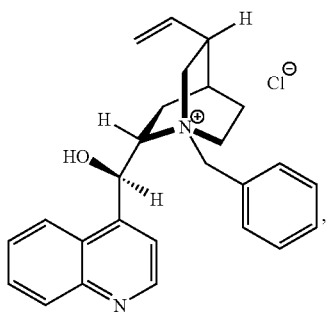
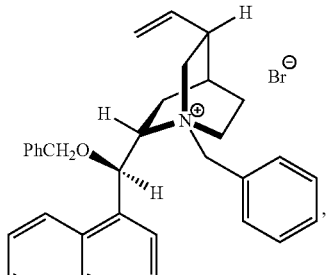
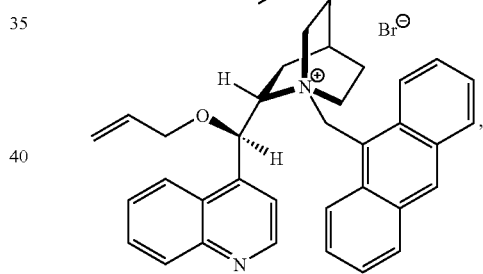
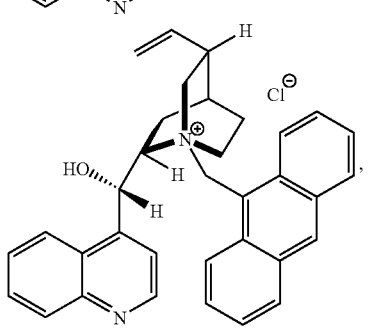

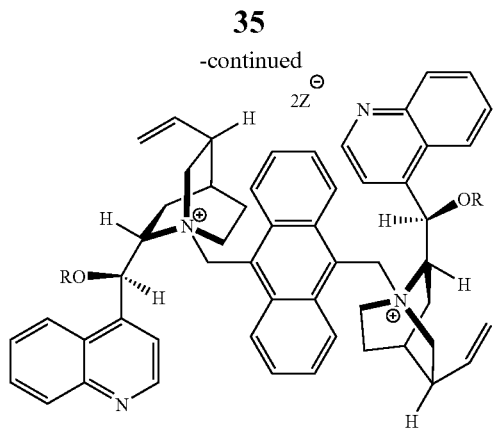

(where R is a hydrogen atom or an allyl group, and Z is Cl or Br),

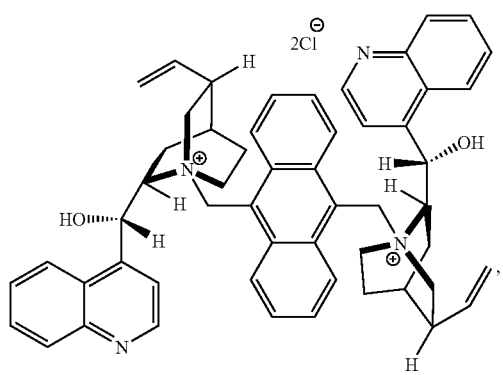

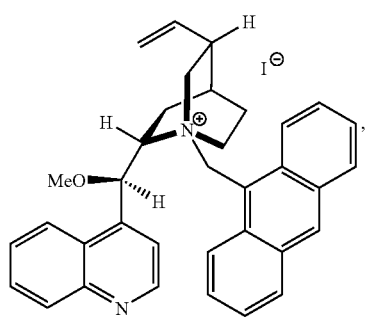

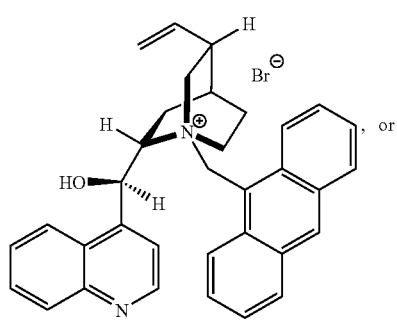

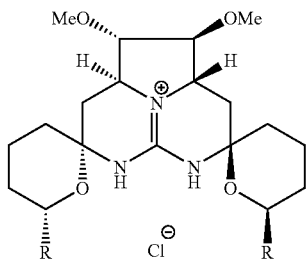

The above-described optically-active cinchona alkaloid quaternary ammonium salts are known, and the methods for producing them also are known (Maruoka, K. and Ooi, T., *Chemical Reviews*, 2003, vol. 103, p. 3013).

Alternatively, yet another example of an optically-active phase-transfer catalyst that can be used in the present invention is an optically-active quaternary ammonium salt, and enantiomer thereof, which is represented by:

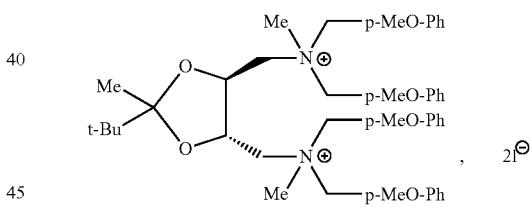

(where R is a methyl group or a hydrogen atom),

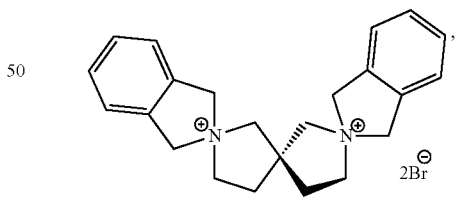

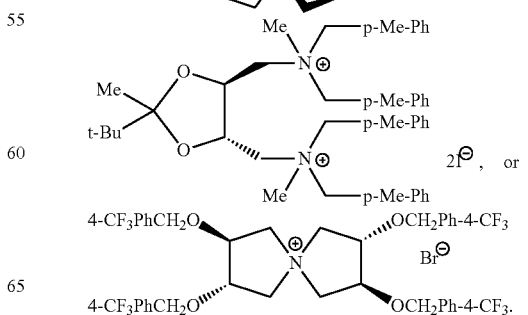

The above optically-active quaternary ammonium salts are known, and the methods for producing them also are known (Maruoka, K. and Ooi, T., *Chemical Reviews,* 2003, vol. 103, p. 3013).

Alternatively, yet another example of an optically-active phase-transfer catalyst that can be used in the present invention is an optically-active quaternary ammonium salt having a biphenyl backbone and/or binaphthyl backbone represented by:

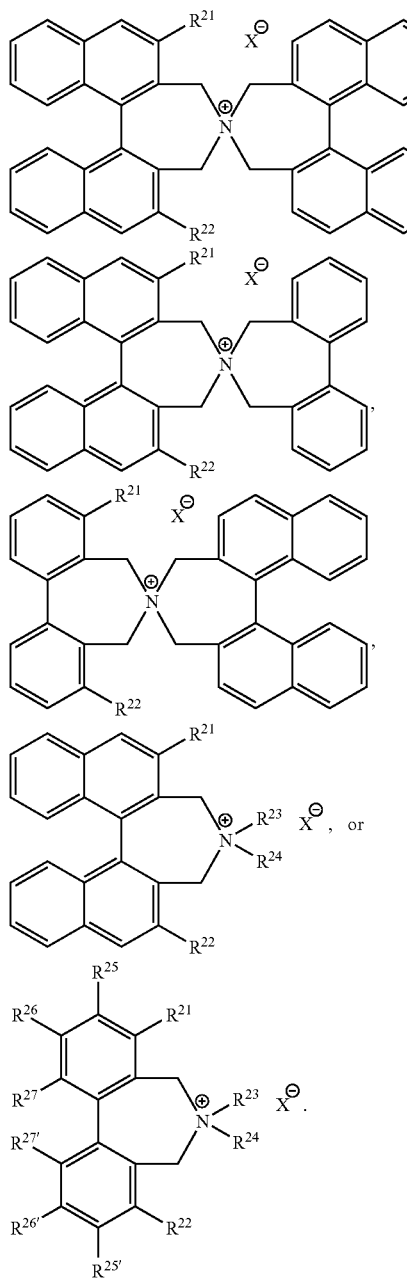

Here,
$R^{21}$ and $R^{22}$ are each independently a group selected from the group consisting of:
(i) a hydrogen atom;
(ii) —$NR^{30}R^{31}$ (where $R^{30}$ and $R^{31}$ are each independently a hydrogen atom or a $C_1$ to $C_4$ alkyl group that may be branched and that may be substituted with a halogen atom);
(iii) a cyano group;
(iv) a nitro group;
(v) a carbamoyl group;
(vi) an N—($C_1$ to $C_4$ alkyl)carbamoyl group;
(vii) an N,N-di($C_1$ to $C_4$ alkyl)carbamoyl group;
(viii) —$NHCOR^9$ (where $R^9$ is a $C_1$ to $C_4$ alkyl group that may be branched and that may be substituted with a halogen atom);
(ix) a halogen atom;
(x) a $C_1$ to $C_6$ alkyl group that may be branched or form a cyclic group and that may be substituted with a halogen atom;
(xi) a $C_2$ to $C_6$ alkenyl group that may be branched or form a cyclic group and that may be substituted with a halogen atom;
(xii) a $C_2$ to $C_6$ alkynyl group that may be branched or form a cyclic group and that may be substituted with a halogen atom;
(xiii) an aralkyl group, wherein the aryl moiety of the aralkyl group may be substituted with at least one group selected from the group (Q);
(xiv) a heteroaralkyl group having a heteroaryl moiety, wherein the heteroaryl moiety may be substituted with at least one group selected from the group (Q);
(xv) an aryl group, wherein the aryl group may be substituted with at least one group selected from the group (Q) or may be substituted with —O—$(CH_2)_p$—O— (where p is 1 or 2) at positions 3 and 4 that are taken together;
(xvi) a heteroaryl group, wherein the heteroaryl group may be substituted with at least one group selected from the group (Q); and
(xvii) —$S(O)_n$—R (where n is 0, 1, or 2, and R is a $C_1$ to $C_4$ alkyl group that may be branched and that may be substituted with a halogen atom);
$R^{25}$, $R^{25'}$, $R^{26}$, and $R^{26'}$ are each independently a group selected from the group consisting of:
(i) a hydrogen atom;
(ii) a halogen atom;
(iii) an alkyl group, wherein the alkyl group is a $C_1$ to $C_5$ alkyl group that may be substituted with a halogen atom and/or an aryl group, and/or that may be branched or form a cyclic group; and
(iv) an alkoxy group, wherein the alkoxy group is a $C_1$ to $C_5$ alkoxy group that may be substituted with a halogen atom and/or an aryl group, and/or that may be branched or form a cyclic group;
$R^{27}$ and $R^{27'}$ are each independently a group selected from the group consisting of:
(i) a halogen atom;
(ii) an alkyl group, wherein the alkyl group is a $C_1$ to $C_5$ alkyl group that may be substituted with a halogen atom and/or an aryl group, and/or that may be branched or form a cyclic group; and
(iii) an alkoxy group, wherein the alkoxy group is a $C_1$ to $C_5$ alkoxy group that may be substituted with a halogen atom and/or an aryl group, and/or that may be branched or form a cyclic group;
$R^{23}$ and $R^{24}$ are each independently a monovalent organic group, preferably a group selected from the group consisting of:
(i) a $C_1$ to $C_{30}$ alkyl group that may be branched or form a cyclic group and that may be substituted with a halogen atom;
(ii) a $C_2$ to $C_{12}$ alkenyl group that may be branched or form a cyclic group and that may be substituted with a halogen atom;
(iii) a $C_2$ to $C_{12}$ alkynyl group that may be branched or form a cyclic group and that may be substituted with a halogen atom;

(iv) an aryl group, wherein the aryl group may be substituted with at least one group selected from the group (Q);

(v) a heteroaryl group, wherein the heteroaryl group may be substituted with at least one group selected from the group (Q);

(vi) —$(CH_2)_n OCONR^{10}R^{11}$ (where $R^{10}$ and $R^{11}$ are each independently a group selected from the group consisting of:

(1) a hydrogen atom;

(2) a $C_1$ to $C_4$ alkyl group that may be branched and that may be substituted with a halogen atom;

(3) a $C_2$ to $C_6$ alkenyl group that may be branched or form a cyclic group and that may be substituted with a halogen atom;

(4) a $C_2$ to $C_6$ alkynyl group that may be branched or form a cyclic group and that may be substituted with a halogen atom;

(5) an aralkyl group, wherein the aryl moiety of the aralkyl group may be substituted with at least one group selected from the group (Q);

(6) a heteroaralkyl group having a heteroaryl moiety, wherein the heteroaryl moiety may be substituted with at least one group selected from the group (Q);

(7) an aryl group, wherein the aryl group may be substituted with at least one group selected from the group (Q); and (8) a heteroaryl group, wherein the heteroaryl group may be substituted with at least one group selected from the group (Q); and n is an integer from 1 to 12);

(vii) —$(CH_2)_n CONR^{12}R^{13}$ (where $R^{12}$ and $R^{13}$ are each independently a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12);

(viii) —$(CH_2)_n NR^{12}COR^{13}$ (where $R^{12}$ and $R^{13}$ are each independently a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12);

(ix) —$(CH_2)_n NR^{12}R^{13}$ (where $R^{12}$ and $R^{13}$ are each independently a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12);

(x) —$(CH_2)_n Y$—$OR^{12}$ (where Y is a $C_1$ to $C_4$ divalent saturated hydrocarbon group that may be branched, and $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12);

(xi) —$(CH_2)_n$—$OR^{12}$ (where $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12);

(xii) —$(CH_2)_n$—S—$R^{12}$ (where $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12);

(xiii) —$(CH_2)_n$—SO—$R^{12}$ (where $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12); and (xiv) —$(CH_2)_n$—$SO_2$—$R^{12}$ (where $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group (Q); and (4) a heteroaryl group, wherein the heteroaryl group may be substituted with at least one group selected from the group (Q); and n is an integer from 1 to 12); or $R^{23}$ and $R^{24}$ are taken together to form a divalent organic group, preferably representing a divalent group selected from the group consisting of:

—$(CH_2)_m$— (where m is an integer from 2 to 8);

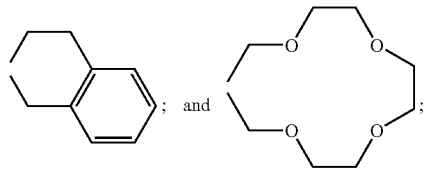

and $X^-$ is a halide anion.

It should be noted that in the present invention, if a quaternary ammonium salt having a biphenyl backbone and/or binaphthyl backbone represented by the following formula:

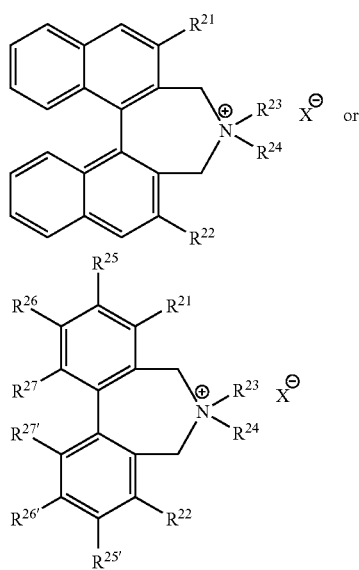

of the quaternary ammonium salts having a biphenyl backbone and/or binaphthyl backbone of the present invention, is used, then $R^{23}$ and $R^{24}$ are each independently a monovalent organic group, and preferably are a $C_1$ to $C_{12}$ alkyl group that may be branched or form a cyclic group and that may be substituted with a halogen atom, or a $C_{13}$ to $C_{30}$ alkyl group that may be branched or form a cyclic group and that may be substituted with a halogen atom.

In the present invention, the method for producing a quaternary ammonium phase-transfer catalyst that is represented by the following formula:

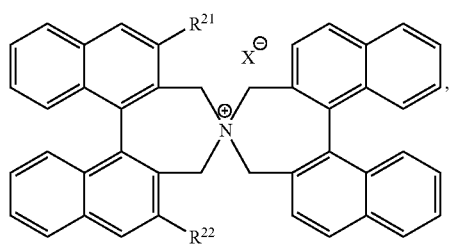

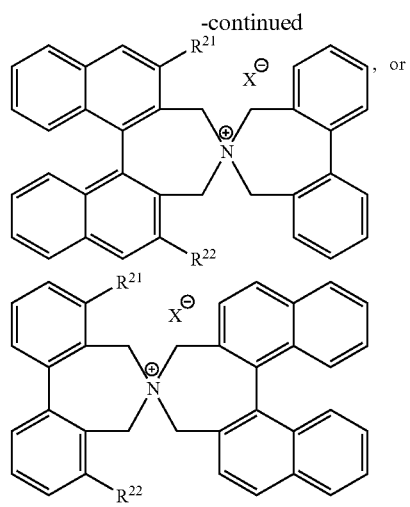

(where $R^{21}$, $R^{22}$, and X are the same as defined above) of the quaternary ammonium salts having a biphenyl backbone and/or binaphthyl backbone is well known (Japanese Laid-Open Patent Publication No. 2001-48866 and Japanese Laid-Open Patent Publication No. 2002-326992).

Alternatively, a quaternary ammonium phase-transfer catalyst that has a binaphthyl backbone that is represented by the following formula:

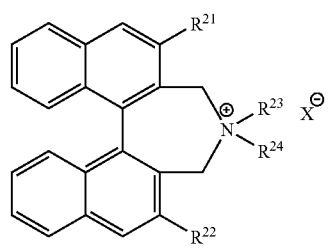

(where $R^{21}$, $R^{22}$, $R^{23}$, $R^{24}$, and X are the same as defined above) can be produced by, for example, reacting a binaphthyl compound represented by the following formula:

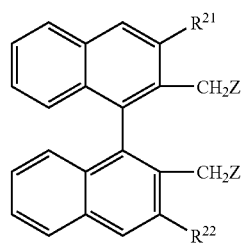

(where $R^{21}$ and $R^{22}$ are the same as defined above, and Z is a halogen atom) with a secondary amine represented by the following formula:

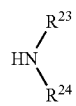

(where $R^{23}$ and $R^{24}$ are the same as defined above) in an organic solvent in the presence of an acid-scavenging agent.

The above binaphthyl compound can be easily prepared from, for example, easily available 1,1'-binaphthyl-2,2'-dicarboxylic acid (see Seki, M. et al., Synthesis, 2000, p. 1677) in a known process as described in the Scheme 1 below (see Ooi, T. et al., J. Org. Chem., 2003, vol. 68, p. 4576). The 1,1'-binaphthyl-2,2'-dicarboxylic acid may be either the (S)-form or the (R)-form.

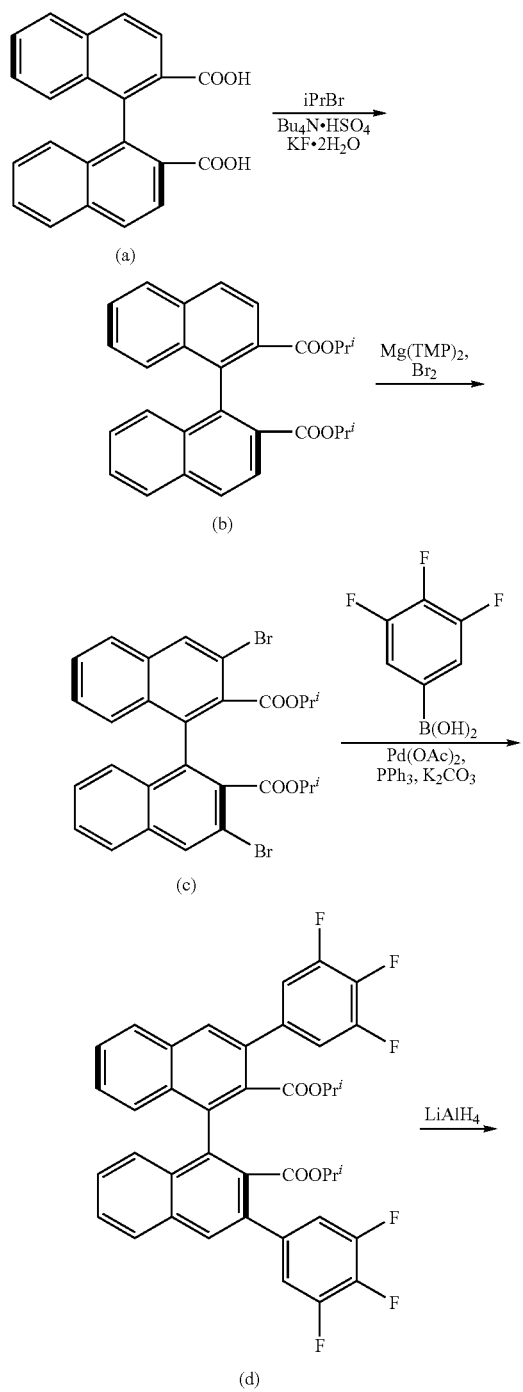

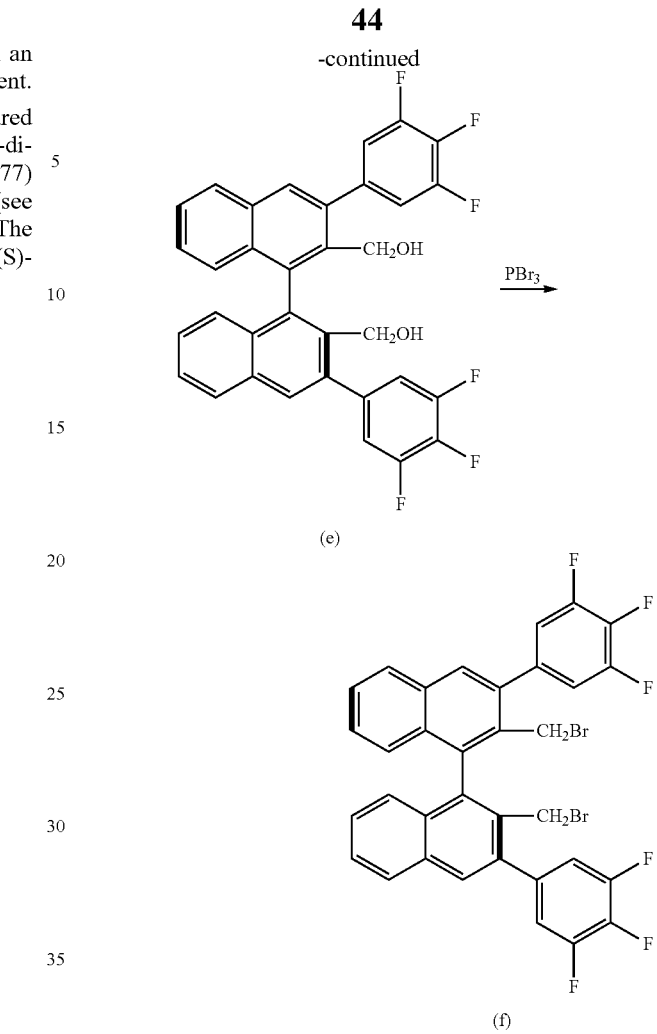

The following is a more specific explanation based on Scheme 1 above. First, the dicarboxylic acid (a) is converted to a corresponding diisopropyl ester (b) using isopropyl bromide, a catalyst $Bu_4N.HSO_4$, and $KF.2H_2O$. The obtained compound (b) is treated with magnesium bis(2,2,6,6-tetramethylpiperamide) (hereinafter, referred to as $Mg(TMP)_2$), and then $Br_2$ is added to obtain 3,3'-dibromo-1,1'-dinaphthyl-2,2'-dicarboxylic acid ester (c). Then, the obtained compound (c) and 3,4,5-trifluorophenylboronic acid are subjected to a Suzuki-Miyaura cross-coupling reaction in the presence of palladium acetate, triphenylphosphine, and potassium carbonate to give 3,3'-bis(3,4,5-trifluorophenyl)-1,1'-binaphthyl-2,2'-dicarboxylic acid ester (d). Furthermore, this compound (d) is reduced with $LiAlH_4$ to obtain alcohol (e) and the obtained alcohol (e) is treated with $PBr_3$, so that it is possible to obtain the dibromide (f) that corresponds to the above binaphthyl compound.

On the other hand, a large number of the secondary amines described above are commercially available and therefore can be obtained easily, so that it is possible to suitably select the secondary amine.

Examples of the organic solvent used include nitrile solvents (e.g., acetonitrile, propionitrile), ether solvents (e.g., dioxane, tetrahydrofuran, isopropyl ether, diethyl ether, dimethoxyethane, 2-methoxyethyl ether, cyclopentylmethyl ether), and alcohol solvents (e.g., methanol, ethanol, n-propanol, isopropanol, n-butanol, tert-butanol), and acetonitrile is particularly preferable. Examples of acid-scavenging agents include inorganic bases such as potassium carbonate, sodium carbonate, potassium hydrogencarbonate, and sodium hydrogencarbonate.

In the reaction, the secondary amine is preferably used in 0.5 to 4 equivalents, and more preferably 0.8 to 2 equivalents, with respect to the binaphthyl compound. The acid-scavenging agent is preferably used in 1 to 4 equivalents, and more preferably approximately 1 to 2 equivalents, with respect to the binaphthyl compound. The binaphthyl compound and the secondary amine are reacted in the presence of the acid-scavenging agent in an appropriate organic solvent with stirring. The reaction temperature is preferably between room temperature and the boiling point of the organic solvent, and more preferably the reaction is performed while heating under reflux. The reaction time is preferably 30 minutes to 24 hours, and more preferably 6 to 12 hours. In this case, the organic solvent is used in amounts at a ratio of volume (mL)/mass (g) of the binaphthyl compound the ratio is preferably 5 to 50 times, and more preferably 5 to 30 times. After the reaction is finished, the reaction mixture is extracted with dichloromethane, dichloroethane, or chloroform, for example, and isolated and purified by silica gel column chromatography, so that a binaphthyl-type quaternary ammonium salt can be obtained. Alternatively, the reaction mixture may be used as is as a phase-transfer catalyst in the method for producing a mono-substituted alkylated compound described in detail later.

Alternatively, a quaternary ammonium phase-transfer catalyst that has a biphenyl backbone, represented by the following formula:

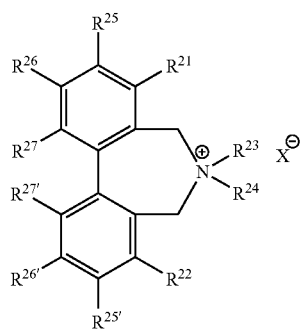

(where $R^{21}$, $R^{22}$, $R^{23}$, $R^{24}$, $R^{25}$, $R^{25'}$, $R^{26}$, $R^{26'}$, $R^{27}$, $R^{27'}$, and X are the same as defined above) can be produced by, for example, reacting a biphenyl compound represented by the following formula:

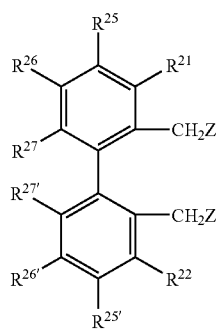

(where $R^{21}$, $R^{22}$, $R^{25}$, $R^{25'}$, $R^{26}$, $R^{26'}$, $R^{27}$, $R^{27'}$, and Z are the same as defined above) with a secondary amine represented by the following formula:

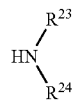

(where $R^{23}$ and $R^{24}$ are the same as defined above) in an organic solvent in the presence of an acid-scavenging agent.

The above biphenyl compound can be synthesized using the first method or the second method outlined below, for example.

The first method is shown in Scheme 2.

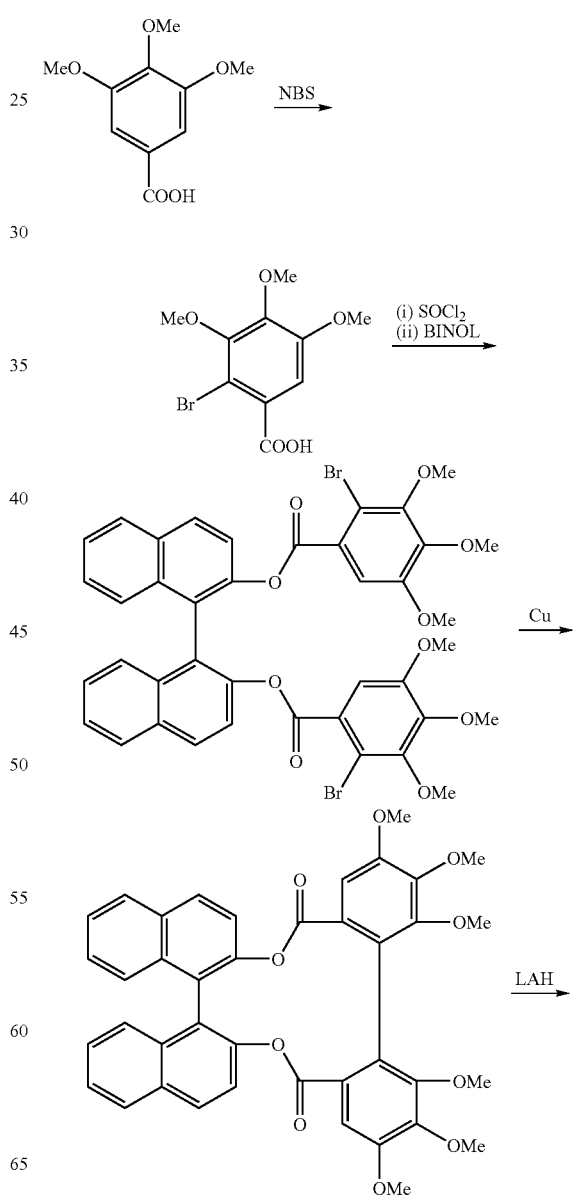

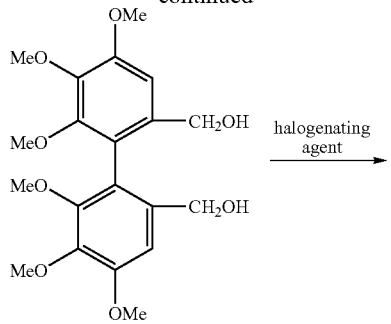

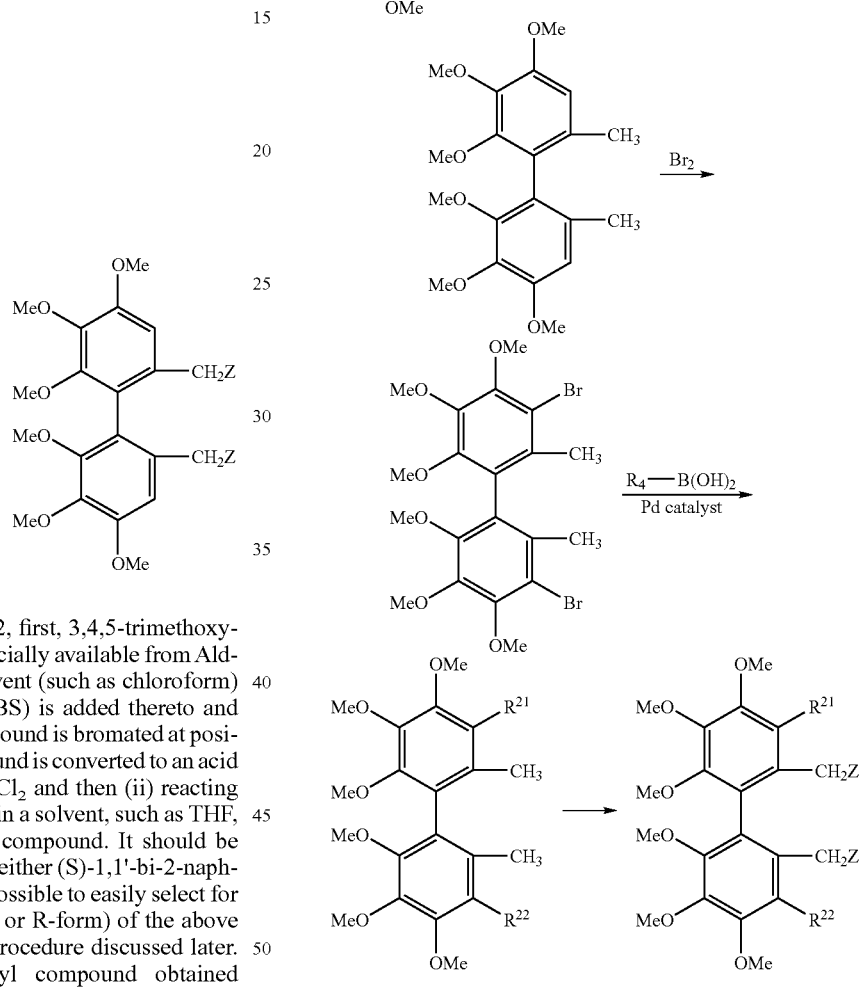

Scheme 3

Referring to the above Scheme 2, first, 3,4,5-trimethoxybenzoic acid (for example, commercially available from Aldrich) is dissolved in an organic solvent (such as chloroform) and then N-bromosuccinimide (NBS) is added thereto and heated under reflux. Thus, the compound is bromated at position 2. Next, the brominated compound is converted to an acid chloride by (i) reacting it with $SOCl_2$ and then (ii) reacting with (S)- or (R)-1,1'-bi-2-naphthol in a solvent, such as THF, to give a dibenzoyloxybinaphthyl compound. It should be noted that in this reaction, by using either (S)-1,1'-bi-2-naphthol or (R)-1,1'-bi-2-naphthol it is possible to easily select for the absolute configuration (S-form or R-form) of the above biphenyl compound, through the procedure discussed later. Then, the dibenzoyloxybinaphthyl compound obtained above is reacted with active copper powder suspended in an organic solvent (such as DMF) while heating under reflux to effect intramolecule coupling. The coupled compound is added to a THF suspension containing lithium aluminum hydride and the mixture was stirred for a predetermined time, so that it is possible to obtain a biphenyldimethanol compound. The biphenyldimethanol compound is reacted with a halogenating agent, such as phosphorus tribromide ($PBr_3$), to obtain the above biphenyl compound, in which $R^{21}$ and $R^{22}$ both are hydrogen atoms.

In the present invention, in order to obtain an above biphenyl compound in which $R^{21}$ and $R^{22}$ are groups other than a hydrogen atom, it is possible to produce the biphenyl compound through the procedure detailed in Scheme 3 below. It should be noted that for the sake of simplicity, a case in which $R^{21}$ and $R^{22}$ are identical is described.

Referring to the above Scheme 3, the obtained biphenyl compound is dehalogenated using means ordinarily used in the art. Then, the dehalogenated compound is dissolved in an organic solvent such as pyridine, and bromide is added thereto, so that it can be converted to a compound brominated at positions 5 and 5'. This compound is then subjected to the Suzuki-Miyaura coupling reaction with at least one type of boronic acid derivative represented by $R^{21}$—$B(OH)_2$ or $R^{22}$—$B(OH)_2$ (where $R^{21}$ and $R^{22}$ are each independently the same as the groups defined above) in an organic solvent such as THF and in the presence of a palladium catalyst. A specific example of the boronic acid derivative is 3,4,5-trifluorophenylboronic acid. The compound in which the bromine atoms at positions 5 and 5' have been substituted with an $R^{21}$ group or an $R^{22}$ group is produced. The obtained compound is finally halogenated by means ordinarily used in the art, so that it is possible to produce a biphenyl compound in which R²¹ (and/or R²²) is a group other than a hydrogen atom.

Next, a second method for synthesizing the biphenyl compound is described.

The second method uses a commercially available ellagic acid as a starting material. In other words, it is possible to obtain an optically active form of the dicarboxylic acid compound represented by the following formula:

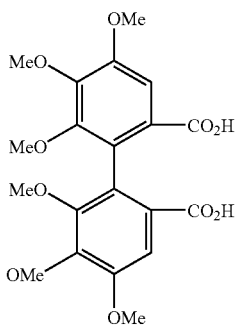 [SMILES: COc1cc(C(=O)O)c(-c2c(C(=O)O)cc(OC)c(OC)c2OC)c(OC)c1OC]

using the method of O. T. Schmidt et al. (O. T. Schmidt, K. Demmler, and Justus Liebigs, *Ann. Chem.*, 1952, vol. 576, p. 85) using this starting material. According to this method, it is possible to selectively produce either the S-form or the R-form of the dicarboxylic acid compound. The above biphenyl compound is then produced through the procedure detailed in Scheme 4 below. It should be noted that for the sake of simplicity, a case in which R²¹ and R²² are identical is described.

Scheme 4

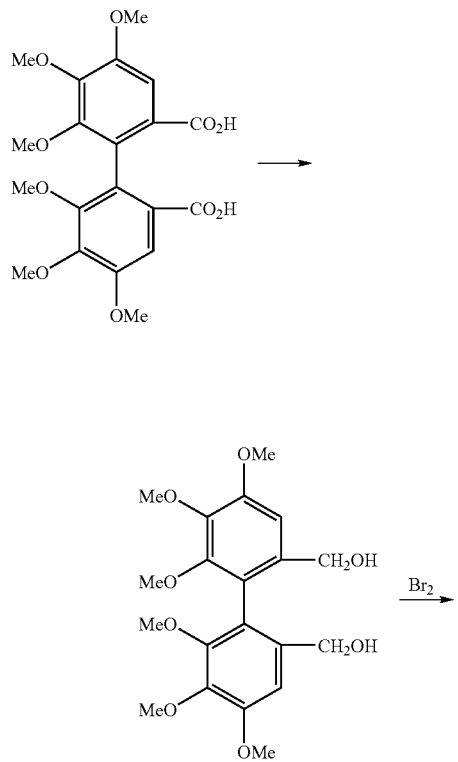

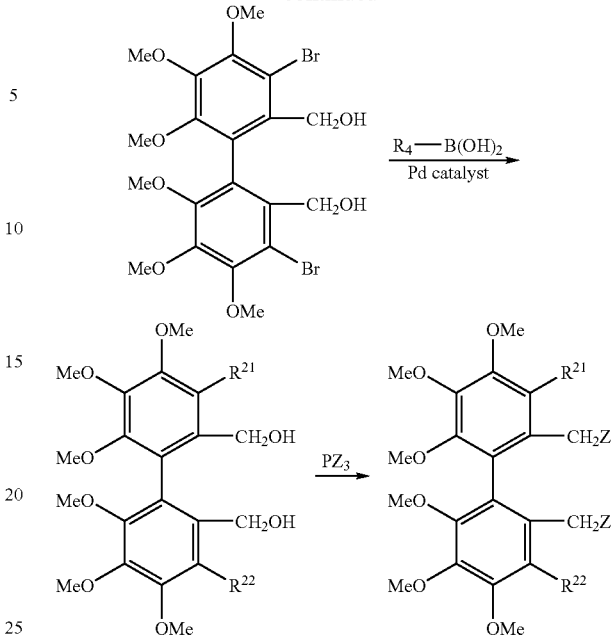

Referring to the above Scheme 4, the dicarboxylic acid moiety of the obtained dicarboxylic acid compound is converted to dimethanol in an organic solvent, such as THF, using $BH_3 \cdot Me_2S$. Next, this dimethanol compound is reacted with bromine in an organic solvent, such as pyridine, to produce a compound that is brominated at positions 5 and 5'. This compound is subjected to the Suzuki-Miyaura coupling reaction with at least one type of boronic acid derivative represented by $R^{21}$—$B(OH)_2$ or $R^{22}$—$B(OH)_2$ (where $R^{21}$ and $R^{22}$ are each independently the same as the groups defined above) in an organic solvent, such as THF, and in the presence of a palladium catalyst. A specific example of the boronic acid derivative is 3,4,5-trifluorophenylboronic acid. Thus, the dimethanol compound in which bromine atoms at positions 5 and 5' are substituted with an $R^{21}$ group or an $R^{22}$ group is produced. The obtained compound is finally reacted with a halogenating agent, such as phosphorus tribromide ($PBr_3$), so that it is possible to convert this to the above biphenyl compound, in which $R^{21}$ (and/or $R^{22}$) is a group other than a hydrogen atom.

The secondary amine used in the process for producing a quaternary ammonium phase-transfer catalyst having a biphenyl backbone is the same as that used in the process for producing a quaternary ammonium phase-transfer catalyst having a binaphthyl backbone discussed above.

The organic solvents used in the process for producing a quaternary ammonium phase-transfer catalyst having a biphenyl backbone by using the above biphenyl compound and the secondary amine are the same as in the case of the quaternary ammonium phase-transfer catalyst having a binaphthyl backbone, and include nitrile solvents (e.g., acetonitrile, propionitrile), ether solvents (e.g., dioxane, tetrahydrofuran, isopropyl ether, diethyl ether, dimethoxyethane, 2-methoxyethyl ether, and cyclopentylmethyl ether), and alcohol solvents (e.g., methanol, ethanol, n-propanol, isopropanol, n-butanol, and tert-butanol), and in particular, acetonitrile is preferable. Examples of acid-scavenging agents include inorganic bases such as potassium carbonate, sodium carbonate, potassium hydrogencarbonate, and sodium hydrogencarbonate.

In the reaction, the secondary amine is preferably used in 0.5 to 4 equivalents, and more preferably 0.8 to 2 equivalents, with respect to the biphenyl compound. The acid-scavenging agent is preferably used at 1 to 4 equivalents, and more preferably approximately 1 to 2 equivalents, with respect to the biphenyl compound. The biphenyl compound and the secondary amine are reacted in the presence of the acid-scavenging agent in an appropriate organic solvent with stirring. The reaction temperature is preferably between room temperature and the boiling point of the organic solvent, and more preferably the reaction is performed while heating under reflux. The reaction time is preferably 30 minutes to 24 hours, and more preferably 6 to 12 hours. In this case, the organic solvent is used in amounts at a ratio of volume (mL)/weight (g) of the biphenyl compound, the ratio is preferably 5 to 50 times, and more preferably 5 to 30 times. After the reaction is finished, the reaction mixture is extracted with dichloromethane, dichloroethane, or chloroform, for example, and isolated and purified by silica gel column chromatography, so that a quaternary ammonium salt having a biphenyl backbone can be obtained. Alternatively, the reaction mixture may be used as is as a phase-transfer catalyst in the method for producing a mono-substituted alkylated compound described in detail later.

Examples of the medium used in the alkylation process include benzene, toluene, xylene, ethyl ether, isopropyl ether, tetrahydrofuran, dioxane, methyl tert-butyl ether, and cyclopentyl methyl ether. Alternatively, the medium may also be a biphasic one containing water and a medium immiscible with water. The medium can be used in amounts at a ratio of volume (mL)/weight (g) of the compound of the formula (II), the ratio is preferably 0.5 to 50 times, and more preferably 1 to 30 times.

Examples of the inorganic base used in the alkylation process include lithium hydroxide, sodium hydroxide, potassium hydroxide, calcium hydroxide, rubidium hydroxide, and cesium hydroxide. The inorganic base can be used at preferably 0.5 to 20 equivalents, and more preferably 1 to 10 equivalents, with respect to the compound of the formula (II).

In the alkylation process, an inorganic base may be used in the form of an aqueous inorganic-base solution. In a case where an inorganic base is used in the form of an aqueous inorganic-base solution, the upper limit of the inorganic base that can be contained in the aqueous inorganic-base solution is preferably 100 equivalents or less, more preferably 60 equivalents or less, and even more preferably 30 equivalents or less, with respect to the compound of the formula (II). The lower limit of the inorganic base that can be contained in the aqueous inorganic-base solution is preferably 0.5 equivalents or more, and more preferably 0.8 equivalents or more, with respect to the compound of the formula (II). The aqueous inorganic-base solution can be used at preferably 20 w/w % to 70 w/w %, and more preferably 30 w/w % to 60 w/w %.

The volume ratio between the medium and the aqueous inorganic-base solution is a medium volume (mL)/inorganic base aqueous volume (mL) ratio of preferably 7/1 to 1/5, more preferably 5/1 to 1/3, and even more preferably 4/1 to 1/1.

In the alkylation process, the compound of the formula (III) is used at preferably 0.5 to 10 equivalents, and more preferably 0.8 to 5 equivalents, with respect to the compound of the formula (II). The optically-active phase-transfer catalyst is used as a catalyst preferably in amounts at a lower limit not less than 0.001 mol % and more preferably not less than 0.005 mol %, and at an upper limit of preferably not more than 5 mol %, and more preferably not more than 2 mol %, per mole of the compound of the formula (II).

In the alkylation process, in addition to the optically-active phase-transfer catalyst, an achiral quaternary ammonium salt, such as tetrabutyl ammonium bromide (TBAB), can be also used simultaneously. For example, TBAB functions as a cocatalyst in the alkylation process and improves the yield of an α-amino acid and its derivative obtained, and it also allows the amount of the optically-active phase-transfer catalyst that is used in the process to be reduced further.

Further, in the alkylation process, it is also possible to use an optically-active phase-transfer catalyst and crown ether compound, such as 18-crown-6 simultaneously. For example, 18-crown-6 functions as a cocatalyst in the alkylation process and improves the yield of an α-amino acid and its derivative obtained, and it also allows the amount of the optically-active phase-transfer catalyst that is used in the process to be reduced further.

The alkylation process is performed at a suitable temperature between −70° C. and room temperature, preferably −20° C. to 20° C., more preferably −10° C. to 5° C., in air, under a nitrogen atmosphere or under an argon atmosphere, and preferably under an argon atmosphere. The process can be performed with stirring.

When the aqueous inorganic-base solution is used in the alkylation process, it is for example preferable to perform the procedure as described below. That is, first, the compound of the formula (II), the optically-active phase-transfer catalyst, and the compound of the formula (III) are each added to the medium to prepare a mixture. At this time, it is preferable to sufficiently stir the mixture with cooling on ice or ice-salt, for example. This mixture is then cooled and the aqueous inorganic-base solution is added thereto, so that alkylation of the compound of the formula (II) is initiated. The temperatures set to cool the mixture are preferably between −20° C. and 20° C., more preferably between −15° C. and 10° C., and even more preferably between −10° C. and 5° C.

Thus, in the alkylation process initiated as described above, the reaction is then quenched at a time earlier than the time for completion of the stoichiometric reaction of the compound of the formula (II) with the compound of the formula (III), so that it becomes possible to stereoselectively produce the asymmetrical mono-substituted alkylated compound of the formula (I).

Here, the "time for completion of the stoichiometric reaction" of the compound of the formula (II) with the compound of the formula (III) is the time from the initiation of the chemical reaction to the completion of the chemical reaction without artificial interruption of the reaction, in other words, it refers to the time until either one of the two compounds disappears. The "time of disappearance" refers to the time until either one of the compound of the formula (II) or the compound of the formula (III) falls preferably 1%, more preferably 0.1%, and even more preferably 0.01%, in mole number below the mole number of the compound at the initiation of the reaction. This time can be easily measured by persons skilled in the art by, for example, measuring the starting amount of the reaction mixture over time directly or after hydrolysis of an aliquot of the reaction mixture, by analytical means well-known in the art, such as gas chromatography (GC) or high-performance liquid chromatography (HPLC). When the alkylation reaction is initiated in the alkylation process, the mono-substituted alkylated compound represented by the formula (I) is produced and its yield rises over time. At the early period of the reaction, a small amount of the mono-substituted alkylated compound has been produced, and its optical purity is extremely high. However, as the reaction progresses, the amount of mono-substituted alkylated compound produced increases, but the optical purity drops due to the progression of racemization. Accordingly, by quenching the reaction at a time earlier than the time for completion of the stoichiometric reaction, that is, before the progression of racemization, it is possible to obtain a mono-substituted alkylated compound with high optical purity in a certain degree of yield. In the present invention, at the time earlier than the time for completion of the stoichiometric reaction, it is preferable that the optical purity of the compound of the formula (I) is at least 70% ee.

Alternatively, in the present invention, the optically-active reaction product of interest may be obtained by quenching the reaction at an appropriate time that may even fall after the time for completion of the stoichiometric reaction, as long as it is before the start of gradual racemization of the reaction product. An appropriate time after the time for completion of the stoichiometric reaction refers to a time before the reaction product is influenced by racemization thereof. Such a time is preferably a time up until the optical purity of the compound of the formula (I) is found to have fallen below 70% ee, and more preferably a time up until it falls below 80% ee, when the optical purity of the reaction product in the reaction system is measured by analytical means well-known in the art, such as high-performance liquid chromatography (HPLC), after the stoichiometric reaction completion time has passed.

In this quenching process, the quenching is performed by adding water to the reaction mixture obtained by the alkylation process. The amount of water to be added is usually 0.1 to 10 times, and more preferably 0.5 to 3 times, the medium used in the alkylation process.

Alternatively, the alkylation initiated as described above may be quenched at a time t that satisfies the following inequality:

$$50 < \frac{A_t(\%\ ee) \times YLD_t(\%)}{100} < 100$$

(where $A_t$ is the optical purity (% ee) of the compound represented by the formula (I) that is obtained by quenching the reaction at a time t from the initiation of the reaction; and $YLD_t$ is the yield (%) of the compound represented by the formula (I) that is obtained by quenching the reaction at a time t from the initiation of the reaction). By quenching the reaction at this time t, it is possible to stereoselectively produce a mono-substituted alkylated compound.

According to the method of the present invention, it is possible to obtain an optically-active mono-substituted alkylated compound represented by the formula (I) at a high optical purity, even if an aldimine-type Schiff base is used. Here, high optical purity refers to preferably 70% ee or more, more preferably 80% ee or more, even more preferably 90% ee or more, and yet even more preferably 95% ee or more. The optical purity of the mono-substituted alkylated compound represented by the formula (I) can be measured by, for example, high-performance liquid chromatography (HPLC) directly or after hydrolysis.

The specific examples of the compound of the formula (I) that can be produced through the method of the present invention include:

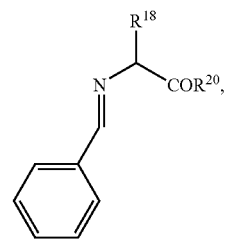

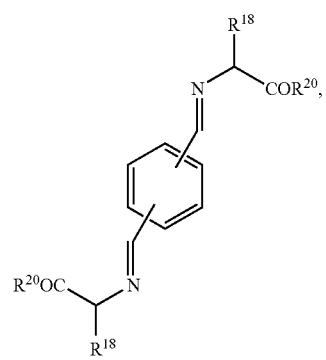

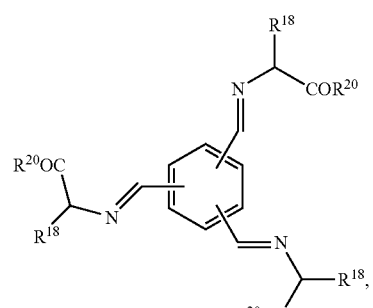

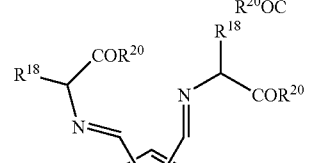

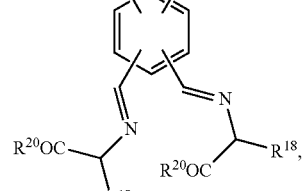

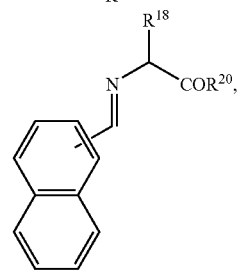

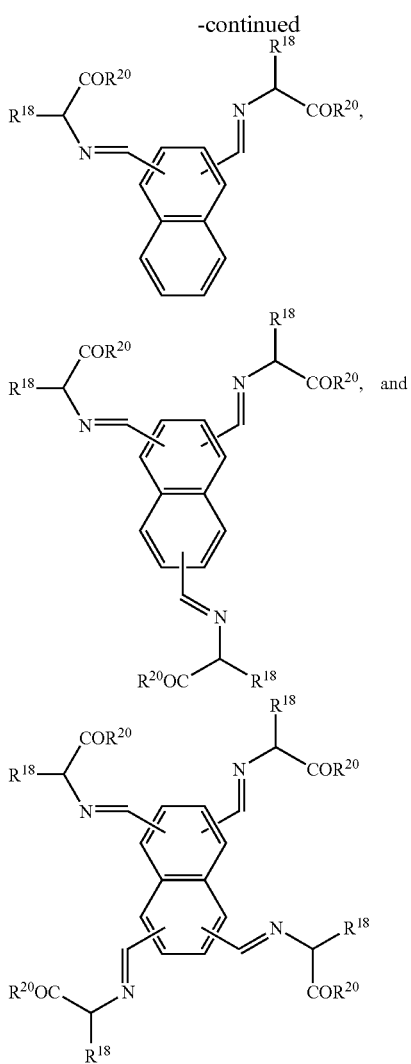

but the present invention is not particularly limited to these compounds.

In the present invention, it is possible to use the optically-active mono-substituted alkylated compound (optically-active α-amino acid derivative) represented by the formula (I) obtained through the above method to produce the optically-active α-amino acid represented by the following formula (IV):

$$\underset{H_2N}{\overset{R^{18}}{\underset{|}{\overset{*}{C}}}}COOH \qquad (IV)$$

for example, through any one of the following procedures.

First, the aldimino group ($R^{15}CH=N-$) moiety of the optically-active mono-substituted alkylated compound (optically-active α-amino acid derivative) represented by the formula (I) obtained through the above-described method is hydrolyzed under acidic conditions (aldimine acidic-hydrolysis process). Examples of the acid used in the aldimine acidic-hydrolysis process include inorganic acids (such as hydrochloric acid, sulfuric acid, and phosphoric acid) and organic acids (such as acetic acid, citric acid, and p-toluene-sulfonic acid). Specifically, this aldimine acidic-hydrolysis process proceeds by treating the mono-substituted alkylated compound at a suitable temperature (e.g., room temperature) with an aqueous solution of the acid, in a suitable medium (e.g., tetrahydrofuran, toluene, or ethanol). As a result, it is possible to obtain an ester derivative or an amide derivative of the amino acid, in which the terminal amino group has been freed, as an acidic-hydrolysis product.

Next, if necessary, the ester derivative or the amide derivative of the amino acid obtained as above (acidic-hydrolysis product) is subjected to hydrolysis under stronger acidic conditions than those under which the aldimine was hydrolyzed, or under basic conditions. Thus, it is possible to obtain a desired amino acid represented by the formula (IV) in which the terminal of the acidic-hydrolysis product (that is, the ester group or the amide group ($-COR^{20}$) of the acidic-hydrolysis product) has become a carboxylic acid.

EXAMPLES

Hereinafter, the present invention is described in specific detail by way of examples, but is not limited thereto.

In the following examples, unless described otherwise, the measurements were carried out under the following conditions: The $^1$H NMR spectrum was measured on the AVANCE-400 (400 MHz) by Bruker BIOSPIN. The optical purity of a reaction product was measured through high-performance liquid chromatography (HPLC) with a Waters 2690 using a 4.6 mm×25 cm Daicel Chiralcel OD, OD-H, AD or AD-H. Progression of the reaction was monitored with thin layer chromatography (TLC) using a Merck precoated TLC plate (silica gel 60 GF254, 0.25 mm).

Reference Example 1

Synthesis of Benzaldehyde Schiff Base of Glycine Ethyl Ester (Compound 3)

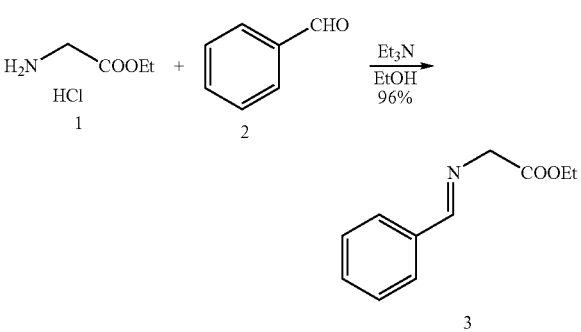

Glycine ethyl ester hydrochloride (compound 1) (34.9 g; 250 mmol) was added to ethanol (500 mL), then triethylamine (25.3 g; 250 mmol) was added thereto, and the mixture was stirred. Further, benzaldehyde (compound 2) (25.4 g; 244 mmol) dissolved in ethanol (500 mL) was added dropwise to the ethanol mixture of the compound 1. The reaction mixture was stirred at room temperature for two hours, and then the ethanol was removed under reduced pressure. Half-saturated saline (200 mL) was added to the residue, and this was extracted with ethyl acetate (150 mL×2) and the ethyl acetate layer was collected. The ethyl acetate layer was dried over sodium sulfate and then concentrated under reduced pressure to give the title compound 3 (46.0 g; slightly yellow oil, yield 96%). The NMR spectrum of the obtained compound 3 is shown in Table 1.

TABLE 1

NMR spectrum of compound 3

400 MHz $^1$H-NMR (CDCl$_3$): δ 8.21 (1H, s, CH=N), 7.77-7.70 (2H, m), 7.45-7.38 (3H, m), 4.41 (2H, s, N—CH$_2$—C), 4.24 (2H, q, J = 7.2 Hz, O—CH$_2$—C), 1.30 (3H, t, 7.2 Hz, C—CH$_3$)

Reference Example 2

Synthesis of p-anisaldehyde Schiff Base of Glycine Ethyl Ester (Compound 13)

Using p-anisaldehyde instead of benzaldehyde of Reference Example 1, the compound 13 (yield 89%) was prepared. The NMR spectrum of the obtained compound 13 is shown in Table 2.

TABLE 2

NMR spectrum of compound 13

400 MHz $^1$H-NMR (CDCl$_3$): δ 8.30 (1H, s, CH=N), 7.74-7.70 (2H, m), 6.95-6.92 (2H, m), 4.36 (2H, s, N—CH$_2$—C), 4.23 (2H, q, J = 7.2 Hz, O—CH$_2$—C), 3.82 (3H, s, O—CH$_3$), 1.30 (3H, t, 7.2 Hz, C—CH$_3$)

Reference Example 3

Synthesis of p-chlorobenzaldehyde Schiff Base of Glycine Ethyl Ester (Compound 15)

Using p-chlorobenzaldehyde instead of benzaldehyde of Reference Example 1, the compound 15 was prepared (yield 87%). The NMR spectrum of the obtained compound 15 is shown in Table 3.

TABLE 3

NMR spectrum of compound 15

400 MHz $^1$H-NMR (CDCl$_3$): δ 8.25 (1H, s, CH=N), 7.77-7.70 (2H, m), 7.45-7.38 (2H, m), 4.40 (2H, s, N—CH$_2$—C), 4.24 (2H, q, J = 7.2 Hz, O—CH$_2$—C), 1.30 (3H, t, 7.2 Hz, C—CH$_3$)

Reference Example 4

Synthesis of Benzaldehyde Schiff Base of Glycine tert-butyl Ester (Compound 9)

Using glycine tert-butyl ester hydrochloride instead of glycine ethyl ester hydrochloride of Reference Example 1, and using toluene as the solvent instead of ethanol, the compound 9 was prepared (quantitatively). The NMR spectrum of the obtained compound 9 is shown in Table 4.

TABLE 4

NMR spectrum of compound 9

400 MHz $^1$H-NMR (CDCl$_3$): δ 8.27 (1H, s, CH=N), 7.77-7.70 (2H, m), 7.45-7.38 (3H, m), 4.31 (2H, s, N—CH$_2$—C), 1.49 (9H, s, C—(CH$_3$)$_3$)

Reference Example 5

Synthesis of p-chlorobenzaldehyde Schiff Base of Glycine tert-butyl Ester (Compound 17)

Using glycine tert-butyl ester hydrochloride instead of glycine ethyl ester hydrochloride of Reference Example 1, and using p-chlorobenzaldehyde instead of benzaldehyde, the compound 17 was prepared (quantitatively). The NMR spectrum of the obtained compound 17 is shown in Table 5.

TABLE 5

NMR spectrum of compound 17

400 MHz $^1$H-NMR (CDCl$_3$): δ 8.22 (1H, s, CH=N), 7.74-7.71 (2H, m), 7.41-7.38 (2H, m), 4.31 (2H, s, N—CH$_2$—C), 1.49 (9H, s, C—(CH$_3$)$_3$)

Example 1

Synthesis of Phenylalanine Ethyl Ester (Compound 6)

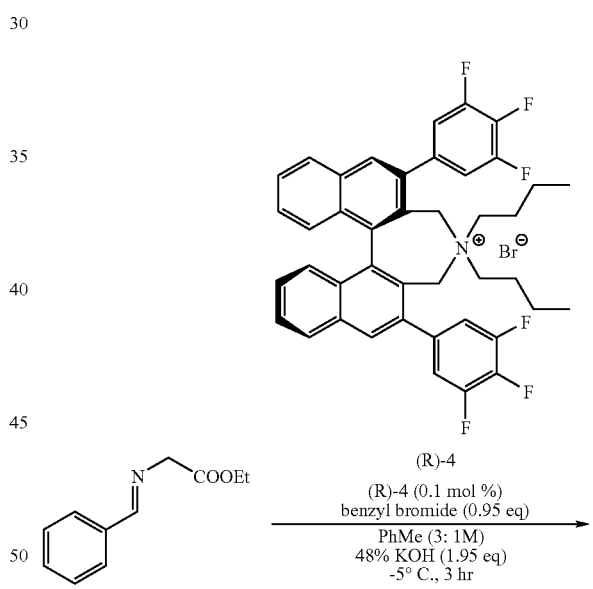

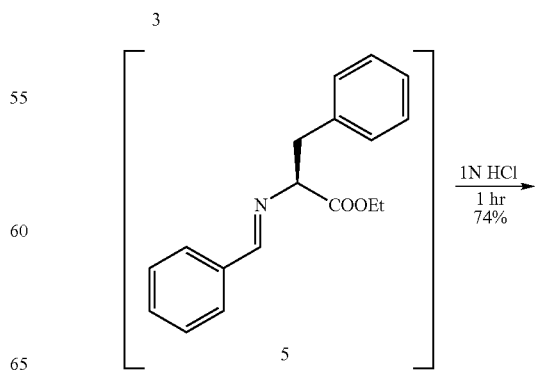

-continued

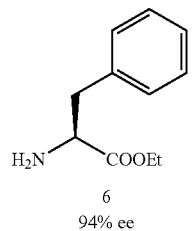

6
94% ee

The benzaldehyde Schiff base of glycine ethyl ester (compound 3) (3.82 g; 20 mmol), benzyl bromide (3.24 g; 19 mmol), and the compound (R)-4 (14.8 mg; 20 μmol) were added to toluene (20 mL), and the mixture was stirred vigorously (1400 rpm) with ice-salt cooling. When the internal temperature thereof had dropped to −5° C. or less, 48% KOH aqueous solution (4.50 g; 39 mmol, 1.95 equivalents) was added thereto. The mixture was stirred for three hours, while maintaining the internal temperature between −5° C. and −2° C. Distilled water (20 mL) was added thereto and the toluene layer was collected, and then the alkylated Schiff base (compound 5) was extracted with toluene (20 mL×2). The NMR spectrum of the obtained compound 5 is shown in Table 6.

TABLE 6

NMR spectrum of compound 5

400 MHz $^1$H-NMR (CDCl$_3$): δ 7.93 (1H, s), 7.70-7.68 (2H, m),
7.40-7.37 (3H, m), 7.30-7.19 (5H, m), 4.21-4.15 (3H, m), 3.36 (1H, dd,
5.2 Hz, 13.2 Hz), 3.14 (1H, dd, 8.8 Hz, 13.6 Hz), 1.25 (3H, t, 7.2 Hz)

Next, the extracted compound 5 was combined with the collected toluene layer, and 1 N hydrochloric acid (40 mL) was added thereto and the mixture was stirred at room temperature for one hour. The aqueous layer was collected by separation, and then the aqueous layer was washed with toluene (40 mL), and sodium carbonate was added thereto carefully to avoid too vigorous bubbling until pH of the solution reached not lower than 11 (confirmed by universal pH test paper). The mixture was extracted with ethyl acetate (50 mL×3) to collect the ethyl acetate layer. The ethyl acetate layer was dried over magnesium sulfate and concentrated under reduced pressure to give the title compound (S)-phenylalanine ethyl ester (compound 6) (2.69 g; yield 74%, optical purity 94% ee).

The optical purity of the phenylalanine ethyl ester (compound 6) was measured by HPLC under the conditions shown below.

Column: CHIRALCEL OD-H (4.6 mmφ×25 cm)
Mobile phase: hexane/ethanol/diethylamine=97/3/0.1
Flow rate: 1.0 mL/min
Temperature: room temperature
Detection: UV 254 nm
Retention time: (R)-form=10.2 min; (S)-form=10.7 min.

The NMR spectrum of the obtained compound (S)-6 is shown in Table 7.

TABLE 7

NMR spectrum of compound (S)-6

400 MHz $^1$H-NMR (CDCl$_3$): δ 7.19-7.33 (5H, m, Ph), 4.16 (2H, q,
J = 7.2 Hz, CH$_2$—C), 3.72 (1H, dd, J = 5.2, 7.8 Hz CH—C),
3.08 (1H, dd, J = 5.2, 13.5 Hz, CHPh), 2.87 (1H, dd, J = 7.9,
13.4 Hz, CHPh), 1.60 (2H, br s, NH$_2$), 1.23 (3H, t, 7.2 Hz, C—CH$_3$)

Example 2

Examination of the Change Over Time in the Optical Purity of the Phenylalanine Ethyl Ester (Compound 6)

The same procedure as in Example 1 was performed except that the 48% KOH aqueous solution was used at 1.95 equivalents, 3.9 equivalents, 1 equivalent, or 0.5 equivalents (additional 0.5 equivalents added after three hours because the starting material did not disappear) as detailed in Table 8 below, and the compound 6 in the reaction mixture was analyzed by HPLC every hour. The reaction times for the different quantities of 48% KOH aqueous solution are shown in Table 8 below. The results are shown in Table 8.

TABLE 8

| Amount of 48% KOH | Optical purity of compound 6 (% ee) | | | | | | |
|---|---|---|---|---|---|---|---|
| | 1 hr | 2 hr | 3 hr | 4 hr | 5 hr | 6 hr | 7 hr |
| 3.9 equivalents | 93 | 79 (starting meterial disappeared) | (not measured) | 20 (reaction was stopped: yeild 46%) | — | — | — |
| 1.95 equivalents | 94 | 94 (starting meterial disappeared) | 94 (reaction was stopped: yeild 74%) | — | — | — | — |
| 1 equivalent | 95 | 94 | 94 (starting meterial disappeared, reaction was stopped: yeild 68%) | — | — | — | — |
| 0.5 + 0.5 equivalents | 95 | 94 | 94 (addition of KOH) | 90 | 87 | 82 (starting meterial disappeared) | 79 (reaction was stopped: yeild 40%) |

In the early stage of the reaction, the compound (S)-6 with high optical purity was obtained for all cases. Thus, it is found that by adjusting the amount of base and the reaction time it is possible to obtain the compound 6 with high optical purity in a high yield.

Example 3

Examination of the Change Over Time in the Yield and the Optical Purity of the Benzyl Compound (Compound 6)

The benzaldehyde Schiff base of glycine ethyl ester (compound 3) (1.91 g; 10 mmol), benzyl bromide (1.62 g; 9.5 mmol), and the compound (R)-4 (7.4 mg; 10 μmol) were added to toluene (10 mL), and the mixture was stirred vigorously (1100 rpm) with ice-salt cooling. When the internal temperature thereof had dropped to −5° C. or less, 48% KOH aqueous solution (4.66 g; 40 mmol, 4.0 equivalents) was added thereto. The mixture was stirred for two hours while maintaining the internal temperature between −5° C. and −2° C. Distilled water (10 mL) was added thereto and the toluene layer was collected. Further, the alkylated Schiff base (compound 5) was extracted with toluene (10 mL×2). Thus obtained toluene layers were combined with the toluene layer collected previously, and 1 N hydrochloric acid (20 mL) was added thereto and the mixture was stirred at room temperature for one hour. The aqueous layer was collected by separation, and then the aqueous layer was washed with toluene (20 mL), and sodium carbonate was added thereto carefully to avoid too vigorous bubbling until pH of the solution reached not lower than 11 (confirmed by universal pH test paper). The mixture was extracted with ethyl acetate (25 mL×3) to collect the ethyl acetate layer. The ethyl acetate layer was dried over magnesium sulfate and concentrated under reduced pressure to give the title compound (S)-6 (1.36 g; yield 74%, optical purity 91% ee).

Under the same conditions (48% KOH aqueous solution (4.66 g; 40 mmol, 4.0 equivalents, 1100 rpm)), the reaction was stopped at 30 minutes, 1 hour, 4 hours, and 8 hours, and the yield and the optical purity at these times were measured. The results are shown in Table 9.

TABLE 9

|  | 0.5 hr | 1 hr | 2 hr | 4 hr | 8 hr |
|---|---|---|---|---|---|
| A; Yeild (%) | 35 | 63 | 74 | 60 | 49 |
| B; Optical purity (% ee) | 94 | 94 | 91 | 80 | 10 |
| A × B × 1/100 | 33 | 59 | 67 | 48 | 4.9 |

Example 4

Examination of Alkylation in Methyl tert-butyl Ether (MTBE)

The compound 3 (1.91 g; 10 mmol), benzyl bromide (1.62 g; 9.5 mmol), and the compound (R)-4 (7.5 mg; 10 μmol) were added to methyl tert-butyl ether (MTBE: 10 mL), and the mixture was stirred vigorously (1400 rpm) with ice-salt cooling. When the internal temperature thereof had dropped to −5° C. or less, 48% KOH aqueous solution (1.17 g; 10 mmol, 1.0 equivalents) was added thereto. The mixture was stirred for six hours while maintaining the internal temperature between −5° C. and −2° C. Distilled water (10 mL) was added thereto, and the MTBE layer was collected. Further, the alkylated Schiff base (compound 5) was then extracted with MTBE (10 mL×2). Thus obtained MTBE layers were combined with the MTBE layer collected previously, and 1 N hydrochloric acid (20 mL) was added thereto and the mixture was stirred at room temperature for one hour. The aqueous layer was collected by separation, and then the aqueous layer was washed with MTBE (20 mL), and sodium carbonate was added thereto carefully to avoid too vigorous bubbling until pH of the solution reached not lower than 11 (confirmed by universal pH test paper). The mixture was extracted with ethyl acetate (20 mL×3) to collect the ethyl acetate layer. The ethyl acetate layer was dried over magnesium sulfate and concentrated under reduced pressure to give the compound (S)-6 (1.16 g; yield 64%, optical purity 93% ee).

Example 5

Synthesis of 3-iodophenylalanine Ethyl Ester (Compound 8)

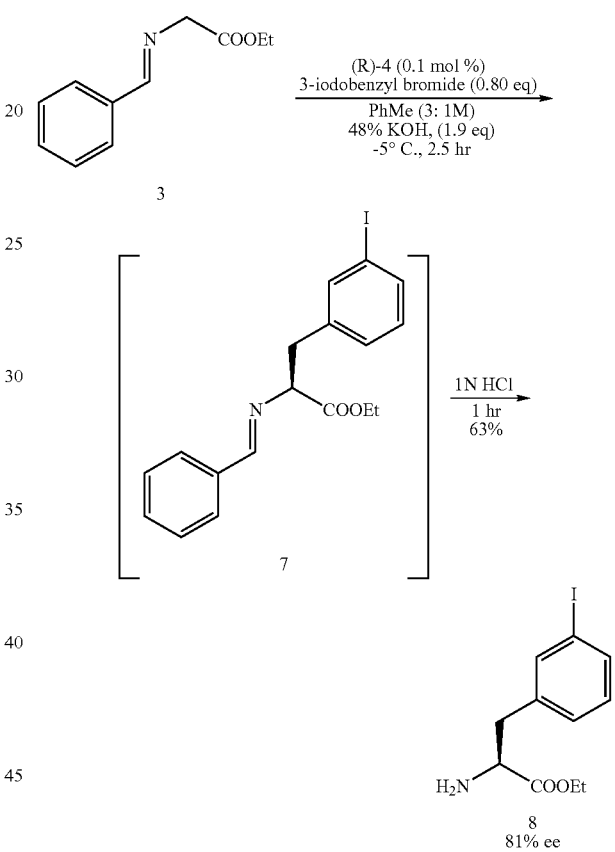

The compound 3 (0.96 g; 5.0 mmol), 3-iodobenzyl bromide (1.19 g; 4.0 mmol), and the compound (R)-4 (3.7 mg; 5 μmol) were added to toluene (5 mL), and the mixture was stirred vigorously (1400 rpm) with ice-salt cooling. When the internal temperature thereof had dropped to −5° C. or less, 48% KOH aqueous solution (1.15 g; 9.8 mmol) was added thereto. The mixture was stirred for 2.5 hours while maintaining the internal temperature between −5° C. and −2° C. Distilled water (5 mL) was added thereto, and the toluene layer was collected. Further, the alkylated Schiff base 7 was extracted with toluene (5 mL×2). Thus obtained toluene layers were combined with the toluene layer collected previously, 1 N hydrochloric acid (10 mL) was added thereto, and the mixture was stirred at room temperature for one hour. The aqueous layer was collected by separation at 40° C., and then the aqueous layer was washed with toluene (10 mL), and sodium carbonate was added thereto carefully to avoid too vigorous bubbling until pH of the solution reached not lower than 11 (confirmed by universal pH test paper). The mixture was extracted with ethyl acetate (30 mL×2) to collect the ethyl acetate layer. The ethyl acetate layer was dried over magnesium sulfate and concentrated under reduced pressure to give the compound (S)-8 (0.80 g; yield 63%, optical purity 81% ee). The optical purity was determined by benzoylating the compound 8.

The optical purity of the benzoylated compound 8 was measured by HPLC under the following conditions:
Column: CHIRALCEL OD-H (4.6 mmϕ×25 cm)
Mobile phase: hexane/isopropanol=95/5
Flow rate: 1.5 mL/min
Temperature: room temperature
Detection: UV 254 nm
Retention time: (R)-form=10.0 min; (S)-form=13.8 min
The NMR spectrum of the obtained compound (S)-8 is shown in Table 10.

TABLE 10

NMR spectrum of compound (S)-8

400 MHz $^1$H-NMR (CDCl$_3$): δ 7.57-7.59 (2H, m), 7.18 (1H, d, J = 7.8 Hz), 7.04 (1H, t, J = 7.8 Hz), 4.17 (2H, q, J = 7.1 Hz, CH$_2$—C), 3.68 (1H, dd, J = 5.4, 7.8 Hz CH—C), 2.99 (1H, dd, J = 5.4, 13.5 Hz, CHPh), 2.82 (1H, dd, J = 7.8, 13.4 Hz, CHPh), 1.57 (2H, br s, NH$_2$), 1.25 (3H, t, 7.2 Hz, C—CH$_3$)

Example 6

Examination of the Use of a Cinchona Alkaloid Quaternary Ammonium Phase-Transfer Catalyst

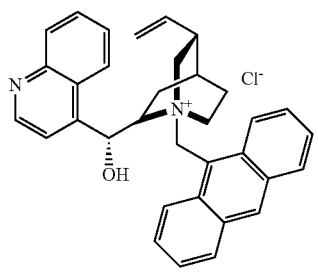

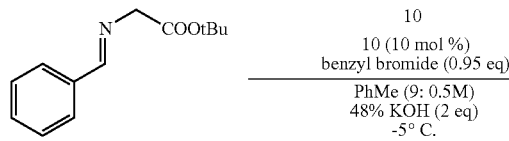

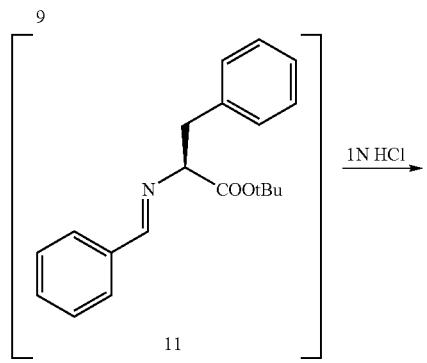

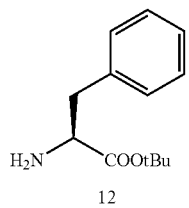

The benzaldehyde Schiff base of glycine tert-butyl ester (compound 9) (0.44 g; 2 mmol), benzyl bromide (0.32 g; 1.9 mmol), and N-(9-anthracenylmethyl)cinchonidium chloride (compound 10) (107 mg; 0.2 mmol) were added to toluene (4 mL), and the mixture was stirred vigorously (1400 rpm) with ice-salt cooling. When the internal temperature thereof had dropped to −5° C. or less, 48% KOH aqueous solution (0.46 g; 4 mmol, 2 equivalents) was added thereto. The mixture was stirred for one hour while maintaining the internal temperature between −5° C. and −2° C. Distilled water (10 mL) was added thereto and the toluene layer was collected, and then the alkylated Schiff base (compound 11) was extracted with toluene (10 mL×2). Thus obtained toluene layers were combined with the toluene layer collected previously, 1 N hydrochloric acid (10 mL) was added thereto, and the mixture was stirred at room temperature for one hour. The aqueous layer was collected by separation, and then the aqueous layer was washed with toluene (10 mL), and sodium carbonate was added thereto carefully to avoid too vigorous bubbling until pH of the solution reached not lower than 11 (confirmed by universal pH test paper). The mixture was extracted with ethyl acetate (10 mL×3) to collect the ethyl acetate layer. The ethyl acetate layer was dried over magnesium sulfate and concentrated under reduced pressure to give (S)-phenylalanine tert-butyl ester (compound (S)-12) (0.11 g; yield 25%, optical purity 80% ee). The optical purity of the compound 12 was measured by HPLC under the following conditions:
Column: CHIRALCEL OD-H (4.6 mmϕ×25 cm)
Mobile phase: hexane/isopropanol=98/2
Flow rate: 1.0 mL/min
Temperature: room temperature
Detection: UV 220 nm
Retention time: (R)-form=10.7 min; (S)-form=11.2 min
The NMR spectrum of the obtained compound (S)-12 is shown in Table 11.

TABLE 11

NMR spectrum of compound (S)-12

400 MHz $^1$H-NMR (CDCl$_3$): δ 7.19-7.33 (5H, m, Ph), 3.61 (1H, dd, J = 5.7, 7.8 Hz CH—C), 3.03 (1H, dd, J = 5.6, 13.6 Hz, CHPh), 2.87 (1H, dd, J = 7.7, 13.5 Hz, CHPh), 1.60 (2H, br s, NH$_2$), 1.43 (9H, s, C—(CH$_3$)$_3$)

Comparative Example 1

The same procedure was performed under the same conditions as in Example 6, after stirring for four hours while maintaining the internal temperature between −5° C. and −2°

C. As a result, the compound 12 was obtained in a 63% yield, however, the optical purity was 0% ee.

Example 7

Examination of Schiff Base-1

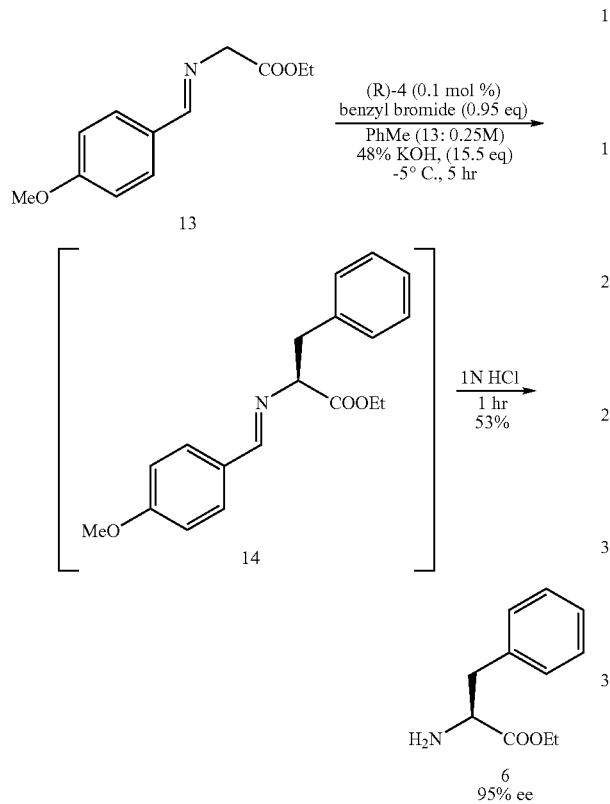

The p-anisaldehyde Schiff base of glycine ethyl ester (compound 13) (1.10 g; 5 mmol), benzyl bromide (0.81 g; 4.75 mmol), and the compound (R)-4 (3.7 mg; 5 μmol) were added to toluene (20 mL), and the mixture was stirred vigorously (1400 rpm) with ice-salt cooling. When the internal temperature thereof had dropped to −5° C. or less, 48% KOH aqueous solution (9 g; 78 mmol, 15.5 equivalents) was added thereto. The mixture was stirred for three hours while maintaining the internal temperature between −5° C. and −2° C. Distilled water (20 mL) was added thereto and the toluene layer was collected, and then the alkylated Schiff base (compound 14) was extracted with toluene (20 mL×2). Thus obtained toluene layers were combined with the toluene layer collected previously, 1 N hydrochloric acid (10 mL) was added thereto, and the mixture was stirred at room temperature for one hour. The aqueous layer was collected by separation, and then the aqueous layer was washed with toluene (10 mL), and sodium carbonate was added thereto carefully to avoid too vigorous bubbling until pH of the solution reached not lower than 11 (confirmed by universal pH test paper). The mixture was extracted with ethyl acetate (20 mL×3) to collect the ethyl acetate layer. The ethyl acetate layer was dried over magnesium sulfate and concentrated under reduced pressure to give (S)-phenylalanine ethyl ester (compound 6) (0.42 g; yield 53%, optical purity 95% ee).

Example 8

Examination of Schiff Base-2

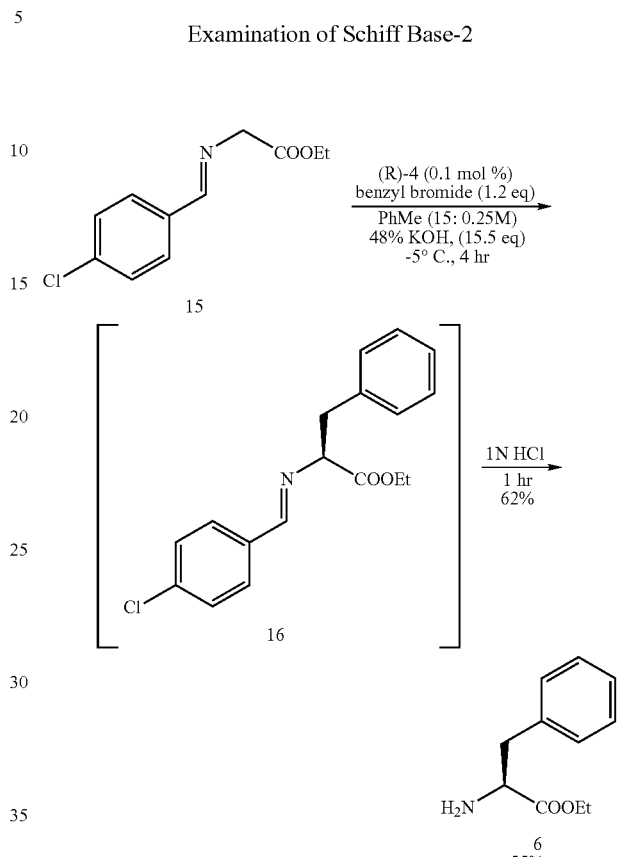

The p-chlorobenzaldehyde Schiff base of glycine ethyl ester (compound 15) (4.51 g; 20 mmol), benzyl bromide (4.12 g; 24 mmol), and compound (R)-4 (14.8 mg; 20 μmol) were added to toluene (80 mL), and the mixture was stirred vigorously (1400 rpm) with ice-salt cooling. When the internal temperature thereof had dropped to −5° C. or less, 48% KOH aqueous solution (36 g; 0.31 mmol, 15.5 equivalents) was added thereto. The mixture was stirred for 4.5 hours while maintaining the internal temperature between −5° C. and −2° C. Distilled water (20 mL) was added thereto and the toluene layer was separated off, and then the alkylated Schiff base (compound 16) was extracted with toluene (25 mL×3). Thus obtained toluene layers were combined with the toluene layer collected previously, 1 N hydrochloric acid (120 mL) was added thereto, and the mixture was stirred at room temperature for one hour. The aqueous layer was collected by separation, and then the aqueous layer was washed with toluene (30 mL), and sodium carbonate was added thereto carefully to avoid too vigorous bubbling until pH of the solution reached not lower than 11 (confirmed by universal pH test paper). The mixture was extracted with ethyl acetate (100 mL×2) to collect the ethyl acetate layer. The ethyl acetate layer was dried over magnesium sulfate and concentrated under reduced pressure to give (S)-phenylalanine ethyl ester (compound 6) (2.40 g; yield 62%, optical purity 55% ee).

The change over time in the optical purity of the compound 6 produced through this reaction was measured. The optical purity was 90% ee at one hour, 85% ee at two hours, and 62% ee at four hours. Thus, the compound 6 was obtained with high optical purity in the early stage of the reaction.

Example 9

Examination of the Compound of the Formula (III)-1

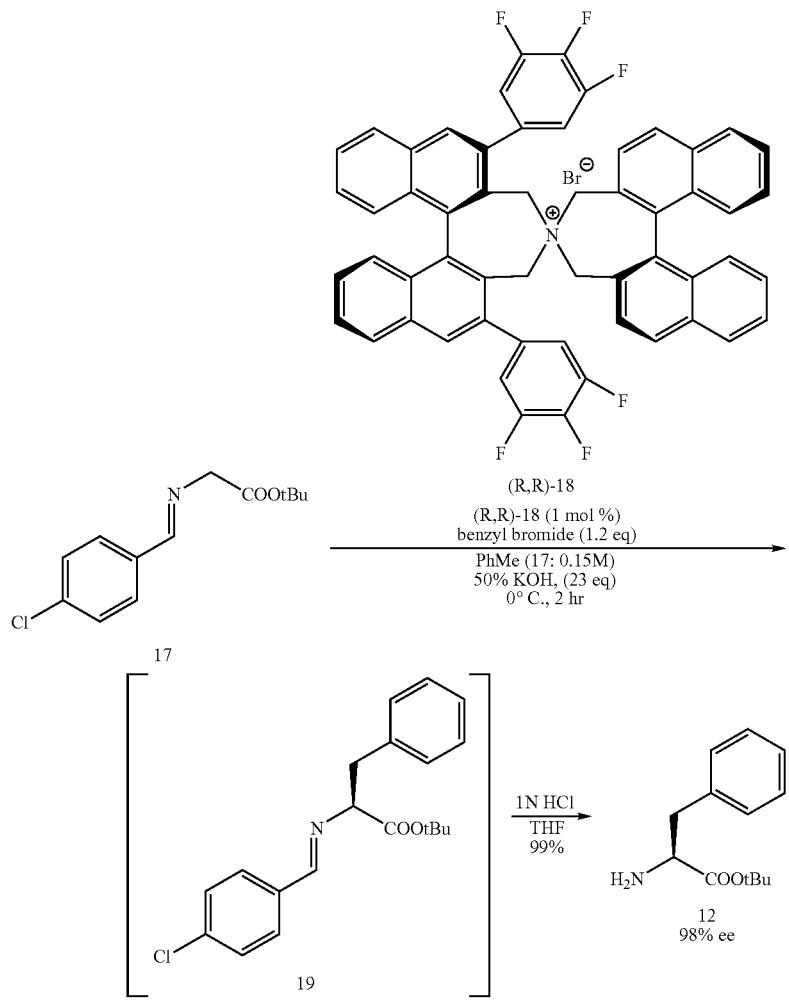

Under an argon atmosphere, the p-chlorobenzaldehyde Schiff base of glycine tert-butyl ester (compound 17) (76.1 mg; 0.30 mmol), benzyl bromide (61.5 mg; 0.36 mmol), and the compound (R,R)-18 (2.7 mg; 3 μmol) were added to toluene (2.0 mL), and the mixture was stirred vigorously with ice-salt cooling. When the internal temperature thereof had dropped to 0° C. or less, 50% KOH aqueous solution (0.6 mL; 0.008 mol, 23 equivalents) was added thereto. The mixture was stirred for two hours while maintaining the internal temperature at 0° C. Distilled water (10 mL) was added thereto and the toluene layer was separated off, and then the alkylated Schiff base (compound 19) was extracted with ether (10 mL). Thus obtained ether layer was combined with the toluene layer collected previously, dried over sodium sulfate and concentrated under reduced pressure. The residue was diluted with THF (10 mL), 1 N hydrochloric acid (10 mL) was added thereto at 0° C., and the mixture was stirred for 30 minutes. After returned to room temperature, the mixture was washed with ether. Then, the ether layer was extracted again with 1 N hydrochloric acid. The acidic aqueous layer was collected, and then neutralized with sodium hydrogencarbonate at 0° C. The mixture was extracted with ethyl acetate (10 mL×2) to collect the ethyl acetate layer. The ethyl acetate layer was dried over sodium sulfate and concentrated under reduced pressure, and then the mixture was purified by silica gel column chromatography (hexane/ethyl acetate=1/3) to give (S)-phenylalanine tert-butyl ester (compound 12) (65.7 mg; yield 99%, optical purity 98% ee).

The optical purity of (S)-phenylalanine tert-butyl ester (compound 12) was measured by HPLC under the following conditions:

Column: CHIRALCEL OD-H (4.6 mmφ×25 cm)

Mobile phase: hexane/ethanol/diethylamine=100/1/0.1

Flow rate: 0.5 mL/min

Temperature: room temperature

Detection: UV 254 nm (R)-Phenylalanine tert-butyl ester (compound 43) (63 mg; yield 95%, optical purity 98% ee) was obtained in the same manner as in Example 9, except that the compound (S)-4 (2.2 mg; 3 μmol) was used instead of the compound (R,R)-18 as a catalyst.

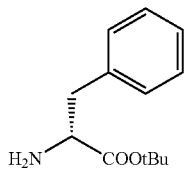

43

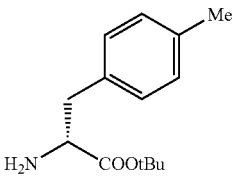

44

Example 10

Examination of the Compound of the Formula (III)-2

Example 11

Examination of the Compound of the Formula (III)-3

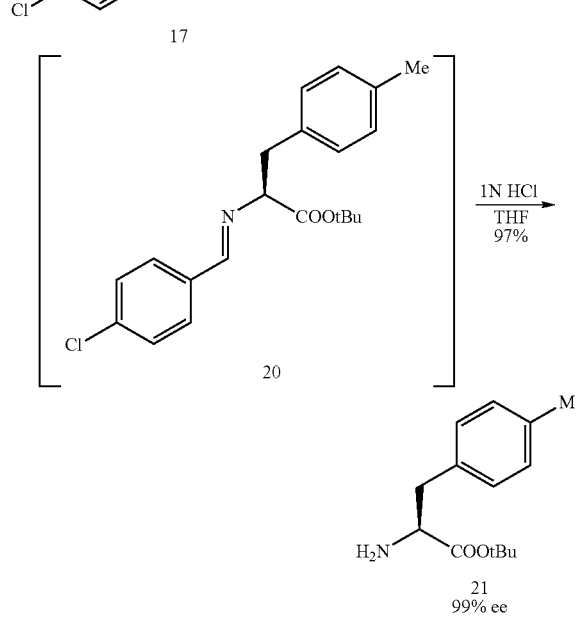

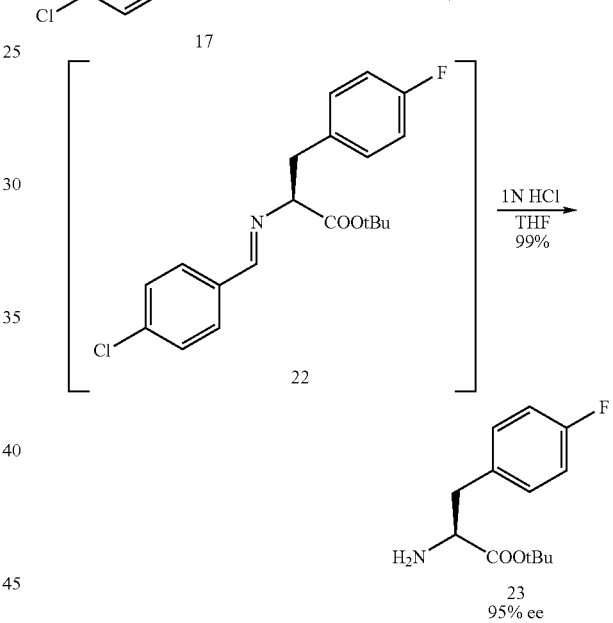

(S)-(p-Methylphenyl)alanine tert-butyl ester (compound 21) (68.5 mg; yield 97%, optical purity 99% ee) was obtained in the same manner as in Example 9 except that p-methylbenzyl bromide (66.6 mg; 0.36 mmol) was used instead of benzyl bromide.

The optical purity of (S)-(p-methylphenyl)alanine tert-butyl ester (compound 21) was measured by HPLC under the following conditions:

Column: CHIRALCEL OD-H (4.6 mmφ×25 cm)
Mobile phase: hexane/ethanol/diethylamine=100/1/0.1
Flow rate: 0.5 mL/min
Temperature: room temperature
Detection: UV 254 nm (R)-(p-Methylphenyl)alanine tert-butyl ester (compound 44) (67.8 mg; yield 96%, optical purity 98% ee) was obtained in the same manner as in Example 10 except that the compound (S)-4 (2.2 mg; 3 μmol) was used instead of compound (R,R)-18 as a catalyst.

(S)-(p-Fluorophenyl)alanine tert-butyl ester (compound 23) (71.1 mg; yield 99%, optical purity 95% ee) was obtained in the same manner as in Example 9 except that p-fluorobenzyl bromide (68.0 mg; 0.36 mmol) was used instead of benzyl bromide.

The optical purity of (S)-(p-fluorophenyl)alanine tert-butyl ester (compound 23) was measured by HPLC under the following conditions:

Column: CHIRALCEL OD-H (4.6 mmφ×25 cm)
Mobile phase: hexane/ethanol/diethylamine=100/1/0.1
Flow rate: 0.5 mL/min
Temperature: room temperature
Detection: UV 254 nm (R)-(p-Fluorophenyl)alanine tert-butyl ester (compound 45) (69.6 mg; yield 97%, optical purity 99% ee) was obtained in the same manner as in Example 11 except that (S)-4 (2.2 mg; 3 μmol) was used instead of the compound (R,R)-18 as a catalyst.

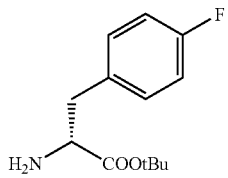

46

Example 12

Examination of the Compound of the Formula (III)-4

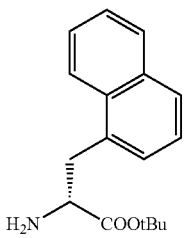

(S)-1-Naphthylalanine tert-butyl ester (compound 25) (78.1 mg; yield 96%, optical purity 99% ee) was obtained in the same manner as in Example 9 except that 1-bromomethyl naphthalene (79.6 mg; 0.36 mmol) was used instead of benzyl bromide.

The optical purity of (S)-1-naphthylalanine tert-butyl ester (compound 25) was measured by HPLC under the following conditions:
Column: CHIRALCEL OD-H (4.6 mmϕ×25 cm)
Mobile phase: hexane/2-propanol=100/1
Flow rate: 0.5 mL/min
Temperature: room temperature
Detection: UV 254 nm (R)-Naphthylalanine tert-butyl ester (compound 46) (78.1 mg; yield 96%, optical purity 98% ee) was obtained in the same manner as in Example 12 except that the compound (S)-4 (2.2 mg; 3 μmol) was used instead of the compound (R,R)-18 as a catalyst.

Example 13

Examination of the Compound of the Formula (III)-5

(S)-1-Cinnamylglycine tert-butyl ester (compound 27) (61.1 mg; yield 82%, optical purity 94% ee) was obtained in the same manner as in Example 9 except that cinnamyl bromide (70.9 mg; 0.36 mmol) was used instead of benzyl bromide.

The optical purity of (S)-1-cinnamylglycine tert-butyl ester (compound 27) was measured by HPLC under the following conditions:
Column: CHIRALCEL OD-H (4.6 mmϕ×25 cm)
Mobile phase: hexane/ethanol/diethylamine=100/1/0.1

Flow rate: 0.5 mL/min

Temperature: room temperature

Detection: UV 254 nm

The NMR spectrum of the obtained compound (S)-27 is shown in Table 12.

TABLE 12

| NMR spectrum of compound (S)-27 |
| --- |
| 400 MHz $^1$H-NMR (CDCl$_3$,) δ 7.35-7.26 (4H, m), 7.22 (1H, m), 6.48 (1H, d, J = 16.0 Hz), 6.15 (1H, m), 3.49 (1H, t, J = 6.0 Hz), 2.57 (2H, m), 1.69 (2H, b) 1.46 (9H, s) |

(R)-Cinnamylglycine tert-butyl ester (compound 47) (67.1 mg; yield 90%, optical purity 89% ee) was obtained in the same manner as in Example 13 except that the compound (S)-4 (2.2 mg; 3 μmol) was used instead of the compound (R,R)-18 as a catalyst.

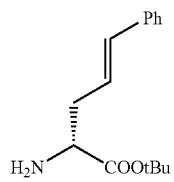

47

Example 14

Examination of the Compound of the Formula (III)-6

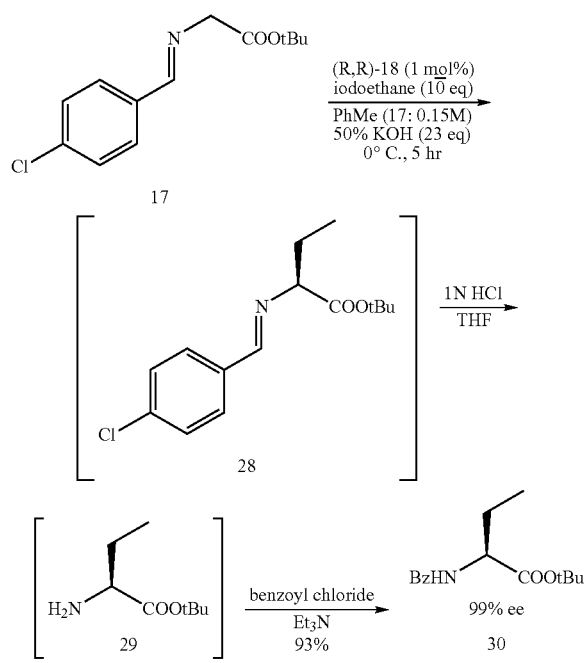

Under an argon atmosphere, the p-chlorobenzaldehyde Schiff base of glycine tert-butyl ester (compound 17) (76.1 mg; 0.30 mmol), iodoethane (240 μL; 3.0 mmol), and the compound (R,R)-18 (2.7 mg; 3 μmol) were added to toluene (2.0 mL), and the mixture was stirred vigorously with ice-salt cooling. When the internal temperature thereof had dropped to 0° C. or less, 50% KOH aqueous solution (0.6 mL; 0.008 mol, 23 equivalents) was added thereto. The mixture was stirred for two hours while maintaining the internal temperature at 0° C. Distilled water (10 mL) was added thereto and the toluene layer was separated off, and then the alkylated Schiff base (compound 19) was extracted with ether (10 mL). Thus obtained ether layer was combined with the toluene layer collected previously, dried over sodium sulfate and concentrated under reduced pressure. The residue was diluted with THF (10 mL), 1 N hydrochloric acid (10 mL) was added thereto at 0° C., and the mixture was stirred for 30 minutes. After returned to room temperature, the mixture was washed with ether. Next, the ether layer was extracted again with 1 N hydrochloric acid. The acidic aqueous layer was collected, and then neutralized with sodium hydrogencarbonate at 0° C. The mixture was extracted with chloroform (10 mL×2) to collect the chloroform layer. The chloroform layer was dried over sodium sulfate and filtered. To the filtrate, triethylamine (84.0 μL; 0.6 mmol) and benzoyl chloride (70.0 μL; 0.6 mmol) were added at 0° C. The mixture was stirred for one hour at 0° C. and then purified by silica gel column chromatography (hexane/ethyl acetate=9/1) to give (S)—N-benzoyl-ethylglycine tert-butyl ester (compound 30) (73.2 mg; yield 93%, optical purity 99% ee).

The optical purity of (S)—N-benzoyl-ethylglycine tert-butyl ester (compound 30) was measured by HPLC under the following conditions:

Column: CHIRALCEL AD-H (4.6 mmφ×25 cm)

Mobile phase: hexane/2-propanol=20/1

Flow rate: 0.5 mL/min

Temperature: room temperature

Detection: UV 254 nm (R)—N-Benzoyl-ethylglycine tert-butyl ester (compound 48) (63.8 mg; yield 81%, optical purity 90% ee) was obtained in the same manner as in Example 14 except that the compound (S)-4 (2.2 mg; 3 μmol) was used instead of the compound (R,R)-18 as a catalyst.

48

Example 15

Examination of the Compound of the Formula (III)-7

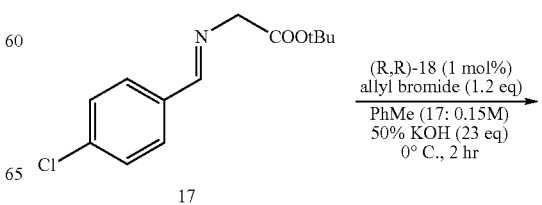

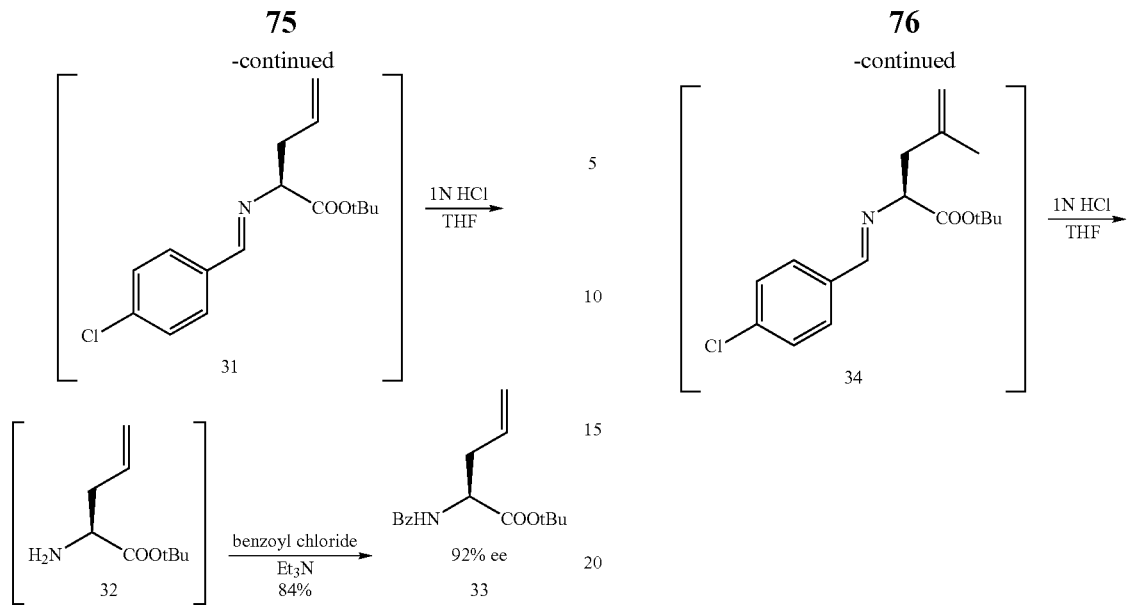

(S)—N-Benzoyl-allylglycine tert-butyl ester (compound 33) (69.3 mg; yield 84%, optical purity 92% ee) was obtained in the same manner as in Example 14 except that allyl bromide (43.6 mg; 0.36 mmol) was used instead of iodoethane (240 μL; 3.0 mmol).

The optical purity of (S)—N-benzoyl-allylglycine tert-butyl ester (compound 33) was measured by HPLC under the following conditions:
Column: CHIRALCEL AD-H (4.6 mmφ×25 cm)
Mobile phase: hexane/2-propanol=20/1
Flow rate: 0.5 mL/min
Temperature: room temperature
Detection: UV 254 nm (R)—N-Benzoyl-allylglycine tert-butyl ester (compound 49) (76.0 mg; yield 92%, optical purity 98% ee) was obtained in the same manner as in Example 15 except that the compound (S)-4 (2.2 mg; 3 μmol) was used instead of the compound (R,R)-18 as a catalyst.

49

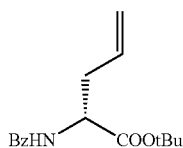

Example 16

Examination of the Compound of the Formula (III)-8

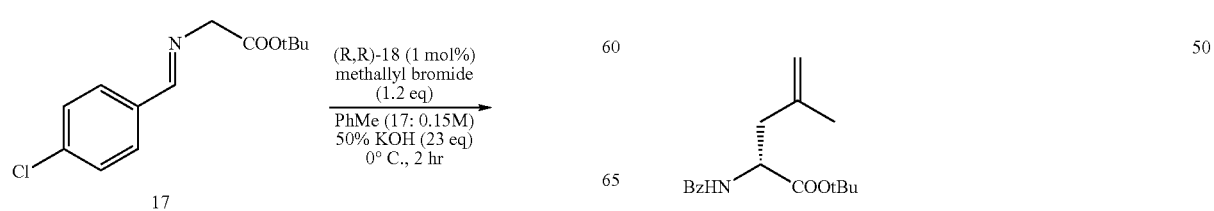

(S)—N-Benzoyl-methallylglycine tert-butyl ester (compound 36) (85.9 mg; yield 99%, optical purity 98% ee) was obtained in the same manner as in Example 14, except that methallyl bromide (48.6 mg; 0.36 mmol) was used instead of iodoethane (240 μL; 3.0 mmol).

The optical purity of (S)—N-benzoyl-methallylglycine tert-butyl ester (compound 36) was measured by HPLC under the following conditions:
Column: CHIRALCEL AD-H (4.6 mmφ×25 cm)
Mobile phase: hexane/2-propanol=20/1
Flow rate: 0.5 mL/min
Temperature: room temperature
Detection: UV 254 nm (R)—N-Benzoyl-methallylglycine tert-butyl ester (compound 50) (82.5 mg; yield 95%, optical purity 96% ee) was obtained in the same manner as in Example 16 except that the compound (S)-4 (2.2 mg; 3 μmol) was used instead of the compound (R,R)-18 as a catalyst.

50

Example 17

Alkylation Using the Compound (S,S)-37-1

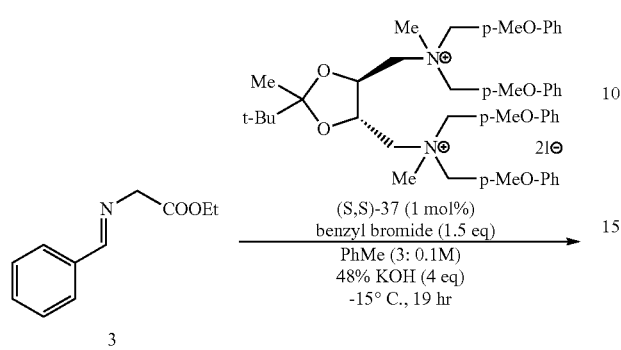

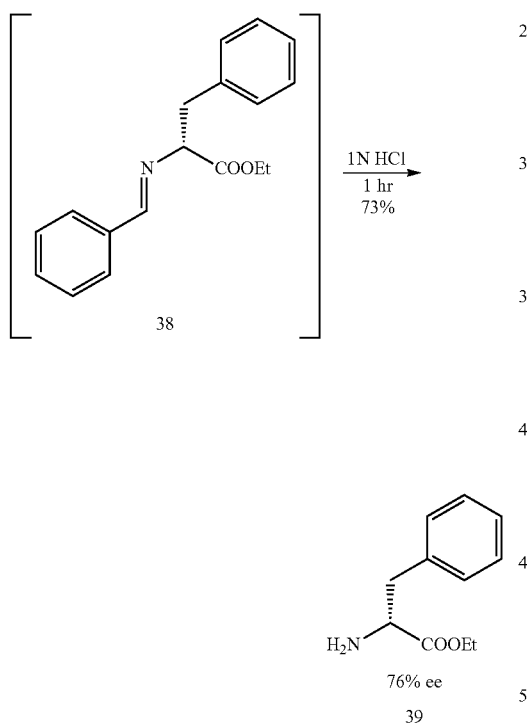

Under a nitrogen atmosphere, the benzaldehyde Schiff base of glycine ethyl ester (compound 3) (191 mg; 1.0 mmol), benzyl bromide (257 mg; 1.5 mmol), and TaDias-[(4S,5S)-2-tert-butyl-2-methyl-N,N,N',N'-tetrakis(4-methoxybenzyl)] diolide (compound (S,S)-37) (9.7 mg; 0.01 mmol) were added to toluene (10.0 mL), and the mixture was stirred vigorously with ice-salt cooling. When the internal temperature thereof had dropped to −15° C. or less, 48% KOH aqueous solution (0.47 g; 4 mmol, 4 equivalents) was added thereto. The mixture was stirred for 19 hours while maintaining the internal temperature at −15° C. Distilled water (5 mL) was added thereto and the toluene layer was collected, and then the alkylated Schiff base (compound 38) was extracted with toluene (10 mL×2). Thus obtained toluene layers were combined with the toluene layer collected previously, then 1 N hydrochloric acid (8 mL) was added thereto, and the mixture was stirred at room temperature for one hour. The aqueous layer was collected by separation, and then the aqueous layer was washed with toluene (5 mL), and sodium carbonate was added thereto carefully to avoid too vigorous bubbling until pH of the solution reached not lower than 11 (confirmed by universal pH test paper). The mixture was extracted with ethyl acetate (10 mL×2) to collect the ethyl acetate layer. The ethyl acetate layer was dried over magnesium sulfate and concentrated under reduced pressure to give the title compound (R)-phenylalanine ethyl ester (compound 39) (140 mg; yield 73%, optical purity 76% ee).

Example 18

Alkylation Using the Compound (S,S)-37-2

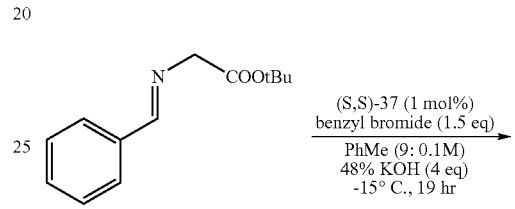

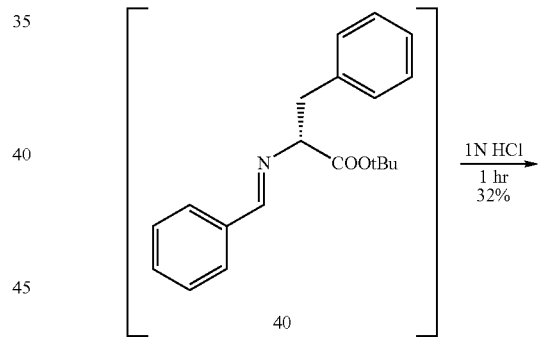

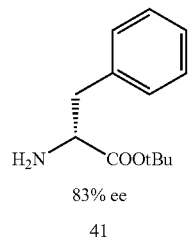

The title compound (R)-phenylalanine-tert-butyl ester (compound 41) (70 mg; yield 32%, optical purity 83% ee) was obtained in the same manner as in Example 17 except that the benzaldehyde Schiff base of glycine tert-butyl ester (compound 9) (219 mg; 1.0 mmol) was used instead of the benzaldehyde Schiff base of glycine ethyl ester (compound 3) (191 mg; 1.0 mmol).

Example 19

Alkylation Using the Compound (R)-42

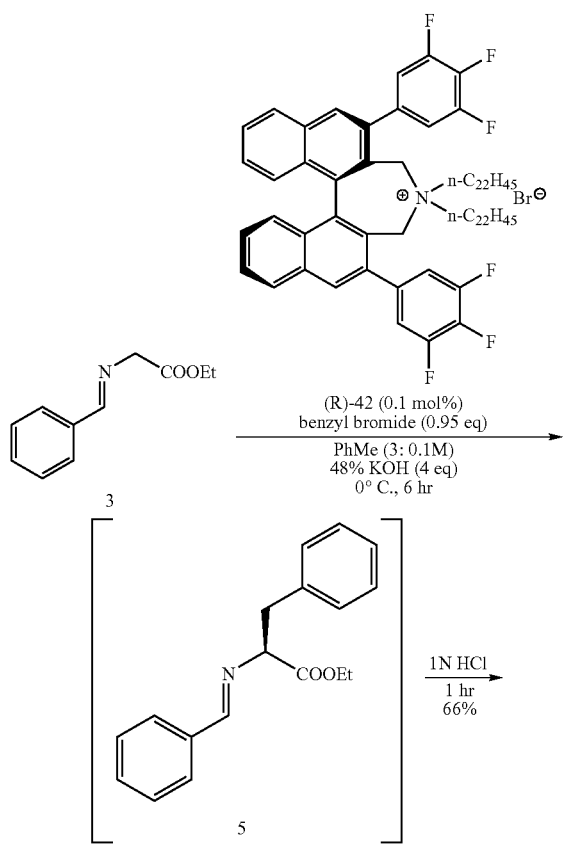

The benzaldehyde Schiff base of glycine ethyl ester (compound 3) (191 mg; 1 mmol), benzyl bromide (162 mg; 0.95 mmol), and the compound (R)-42 (1.25 mg; 1 μmol) were added to toluene (10 mL), and the mixture was stirred vigorously (1400 rpm) with ice-salt cooling. When the internal temperature thereof had dropped to −5° C. or less, 48% KOH aqueous solution (0.47 g; 4 mmol, 4 equivalents) was added thereto. The mixture was stirred for 6 hours while maintaining the internal temperature between −5° C. and −2° C. Distilled water (5 mL) was added thereto and the toluene layer was collected, and then the alkylated Schiff base (compound 5) was extracted with toluene (10 mL×2). Thus obtained toluene layers were combined with the toluene layer collected previously, then 1 N hydrochloric acid (2.5 mL) was added thereto and the mixture was stirred at room temperature for one hour. The aqueous layer was collected by separation, and then sodium carbonate was added thereto carefully to avoid too vigorous bubbling until pH of the solution reached not lower than 11 (confirmed by universal pH test paper). The mixture was extracted with ethyl acetate (5 mL×3) to collect the ethyl acetate layer. The ethyl acetate layer was dried over magnesium sulfate and concentrated under reduced pressure to give the title compound (S)-phenylalanine ethyl ester (compound 6) (120 mg; yield 66%, optical purity 88% ee).

Example 20

Benzylation of the Compound 44

Example 20-1

Preparation of the Terephthalaldehyde Schiff Base of Glycine Ethyl Ester (Compound 44)

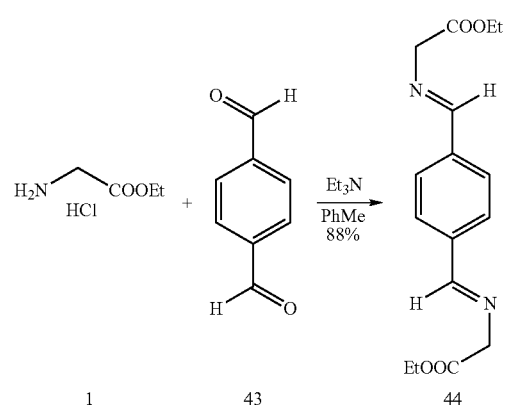

Under a nitrogen atmosphere, toluene (35 mL) was added to glycine ethyl ester hydrochloride (compound 1) (8.72 g; 62.5 mmol), and then triethylamine (10.45 mL; 75 mmol) was added thereto and the mixture was stirred. Further, terephthalaldehyde (compound 43) (3.35 g; 25 mmol) was added thereto, and the mixture was warmed and stirred at 50° C. for two hours. Water (50 mL) and toluene (50 mL) was added thereto, and the mixture was separated to two layers. The toluene layer was washed with water (40 mL) and saturated saline (40 mL), and then concentrated by evaporator to give compound 44 (6.7 g; yield 88%). The NMR spectrum of the obtained compound 44 is shown in Table 13.

TABLE 13

| NMR spectrum of compound 44 |
|---|
| 400 MHz $^1$H-NMR (CDCl$_3$): δ 8.32 (2H, s, CH═N), 7.84 (4H, s, ArH), 4.42 (4H, s, N—CH$_2$—CO), 4.25 (4H, q, J = 7.2 Hz, O—CH$_2$—C), 1.30 (6H, m, C—CH$_3$) |

Example 20-2

Benzylation of the Compound 44

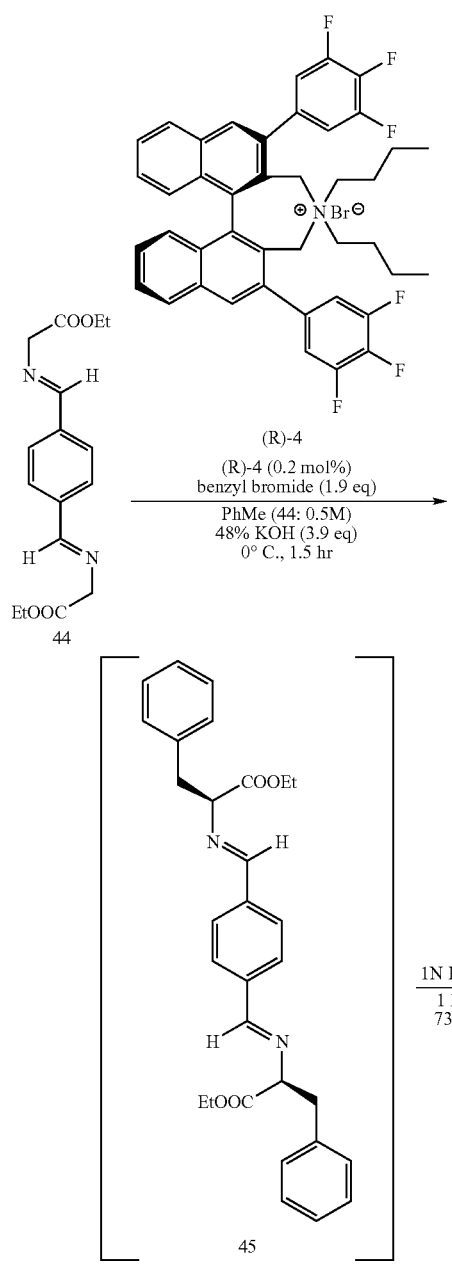

Under a nitrogen atmosphere, the terephthalaldehyde Schiff base of glycine ethyl ester (compound 44) (1.52 g; 5 mmol), benzyl bromide (1.62 g; 9.5 mmol), and the compound (R)-4 (7.4 mg; 10 μmol) were added to toluene (10 mL), and the mixture was stirred vigorously (1000 rpm) with ice-salt cooling. When the internal temperature thereof had dropped to 0° C. or less, 48% KOH aqueous solution (2.28 g; 19 mmol, 3.9 equivalents) was added thereto. The mixture was stirred for 1.5 hours while maintaining the internal temperature between 0° C. and 5° C. Distilled water (10 mL) and ethyl acetate (30 mL) were added thereto and the toluene-ethyl acetate layer was collected, then ethyl acetate (20 mL) was added again thereto to extract the alkylated Schiff base (compound 45). The NMR spectrum of the obtained compound 45 is shown in Table 14.

TABLE 14

| NMR spectrum of compound 45 |
|---|
| 400 MHz $^1$H-NMR (CDCl$_3$): δ 7.91 (2H, s), 7.70 (4H, s), 7.25-7.10 (10H, m), 4.21-4.15 (6H, m), 3.36 (2H, dd, 5.2 Hz, 13.6 Hz), 3.14 (2H, dd, 9.2 Hz, 13.6 Hz), 1.25 (6H, t, 7.2 Hz) |

The collected toluene-ethyl acetate layers were combined, and 1 N hydrochloric acid (20 mL) was added thereto, and the mixture was stirred at room temperature for one hour. The aqueous layer was collected by separation, then the aqueous layer was washed with ethyl acetate (10 mL), and then sodium carbonate was added thereto carefully to avoid too vigorous bubbling until pH of the solution reached not lower than 11 (confirmed by universal pH test paper). The mixture was extracted with ethyl acetate (40 mL×3) to collect the ethyl acetate layer. The ethyl acetate layer was dried over magnesium sulfate and concentrated under reduced pressure to give the title compound (S)-phenylalanine ethyl ester (compound 6) (1.33 g; yield 73%, optical purity 84% ee).

Example 21

Benzylation of the Compound 49

Example 21-1

Preparation of the Benzaldehyde Schiff Base of Glycine Diphenylmethylamide (Compound 49)

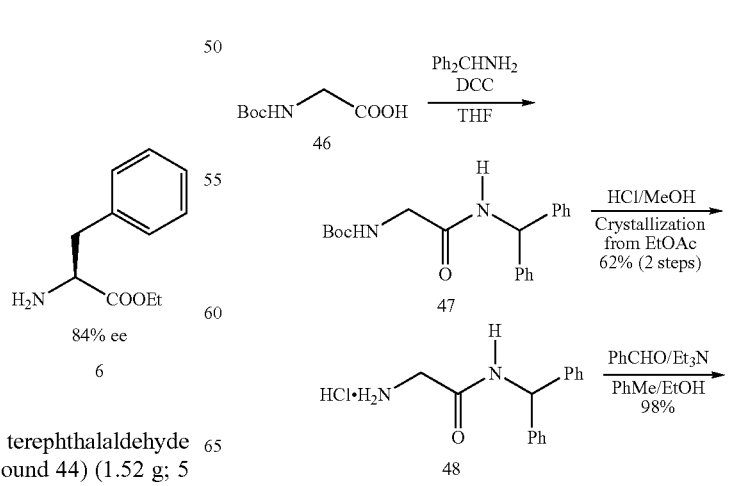

-continued

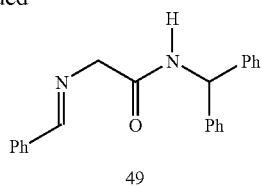

49

With ice-water cooling, N,N'-dicyclohexylcarbodiimide (DCC, 9.3 g; 45 mmol) was added to THF (100 mL), and then Boc-glycine (compound 46) (7.5 g; 42.9 mmol) was added. Then, benzhydrylamine (8.3 g; 45 mmol) was added thereto, returned to room temperature and the mixture was stirred for three hours. The resulting precipitate was filtered out and the filtrate was concentrated, and then ethyl acetate (150 mL) was added to the residue and the resulting precipitate was filtered out again. The filtered ethyl acetate layer was washed with 5% citric acid (40 mL×2), saturated saline (30 mL), saturated sodium hydrogencarbonate water (40 mL×2), then saturated saline (30 mL), dried over sodium sulfate and then concentrated to give 15.3 g of the crude compound 47.

Next, a 10% hydrochloric acid methanol solution (by Tokyo Chemical Industry) (120 mL) were added to the compound 47 (14.8 g), and the mixture was stirred for 6 hours. The methanol was removed under reduced pressure, then ethyl acetate (120 mL) was added thereto and the mixture was cooled to 5° C. The precipitated sediment was filtered and washed with ethyl acetate (120 mL). The precipitate obtained was dried by blowing at 50° C. (12 hours) to give the compound 48 (7.10 g, 62%).

The compound 48 (2.77 g; 10 mmol) was added to toluene (20 mL) and the mixture was stirred. Then, triethylamine (1.11 g; 11 mmol) and benzaldehyde (1.06 g; 11 mmol) were added thereto and the mixture was stirred for two hours. Ethanol was added (10 mL) thereto and the mixture was stirred for additional two hours. After removing the solvent under reduced pressure, ethyl acetate (40 mL) and water (20 mL) were added thereto. The crystal precipitated was filtered and then washed with water (10 mL) and ethyl acetate (20 mL). The obtained precipitate was dried by blowing at 50° C. (12 hours) to give 1.40 g of the compound 49. This filtrate was concentrated and the precipitate was dissolved in chloroform (100 mL), the solution was washed with water (20 mL×2) and dried over sodium sulfate, and then concentrated under reduced pressure to give the compound 49 (1.80 g, 3.20 g when combined with the above crystal; yield 98%). The NMR spectrum of the obtained compound 49 is shown in Table 15.

TABLE 15

NMR spectrum of compound 49

400 MHz $^1$H-NMR (CDCl$_3$): δ 8.34 (1H, s, CH=N), 7.74-7.70 (2H, m, ArH), 7.67 (1H, d, J = 8.0 Hz, NHCO), 7.50-7.40 (3H, m, ArH), 7.35-7.20 (10H, m, ArH), 6.37 (1H, d, J = 8.8H, Ph$_2$CH), 4.36 (2H, s, NCH$_2$CO)

Example 21-2

Benzylation of the Compound 49

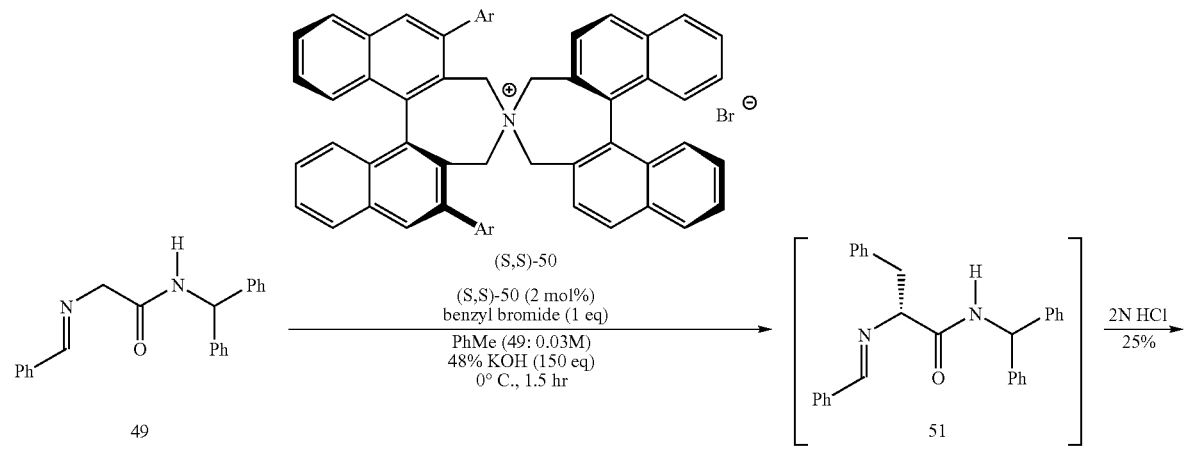

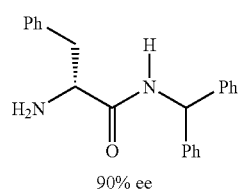

90% ee

52

Ar = 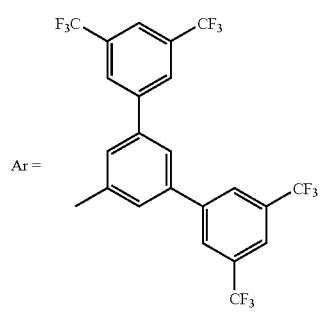

Under a nitrogen atmosphere, an aldimine Schiff base of glycine diphenylmethylamide and benzaldehyde (compound 49) (49.2 mg; 0.15 mmol), benzyl bromide (25.6 mg; 0.15 mmol), and the compound (S,S)-50 (5 mg; 3 μmol) were added to toluene (5 mL), and the mixture was stirred vigorously (1000 rpm) with ice-salt cooling. When the internal temperature thereof had dropped to 0° C. or less, 48% KOH aqueous solution (2.6 g; 22 mmol, 150 equivalents) was added thereto. The mixture was stirred for 1.5 hours while maintaining the internal temperature between 0° C. and 5° C. Distilled water (5 mL) and toluene (10 mL) were added thereto, the toluene layer was collected, and the alkylated Schiff base (compound 51) was extracted with further toluene (10 mL).

The toluene layers collected were combined, and then 2 N hydrochloric acid (20 mL) was added thereto and the mixture was stirred at room temperature for one hour. The aqueous layer was collected by separation, and then the aqueous layer was washed with toluene (10 mL), and a 48% sodium hydroxide aqueous solution was added thereto until pH of the aqueous layer reached not lower than 11 (confirmed by universal pH test paper). The mixture was extracted with ethyl acetate (10 mL×3) to collect the ethyl acetate layer. The ethyl acetate layer was dried over magnesium sulfate and concentrated under reduced pressure to give the title compound 52 (30 mg; by NMR analysis it was found that this contained glycine diphenylmethylamide derived from the starting material 49, and thus the content of the compound 52 was approximately 40%, and the yield from the compound 49 was 25%). The optical purity was 90% ee.

The optical purity of the compound 52 was measured by HPLC under the following conditions:

Column: CHIRALCEL OD-H (4.6 mmφ×25 cm)

Mobile phase: hexane/ethanol/diethylamine=95/5/0.1

Flow rate: 0.5 mL/min

Temperature: room temperature

Detection: UV 225 nm

Retention time: (S)-form=31 min; (R)-form: 63 min.

The NMR spectrum of the obtained compound 52 is shown in Table 16.

TABLE 16

NMR spectrum of compound 52

400 MHz $^1$H-NMR (CDCl$_3$): δ 8.02 (1H, d, J = 9.0 Hz, N—H), 7.40-7.10 (15H, m, ArH), 6.37 (1H, d, J = 9.0 Hz, Ph$_2$CH), 3.77 (1H, m, NCHCO), 3.27 (1H, dd, J = 4.2 Hz, 13.7 Hz, PhCH$_2$C), 2.81 (1H, dd, J = 8.9 Hz, 13.7 Hz, PhCH$_2$C), 1.60 (2H, br s, NH$_2$)

Example 22

Benzylation of the p-tolualdehyde Schiff Base of Glycine Ethyl Ester (Compound 53)

The compound 53 was prepared (yield 89%) using p-tolualdehyde instead of benzaldehyde in Reference Example 1. The NMR spectrum of the obtained compound 53 is shown in Table 17.

TABLE 17

NMR spectrum of compound 53

400 MHz $^1$H-NMR (CDCl$_3$): δ 8.25 (1H, s, CH=N), 7.70-7.60 (2H, m), 7.30-7.20 (2H, m), 4.38 (2H, s, N—CH$_2$—C), 4.24 (2H, q, J = 7.2 Hz, O—CH$_2$—C), 2.52 (3H, s) 1.30 (3H, t, 7.2 Hz, C—CH$_3$)

Then, the reaction was carried out for six hours under the same conditions as in Example 1, except that the compound 53 (2.05 g; 10 mmol) was used instead of the compound 3 to give the compound 6 (1.16 g; yield 63%, optical purity 93% ee).

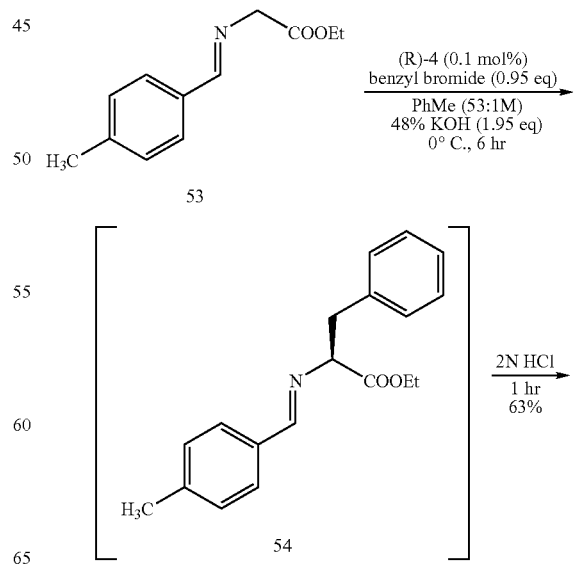

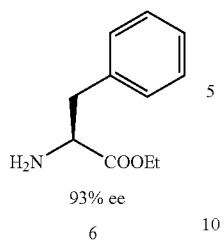

93% ee

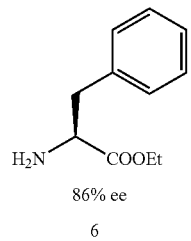

86% ee

Example 23

Benzylation of the o-tolualdehyde Schiff Base of Glycine Ethyl Ester (Compound 55)

The compound 55 was prepared (yield 96%) using o-tolualdehyde instead of the benzaldehyde in Reference Example 1. The NMR spectrum of the obtained compound 55 is shown in Table 18.

TABLE 18

NMR spectrum of compound 55

400 MHz $^1$H-NMR (CDCl$_3$): δ 8.73 (1H, s, CH=N), 7.95-7.90 (1H, m), 7.45-7.10 (3H, m), 4.42 (2H, s, N—CH$_2$—C), 4.24 (2H, q, J = 7.2 Hz, O—CH$_2$—C), 2.67 (3H, s) 1.31 (3H, t, 7.2 Hz, C—CH$_3$)

The reaction was carried out for four hours under the same conditions as in Example 1, except that the compound 55 (2.05 g; 10 mmol) was used instead of the compound 3 to give the compound 6 (1.28 g; yield 70%, optical purity 86% ee).

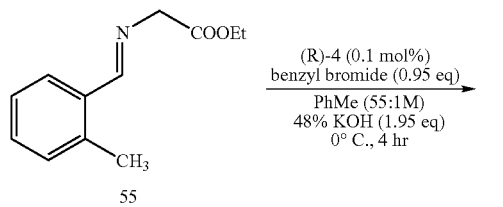

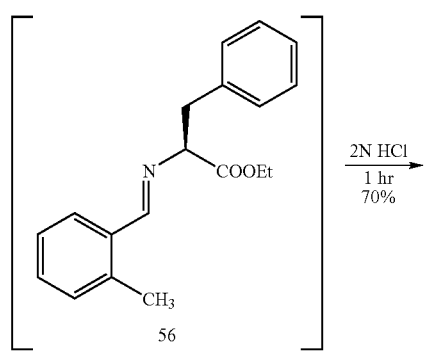

INDUSTRIAL APPLICABILITY

According to the present invention, it is possible to obtain a reaction product without allowing the effect of racemization to occur, even when an aldimine-type Schiff base is used. Thus, an asymmetrical mono-substituted alkylated compound can be provided less expensively.

The invention claimed is:

1. A method for stereoselectively producing a compound represented by the following formula (I):

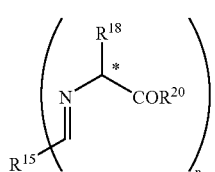

comprising:
initiating a reaction of a Schiff base represented by the formula (II):

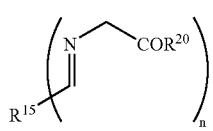

with a compound represented by the formula (III):

$$R^{18}—W \qquad (III)$$

in a medium in the presence of an optically-active phase-transfer catalyst other than a phase-transfer catalyst complexed with an optically-active metal atom and an aqueous inorganic base solution; and quenching the reaction at a time earlier than a time for completion of a stoichiometric reaction of the compound represented by the formula (II) with the compound represented by the formula (III);

wherein in the formula (I) and the formula (II), $R^{15}$ is phenyl, naphthyl, anthryl, phenanthryl, pyridyl, pyrrolyl, imidazolyl, furyl, indolyl, benzothiophen-2-yl, thienyl, oxazolyl, thiazolyl, 3,4-methylenedioxyphenyl, 3,4-ethylenedioxyphenyl or tetrazolyl that may be substituted with at least one group selected from the group consisting of:

a $C_1$ to $C_8$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_8$ alkyl group that may be branched and that may be substituted with a halogen atom, or a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

$R^{20}$ is –$OR^{19}$ (where $R^{19}$ is a $C_1$ to $C_8$ alkyl group that may be substituted with a halogen atom or an aryl group that may be substituted with a halogen atom, and that may be branched or form a cyclic group) or —$NR^{50}R^{51}$ (where $R^{50}$ and $R^{51}$ are each independently a hydrogen atom, —$CHR^{28}R^{29}$ (where $R^{28}$ is a group selected from the group consisting of a hydrogen atom, and an aryl group that may be substituted with a $C_1$ to $C_4$ alkyl group that may be substituted with a halogen atom, a $C_1$ to $C_3$ alkoxy group that may be substituted with a halogen atom, or a halogen atom, and $R^{29}$ is an aryl group that may be substituted with a $C_1$ to $C_4$ alkyl group that may be substituted with a halogen atom, a $C_1$ to $C_3$ alkoxy group that may be substituted with a halogen atom, or a halogen atom) or —$OR^{101}$ (where $R^{101}$ is a $C_1$ to $C_8$ alkyl group or a benzyl group));

wherein in the formula (I) and the formula (III);

$R^{18}$ is a group selected from the group consisting of:

(i) a $C_1$ to $C_{10}$ alkyl group that may be branched or form a cyclic group and that may be substituted with a halogen atom, wherein the alkyl group may be substituted with at least one group selected from the group consisting of:

a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), a halogen atom, —$COR^9$ (where $R^9$ is a $C_1$ to $C_4$ alkyl group that may be branched and that may be substituted with a halogen atom), and —$CO_2R^9$ (where $R^9$ is a $C_1$ to $C_4$ alkyl group that may be branched and that may be substituted with a halogen atom);

(ii) a $C_3$ to $C_{15}$ alkyl group or substituted allyl group that may be branched or form a cyclic group and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and the alkyl moiety of the aralkyl group is a $C_1$ to $C_6$ alkyl group that may be branched or form a cyclic group and that may be substituted with a halogen atom;

(vi) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and the alkyl moiety of the heteroaralkyl group is a $C_1$ to $C_6$ alkyl group that may be branched or form a cyclic group and that may be substituted with a halogen atom; and (vii) a $C_3$ to $C_9$ propargyl group or substituted propargyl group that may be branched and that may be substituted with a halogen atom;

wherein in the formula (III),

W is a functional group that has a leaving ability;

wherein in the formula (I) and the formula (II), n is an integer from 1 to 4; and wherein in the formula (I), \* shows a newly produced asymmetric center.

2. The method of claim 1, wherein the optically-active phase-transfer catalyst is an optically-active quaternary ammonium salt phase-transfer catalyst.

3. The method of claim 2, wherein the optically-active quaternary ammonium salt phase-transfer catalyst is an optically-active quaternary ammonium salt that has a biphenyl backbone and/or binaphthyl backbone, or an optically-active cinchona alkaloid quaternary ammonium salt.

4. The method of claim 2, wherein the optically-active quaternary ammonium salt phase-transfer catalyst is an optically-active quaternary ammonium salt, or an enantiomer thereof, which is represented by:

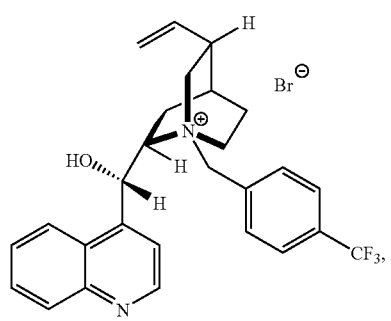

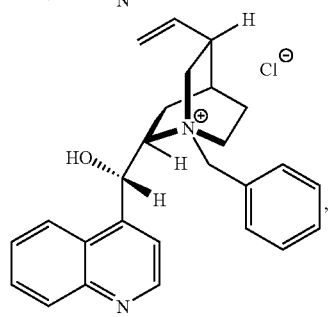

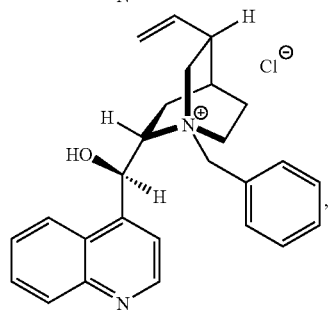

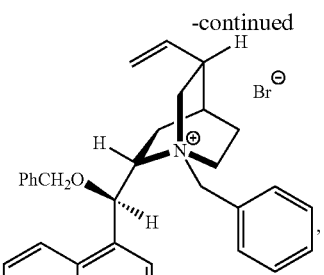

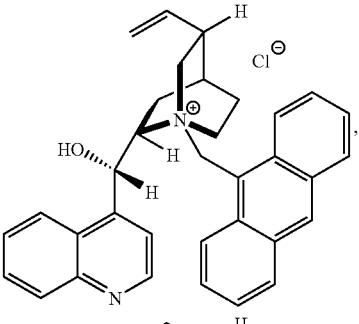

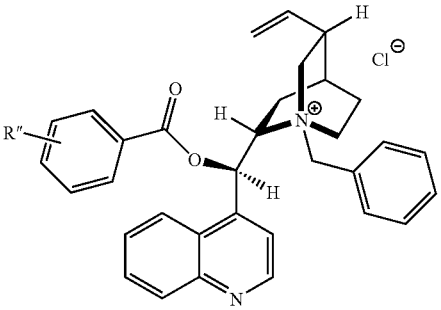

(where R" is a hydrogen atom, a $C_1$ to $C_4$ alkyl group that may be branched, a $C_1$ to $C_5$ alkoxy group that may be branched, or a halogen atom),

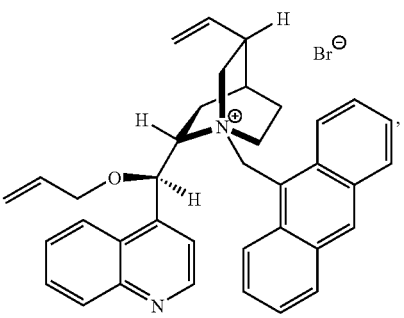

93
-continued
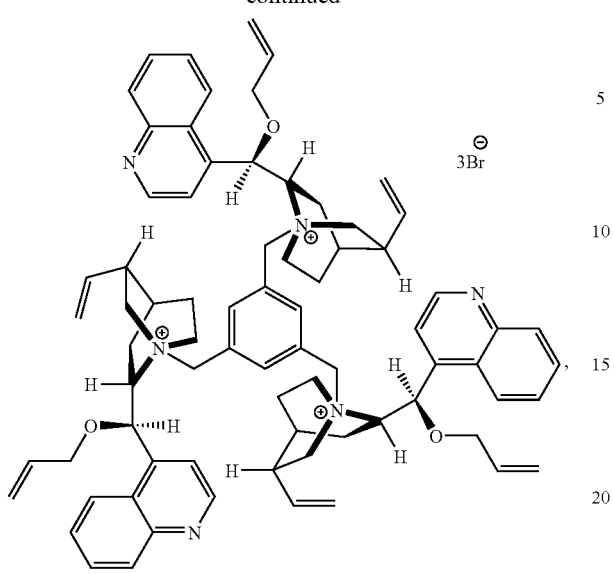
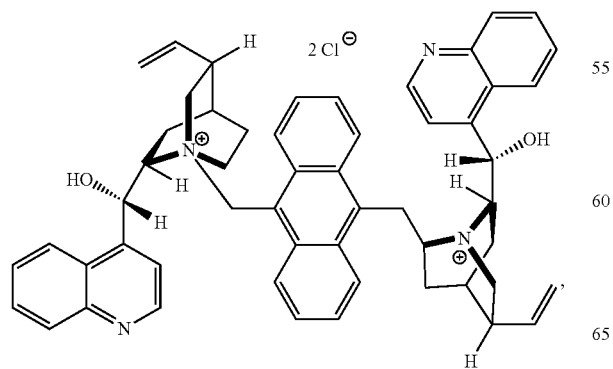
(where R is a hydrogen atom or an allyl group, and Z is Cl or Br),
94
-continued
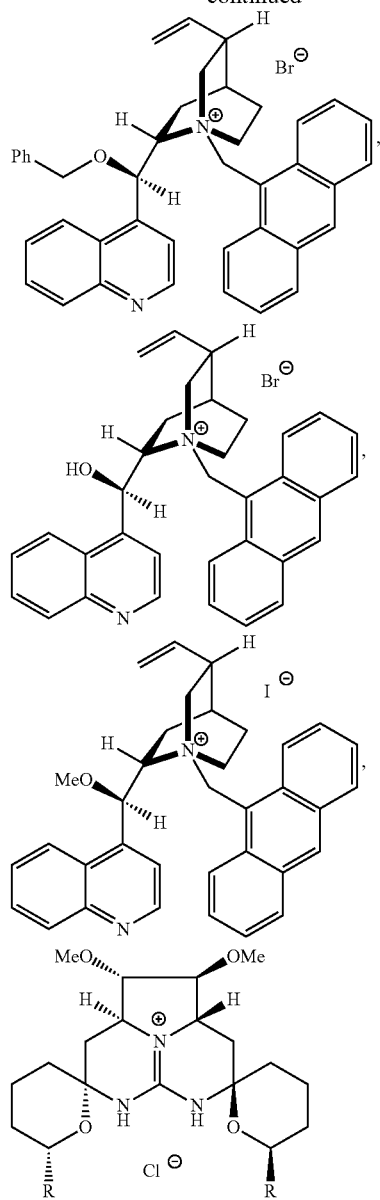
(where R is a methyl group or a hydrogen atom),
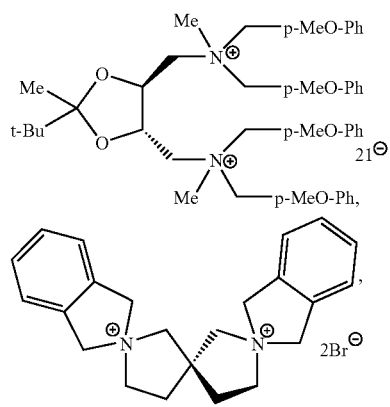

-continued

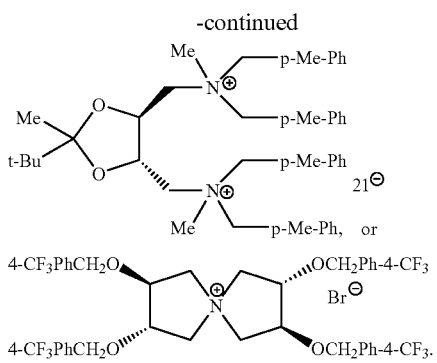

5. The method of claim 3, wherein the optically-active quaternary ammonium salt phase-transfer catalyst that has a biphenyl backbone and/or binaphthyl backbone is an optically-active quaternary ammonium salt represented by:

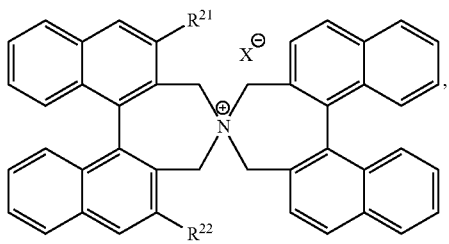

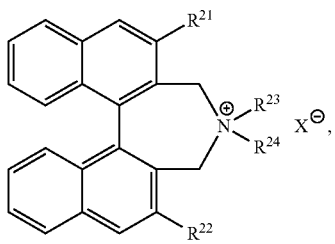

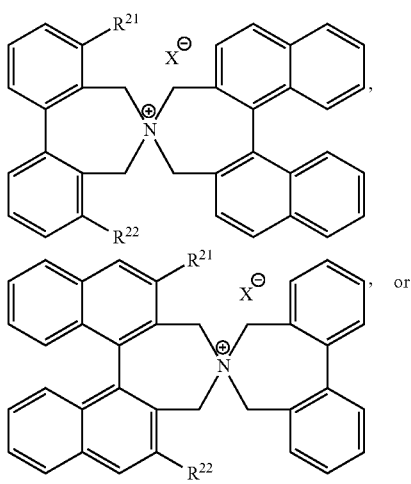

-continued

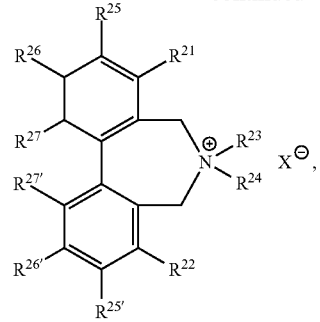

wherein
$R^{21}$ and $R^{22}$ are each independently a group selected from the group consisting of:
(i) a hydrogen atom;
(ii) —$NR^{30}R^{31}$ (where $R^{30}$ and $R^{31}$ are each independently a hydrogen atom or a $C_1$ to $C_4$ alkyl group that may be branched and that may be substituted with a halogen atom);
(iii) a cyano group;
(iv) a nitro group;
(v) a carbamoyl group;
(vi) an N—($C_1$ to $C_4$ alkyl)carbamoyl group;
(vii) an N,N-di($C_1$ to $C_4$ alkyl)carbamoyl group;
(viii) —$NHCOR^9$ (where $R^9$ is a $C_1$ to $C_4$ alkyl group that may be branched and that may be substituted with a halogen atom);
(ix) a halogen atom;
(x) a $C_1$ to $C_6$ alkyl group that may be branched or form a cyclic group and that may be substituted with a halogen atom;
(xi) a $C_2$ to $C_6$ alkenyl group that may be branched or form a cyclic group and that may be substituted with a halogen atom;
(xii) a $C_2$ to $C_6$ alkynyl group that may be branched or form a cyclic group and that may be substituted with a halogen atom;
(xiii) an aralkyl group, wherein the aryl moiety of the aralkyl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be branched and that may be substituted with a halogen atom),
a nitro group,
a carbamoyl group, an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom;
(xiv) a heteroaralkyl group having a heteroaryl moiety, wherein the heteroaryl moiety may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom;
(xv) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom;
or may be substituted with —O—(CH$_2$)$_p$—O— (where p is 1 or 2) at positions 3 and 4 that are taken together; and
(xvi) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
(xvii) —S(O)$_n$—R (where n is 0, 1, or 2, and R is a $C_1$ to $C_4$ alkyl group that may be branched and that may be substituted with a halogen atom);
R$^{25}$, R$^{25'}$, R$^{26}$, and R$^{26'}$ are each independently a group selected from the group consisting of:
(i) a hydrogen atom;
(ii) a halogen atom;
(iii) an alkyl group, wherein the alkyl group is a $C_1$ to $C_5$ alkyl group that may be substituted with a halogen atom and/or an aryl group, and/or that may be branched or form a cyclic group; and
(iv) an alkoxy group, wherein the alkoxy group is a $C_1$ to $C_5$ alkoxy group that may be substituted with a halogen atom and/or an aryl group, and/or that may be branched or form a cyclic group;
R$^{27}$ and R$^{27'}$ are each independently a group selected from the group consisting of:
(i) a halogen atom;
(ii) an alkyl group, wherein the alkyl group is a $C_1$ to $C_5$ alkyl group that may be substituted with a halogen atom and/or an aryl group, and/or that may be branched or form a cyclic group; and
(iii) an alkoxy group, wherein the alkoxy group is a $C_1$ to $C_5$ alkoxy group that may be substituted with a halogen atom and/or an aryl group, and/or that may be branched or form a cyclic group;
R$^{23}$ and R$^{24}$ are each independently a group selected from the group consisting of:
(i) a $C_1$ to $C_{30}$ alkyl group that may be branched or form a cyclic group and that may be substituted with a halogen atom;
(ii) a $C_2$ to $C_{12}$ alkenyl group that may be branched or form a cyclic group and that may be substituted with a halogen atom;

(iii) a $C_2$ to $C_{12}$ alkynyl group that may be branched or form a cyclic group and that may be substituted with a halogen atom;

(iv) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(v) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(vi) —$(CH_2)_n OCONR^{10}R^{11}$ (where $R^{10}$ and $R^{11}$ are each independently a group selected from the group consisting of:

(1) a hydrogen atom;

(2) a $C_1$ to $C_4$ alkyl group that may be branched and that may be substituted with a halogen atom;

(3) a $C_2$ to $C_6$ alkenyl group that may be branched or form a cyclic group and that may be substituted with a halogen atom;

(4) a $C_2$ to $C_6$ alkynyl group that may be branched or form a cyclic group and that may be substituted with a halogen atom;

(5) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(6) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)

carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom;

(7) an aryl group, wherein the aryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom; and (8) a heteroaryl group, wherein the heteroaryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom;

and n is an integer from 1 to 12);

(vii) —(CH$_2$)$_n$CONR$^{12}$R$^{13}$ (where R$^{12}$ and R$^{13}$ are each independently a group selected from the group consisting of:

(1) a hydrogen atom;

(2) a C$_1$ to C$_4$ alkyl group that may be branched and that may be substituted with a halogen atom;

(3) an aryl group, wherein the aryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom; and (4) a heteroaryl group, wherein the heteroaryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be branched and that may be substituted with a halogen atom), a nitro group, a carbamoyl group, an N—(C$_1$ to C$_4$ alkyl)carbamoyl group, an N,N-di(C$_1$ to C$_4$ alkyl) carbamoyl group, or —NHCOR$^9$ (where R$^9$ is a C$_1$ to C$_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom;
and n is an integer from 1 to 12);
(viii) —$(CH_2)_n NR^{12}COR^{13}$ (where $R^{12}$ and $R^{13}$ are each independently a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom; and
(4) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom;
and n is an integer from 1 to 12);
(ix) —$(CH_2)_n NR^{12}R^{13}$ (where $R^{12}$ and $R^{13}$ are each independently a group selected from the group consisting of:
(1) a hydrogen atom;
(2) a $C_1$ to $C_4$ alkyl group that may be branched;
(3) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom; and
(4) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom;

and n is an integer from 1 to 12);

(x) —(CH$_2$)$_n$Y—OR$^{12}$ (where Y is a $C_1$ to $C_4$ divalent saturated hydrocarbon group that may be branched, and R$^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom;

and n is an integer from 1 to 12);

(xi) —(CH$_2$)$_n$—OR$^{12}$ (where R$^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom;
and n is an integer from 1 to 12);
(xii) —(CH$_2$)$_n$—S—R$^{12}$ (where R$^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
(4) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom;
and n is an integer from 1 to 12);
(xiii) —(CH$_2$)$_n$—SO—R$^{12}$ (where R$^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
(4) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group,
—$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

and n is an integer from 1 to 12); and (xiv) —$(CH_2)_n$—$SO_2$—$R^{12}$ (where $R^{12}$ is a group selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

and n is an integer from 1 to 12); or $R^{23}$ and $R^{24}$ are taken together to form a divalent group selected from the group consisting of:

—$(CH_2)_m$— (where m is an integer from 2 to 8);

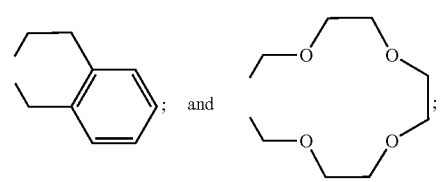

and $X^-$ is a halide anion.

6. A method for stereoselectively producing a compound represented by the following formula (I):

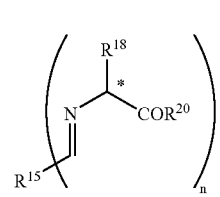

comprising:

initiating a reaction of a Schiff base represented by the formula (II):

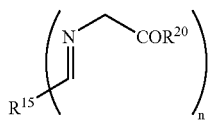

with a compound represented by the formula (III):

$$R^{18}—W \qquad (III)$$

in a medium in the presence of an optically-active phase-transfer catalyst other than a phase-transfer catalyst complexed with an optically-active metal atom and an aqueous inorganic base solution; and quenching the reaction at a time t that satisfies the following inequality not to allow the effect of racemization to occur:

$$50 < \frac{A_t(\% \ ee) \times YLD_t(\%)}{100} < 100$$

(where $A_t$ is the optical purity (% ee) of the compound represented by the formula (I) that is obtained by quenching the reaction at a time t from the initiation of the reaction; and $YLD_t$ is the yield (%) of the compound represented by the formula (I) that is obtained by quenching the reaction at a time t from the initiation of the reaction);

wherein in the formula (I) and the formula (II), $R^{15}$ is phenyl, naphthyl, anthryl, phenanthryl, pyridyl, pyrrolyl, imidazolyl, furyl, indolyl, benzothiophen-2-yl, thienyl, oxazolyl, thiazolyl, 3,4-methylenedioxyphenyl, 3,4-ethylenedioxyphenyl or tetrazolyl that may be substituted with at least one group selected from the group consisting of:

a $C_1$ to $C_8$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_8$ alkyl group that may be branched and that may be substituted with a halogen atom, or a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

$R^{20}$ is –$OR^{19}$ (where $R^{19}$ is a $C_1$ to $C_8$ alkyl group that may be substituted with a halogen atom or an aryl group that may be substituted with a halogen atom, and that may be branched or form a cyclic group) or —$NR^{50}R^{51}$ (where $R^{50}$ and $R^{51}$ are each independently a hydrogen atom, —$CHR^{28}R^{29}$ (where $R^{28}$ is a group selected from the group consisting of a hydrogen atom, and an aryl group that may be substituted with a $C_1$ to $C_4$ alkyl group that may be substituted with a halogen atom, a $C_1$ to $C_3$ alkoxy group that may be substituted with a halogen atom, or a halogen atom, and $R^{29}$ is an aryl group that may be substituted with a $C_1$ to $C_4$ alkyl group that may be substituted with a halogen atom, a $C_1$ to $C_3$ alkoxy group that may be substituted with a halogen atom, or a halogen atom) or —$OR^{101}$ (where $R^{101}$ is a $C_1$ to $C_8$ alkyl group or a benzyl group));

in the formula (I) and the formula (III), $R^{18}$ is a group selected from the group consisting of:

(i) a $C_1$ to $C_{10}$ alkyl group that may be branched or form a cyclic group and that may be substituted with a halogen atom, wherein the alkyl group may be substituted with at least one group selected from the group consisting of a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), a halogen atom, —$COR^9$ (where $R^9$ is a $C_1$ to $C_4$ alkyl group that may be branched and that may be substituted with a halogen atom), and —$CO_2R^9$ (where $R^9$ is a $C_1$ to $C_4$ alkyl group that may be branched and that may be substituted with a halogen atom);

(ii) a $C_3$ to $C_{15}$ alkyl group or substituted allyl group that may be branched or form a cyclic group and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl) carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be branched and that may be substituted with a halogen atom), a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
the alkyl moiety of the aralkyl group is a $C_1$ to $C_6$ alkyl group that may be branched or form a cyclic group and that may be substituted with a halogen atom;
(vi) a heteroaralkyl group having a heteroaryl moiety, wherein the heteroaryl moiety may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be branched and that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom),
a cyano group,
—NR$^{30}$R$^{31}$ (where R$^{30}$ and R$^{31}$ are each independently a hydrogen atom or a $C_1$ to $C_4$ alkyl group that may be branched and that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where R$^9$ is a $C_1$ to $C_4$ alkyl group that may be branched and that may be substituted with a halogen atom), and
a halogen atom; and
the alkyl moiety of the heteroaralkyl group is a $C_1$ to $C_6$ alkyl group that may be branched or form a cyclic group and that may be substituted with a halogen atom; and
(vii) a $C_3$ to $C_9$ propargyl group or substituted propargyl group that may be branched and that may be substituted with a halogen atom;
in the formula (III),
W is a functional group that has a leaving ability;
in the formula (I) and the formula (II),
n is an integer from 1 to 4; and
in the formula (I),
* shows a newly produced asymmetric center.

7. The method of claim 1, wherein the medium is selected from the group consisting of benzene, toluene, xylene, ethyl ether, isopropyl ether, tetrahydrofuran, dioxane, methyl tert-butyl ether, and cyclopentyl methyl ether.

8. The method of claim 1, wherein the medium is a biphasic medium containing water and a water-immiscible medium, the water-immiscible medium is selected from the group consisting of benzene, toluene, xylene, ethyl ether, isopropyl ether, methyl tert-butyl ether, and cyclopentyl methyl ether.

9. The method of claim 6, wherein the medium is selected from the group consisting of benzene, toluene, xylene, ethyl ether, isopropyl ether, tetrahydrofuran, dioxane, methyl tert-butyl ether, and cyclopentyl methyl ether.

10. The method of claim 6, wherein the medium is a biphasic medium containing water and a water-immiscible medium, the water-immiscible medium is selected from the group consisting of benzene, toluene, xylene, ethyl ether, isopropyl ether, methyl tert-butyl ether, and cyclopentyl methyl ether.

* * * * *

UNITED STATES PATENT AND TRADEMARK OFFICE
CERTIFICATE OF CORRECTION

| | | |
|---|---|---|
| PATENT NO. | : 8,722,919 B2 | Page 1 of 1 |
| APPLICATION NO. | : 11/997168 | |
| DATED | : May 13, 2014 | |
| INVENTOR(S) | : Keiji Maruoka et al. | |

It is certified that error appears in the above-identified patent and that said Letters Patent is hereby corrected as shown below:

In the Claims

Column 96, line 2, chemical structure represented by:

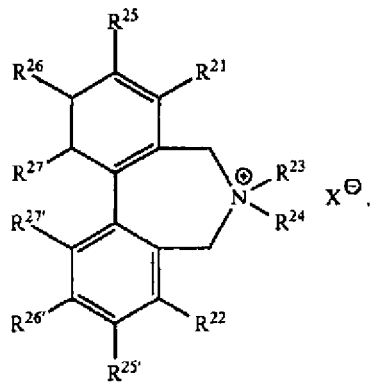

should be

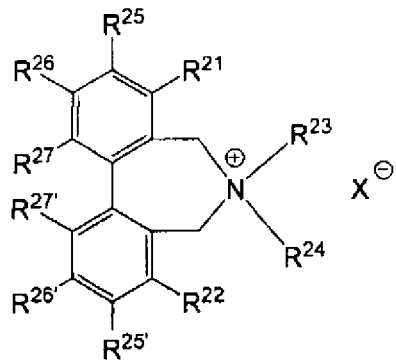

Signed and Sealed this
Fourteenth Day of October, 2014

Michelle K. Lee
*Deputy Director of the United States Patent and Trademark Office*